US012622858B2

(12) United States Patent
Kang et al.

(10) Patent No.: US 12,622,858 B2
(45) Date of Patent: May 12, 2026

(54) ADDITIVES FOR COLORING AGENTS AND METHODS OF USE THEREOF

(71) Applicant: Living Proof, Inc., Boston, MA (US)

(72) Inventors: Soo-Young Kang, Boston, MA (US); Zhaoxia Ji, Boston, MA (US); Dinara A. Villanueva, Boston, MA (US); Nawodi Abeyrathna, Boston, MA (US)

(73) Assignee: Living Proof, Inc., Boston, MA (US)

(*) Notice: Subject to any disclaimer, the term of this patent is extended or adjusted under 35 U.S.C. 154(b) by 0 days.

(21) Appl. No.: 17/622,453

(22) PCT Filed: Jun. 26, 2020

(86) PCT No.: PCT/US2020/039759
§ 371 (c)(1),
(2) Date: Dec. 23, 2021

(87) PCT Pub. No.: WO2020/264257
PCT Pub. Date: Dec. 30, 2020

(65) Prior Publication Data

US 2023/0225952 A1 Jul. 20, 2023

Related U.S. Application Data

(60) Provisional application No. 62/868,210, filed on Jun. 28, 2019.

(51) Int. Cl.
*A61Q 5/10* (2006.01)
*A61K 8/34* (2006.01)
(Continued)

(52) U.S. Cl.
CPC ............ *A61K 8/4986* (2013.01); *A61K 8/342* (2013.01); *A61K 8/347* (2013.01); *A61K 8/361* (2013.01);
(Continued)

(58) Field of Classification Search
CPC ...... A61K 8/4986; A61K 8/342; A61K 8/347; A61K 8/361; A61K 8/365; A61K 8/44;
(Continued)

(56) References Cited

U.S. PATENT DOCUMENTS 6,409,772 B2 6/2002 Pruche et al.
7,905,926 B2 * 3/2011 DeGeorge .............. A61K 8/411 8/405
(Continued)

FOREIGN PATENT DOCUMENTS

AU 2007256544 A1 12/2007
CN 108778232 A 11/2018
(Continued)

OTHER PUBLICATIONS

Mintel, Conditioner. Retrieved online at: http://www.gndp.com. 4 pages, Aug. 7, 2015.
(Continued)

*Primary Examiner* — Eisa B Elhilo
(74) *Attorney, Agent, or Firm* — McCarter & English, LLP; Michael J. DeGrazia; Sujatha Rochford

(57) ABSTRACT

Disclosed are methods for coloring hair, comprising applying a mixture comprising one or more hair dyes and an additive as a pre-treatment, as a simultaneous treatment, as a post-treatment, or a combination thereof.

6 Claims, 37 Drawing Sheets

(51) Int. Cl.

| | |
|---|---|
| ***A61K 8/36*** | (2006.01) |
| ***A61K 8/365*** | (2006.01) |
| ***A61K 8/44*** | (2006.01) |
| ***A61K 8/49*** | (2006.01) |

(52) U.S. Cl.
CPC ................ *A61K 8/365* (2013.01); *A61K 8/44* (2013.01); *A61K 8/447* (2013.01); *A61K 8/4913* (2013.01); *A61K 8/492* (2013.01); *A61K 8/498* (2013.01); *A61Q 5/10* (2013.01); *A61K 2800/43* (2013.01); *A61K 2800/88* (2013.01)

(58) Field of Classification Search
CPC ...... A61K 8/447; A61K 8/4913; A61K 8/492; A61K 8/498; A61K 2800/43; A61K 2800/88; A61K 8/36; A61K 8/362; A61K 8/368; A61K 8/375; A61K 8/46; A61K 8/22; A61K 8/31; A61K 8/35; A61K 8/38; A61K 8/42; A61K 8/602; A61K 8/64; A61K 8/671; A61K 8/676; A61K 8/678; A61Q 5/10; A61Q 5/065
USPC .............................................................. 8/405
See application file for complete search history.

(56) References Cited

U.S. PATENT DOCUMENTS

| | | | | |
|---|---|---|---|---|
| 8,034,126 | B2 * | 10/2011 | Vainshelboim | A61K 8/9789 8/405 |
| 8,430,935 | B2 * | 4/2013 | Goutsis | A61K 8/8152 8/405 |
| 2010/0192969 | A1 | 8/2010 | DeGeorge et al. | |
| 2010/0313362 | A1 | 12/2010 | Vainshelboim et al. | |
| 2013/0042882 | A1 | 2/2013 | Goutsis et al. | |
| 2013/0156716 | A1 * | 6/2013 | Yontz | A61Q 5/10 8/405 |

FOREIGN PATENT DOCUMENTS

| | | | | |
|---|---|---|---|---|
| CN | 109674680 | A | 4/2019 | |
| DE | 102006038449 | A1 | 12/2007 | |
| EP | 2873412 | A1 | 5/2015 | |
| JP | 2004-123618 | A | 4/2004 | |
| JP | 2009-539783 | A | 11/2009 | |
| JP | 2019-038793 | A | 3/2019 | |
| WO | WO 2007140856 | A1 * | 12/2007 | A61Q 5/10 |
| WO | 2017/157993 | A1 | 9/2017 | |
| WO | 2020/264257 | A1 | 12/2020 | |

OTHER PUBLICATIONS

Mintel, Hair Colourant for Petroleum Bath. Retrieved online at: http://www.gndp.com. 6 pages, Nov. 9, 2009.
Mintel, Country Colors Hair Dye. Retrieved online at: http://www.gndp.com. 3 pages, Mar. 4, 2004.
Mintel, Root Rehab Emergency Retouch Kit. Retrieved online at: http://www.gndp.com. 11 pages, Sep. 30, 2009.
Mintel, Precision Creme. Retrieved online at: http://www.gndp.com. 4 pages, Jul. 27, 2018.
International Search Report and Written Opinion for Application No. PCT/US2020/039759, dated Sep. 10, 2020, 14 pages.

* cited by examiner

Figure 10
No Additive
L-Alanine
N-acetyl L-Alanine
Glycine
N-acetyl Glycine
Serine
N-acetyl Serine

ADDITIVES FOR COLORING AGENTS AND METHODS OF USE THEREOF

RELATED APPLICATIONS

This application is a 35 U.S.C. § 371 national stage filing of International Application No. PCT/US2020/039759, filed on Jun. 26, 2020, which claims priority to U.S. Provisional Application No. 62/868,210, filed Jun. 28, 2019, the entire contents of each of which are incorporated herein by reference.

BACKGROUND

Hair coloring is by far the most popular form of chemical hair treatment. Whether the purpose is to cover gray hair or to change the color of your entire head of hair, hair coloring is an easy process to achieve that. Hair coloring agents (also referred to as hair dyes) used for coloring can be classified into three categories based on the color durability: temporary, semi-permanent, and permanent. Among them, permanent hair dyes are most commonly used. A permanent hair dye generally consists of oxidative dye precursors (i.e., primary intermediates and couplers) that are oxidized by hydrogen peroxide and form large color molecules inside the hair.

Although the oxidative dyes provide long-lasting color, the aggressive chemicals used or formed during the coloring process can cause extensive hair damage. To reduce the hair damage by coloring, various methods for coloring hair with additives have been developed. For example, an additive can be incorporated into a coloring mixture or can be used as a separate pre-treatment or post-treatment step before or after dyeing hair. In addition to the damage caused by hair dyeing, hair is repeatedly weathered in response to stresses such as washing, drying, brushing, combing, rubbing, styling, and sun exposure, the 18-methyl eicosanoic acid layer is lost and the hair surface becomes more hydrophilic, negatively charged, and damaged-feeling. Efforts were also made to deliver more consistent hair color throughout the hair and to provide improved color resistance to regular shampoo and conditioner washes, i.e., improved color retention. Methods to reduce damage and to deliver more consistent hair color with hair dyeing is still an unmet need.

SUMMARY

In one aspect, the disclosure provides a method for coloring hair, comprising:

i) providing a hair sample; and ii) applying to the hair sample for a period of time a mixture, comprising one or more hair dyes and an additive in a concentration of about 0.1% by weight to about 15% by weight, thereby producing a color-treated hair sample.

In another aspect, the disclosure provides a method for coloring hair, comprising:

i) providing a hair sample; and ii) applying to the hair sample for a period of time a composition comprising one or more hair dyes and an additive in a concentration of about 0.1% by weight to about 15% by weight of the total weight of the composition, thereby producing a color-treated hair sample.

In another aspect, the disclosure provides a method for coloring hair, comprising:

i) providing a hair sample;

ii) applying an additive in a concentration of about 0.1% by weight to about 15% by weight to the hair sample for a period of time, thereby producing a treated hair sample; and iii) applying to the treated hair sample a mixture, comprising one or more hair dyes, thereby producing a color-treated hair sample.

In another aspect, the disclosure provides a method for coloring hair, comprising:

i) providing a hair sample;

ii) applying a composition comprising an additive in a concentration of about 0.1% by weight to about 15% by weight of the total weight of the composition to the hair sample for a period of time, thereby producing a treated hair sample; and iii) applying to the treated hair sample a mixture, comprising one or more hair dyes, thereby producing a color-treated hair sample.

In another aspect, the disclosure provides a method for coloring hair, comprising:

i) providing a hair sample;

ii) applying to the hair sample for a period of time a mixture, comprising one or more hair dyes, thereby producing a color-treated hair sample; and iii) applying an additive in a concentration of about 0.1% by weight to about 15% by weight to the color-treated hair sample.

In another aspect, the disclosure provides a method for coloring hair, comprising:

i) providing a hair sample;

ii) applying to the hair sample for a period of time a mixture, comprising one or more hair dyes, thereby producing a color-treated hair sample; and iii) applying a composition comprising an additive in a concentration of about 0.1% by weight to about 15% by weight of the total weight of the composition to the color-treated hair sample.

In another aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample; and iii) applying to the treated hair sample for a period of time a mixture, comprising one or more hair dyes and a second additive in a concentration of about 0.1% by weight to about 15% by weight, thereby producing a color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the first composition to the hair sample for a period of time, thereby producing a treated hair sample; and iii) applying to the treated hair sample for a period of time a second composition comprising one or more hair dyes and a second additive in a concentration of about 0.1% by weight to about 15% by weight of the total weight of the second composition, thereby producing a color-treated hair sample.

In another aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample;

iii) applying to the treated hair sample for a period of time a mixture, comprising one or more hair dyes, thereby producing a color-treated hair sample; and iv) applying a second additive in a concentration of about 0.1% by weight to about 15% by weight to the color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the first composition to the hair sample for a period of time, thereby producing a treated hair sample;

iii) applying to the treated hair sample for a period of time a mixture, comprising one or more hair dyes, thereby producing a color-treated hair sample; and iv) applying a second composition comprising a second additive in a concentration of about 0.1% by weight to about 15% by weight of the total weight of the second composition to the color-treated hair sample.

In another aspect, the disclosure provides a method for coloring hair, comprising:

i) providing a hair sample;

ii) applying to the hair sample for a period of time a mixture, comprising one or more hair dyes and a first additive in a concentration of about 0.1% by weight to about 15% by weight, thereby producing a color-treated hair sample; and iii) applying a second additive in a concentration of about 0.1% by weight to about 15% by weight to the color-treated hair sample.

In another aspect, the disclosure provides a method for coloring hair, comprising:

i) providing a hair sample;

ii) applying to the hair sample for a period of time a first composition comprising one or more hair dyes and a first additive in a concentration of about 0.1% by weight to about 15% by weight of the total weight of the first composition, thereby producing a color-treated hair sample; and iii) applying a second composition comprising a second additive in a concentration of about 0.1% by weight to about 15% by weight of the total weight of the second composition to the color-treated hair sample.

In another aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample;

iii) applying to the treated hair sample for a period of time a mixture, comprising one or more hair dyes and a second additive in a concentration of about 0.1% by weight to about 15% by weight, thereby producing a color-treated hair sample; and iv) applying a third additive in a concentration of about 0.1% by weight to about 15% by weight to the color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the composition to the hair sample for a period of time, thereby producing a treated hair sample;

iii) applying to the treated hair sample for a period of time a second composition comprising one or more hair dyes and a second additive in a concentration of about 0.1% by weight to about 15% by weight of the total weight of the second composition, thereby producing a color-treated hair sample; and iv) applying a third composition comprising a third additive in a concentration of about 0.1% by weight to about 15% by weight of the total weight of the third composition to the color-treated hair sample.

In another aspect, the disclosure provides a kit, comprising i) an additive composition comprising one or more additives; and ii) instructions for use.

In another aspect, the disclosure provides a kit, comprising i) a hair dye composition comprising one or more hair dyes;

ii) an additive composition comprising one or more additives; and iii) instructions for use.

In another aspect, the disclosure provides i) a hair dye composition comprising a plurality of oxidative dye precursors;

ii) an additive composition comprising one or more additives; and iii) instructions for use.

In another aspect, the disclosure provides a kit, comprising i) a first additive composition comprising one or more additives;

ii) a second additive composition comprising one or more additives; and iii) instructions for use.

In another aspect, the disclosure provides a kit, comprising i) a hair dye composition comprising one or more hair dyes;

ii) a first additive composition comprising one or more additives;

iii) a second additive composition comprising one or more additives; and iv) instructions for use.

In another aspect, the disclosure provides a kit, comprising i) a first additive composition comprising one or more additives;

ii) a second additive composition comprising one or more additives;

iii) a third additive composition comprising one or more additives; and iv) instructions for use.

In another aspect, the disclosure provides a kit, comprising i) a hair dye composition comprising one or more hair dyes;

ii) a first additive composition comprising one or more additives;

iii) a second additive composition comprising one or more additives;

iv) a third additive composition comprising one or more additives; and v) instructions for use.

BRIEF DESCRIPTION OF THE FIGURES

FIG. 32(*b*) depicts total color loss, ΔE, after 3, 7, and 10 washes.

FIG. 35(*b*) denaturation temperatures of hair tresses after coloring treatment treated with either LP developed system or commercial products.

DETAILED DESCRIPTION

Overview

Figure 1:
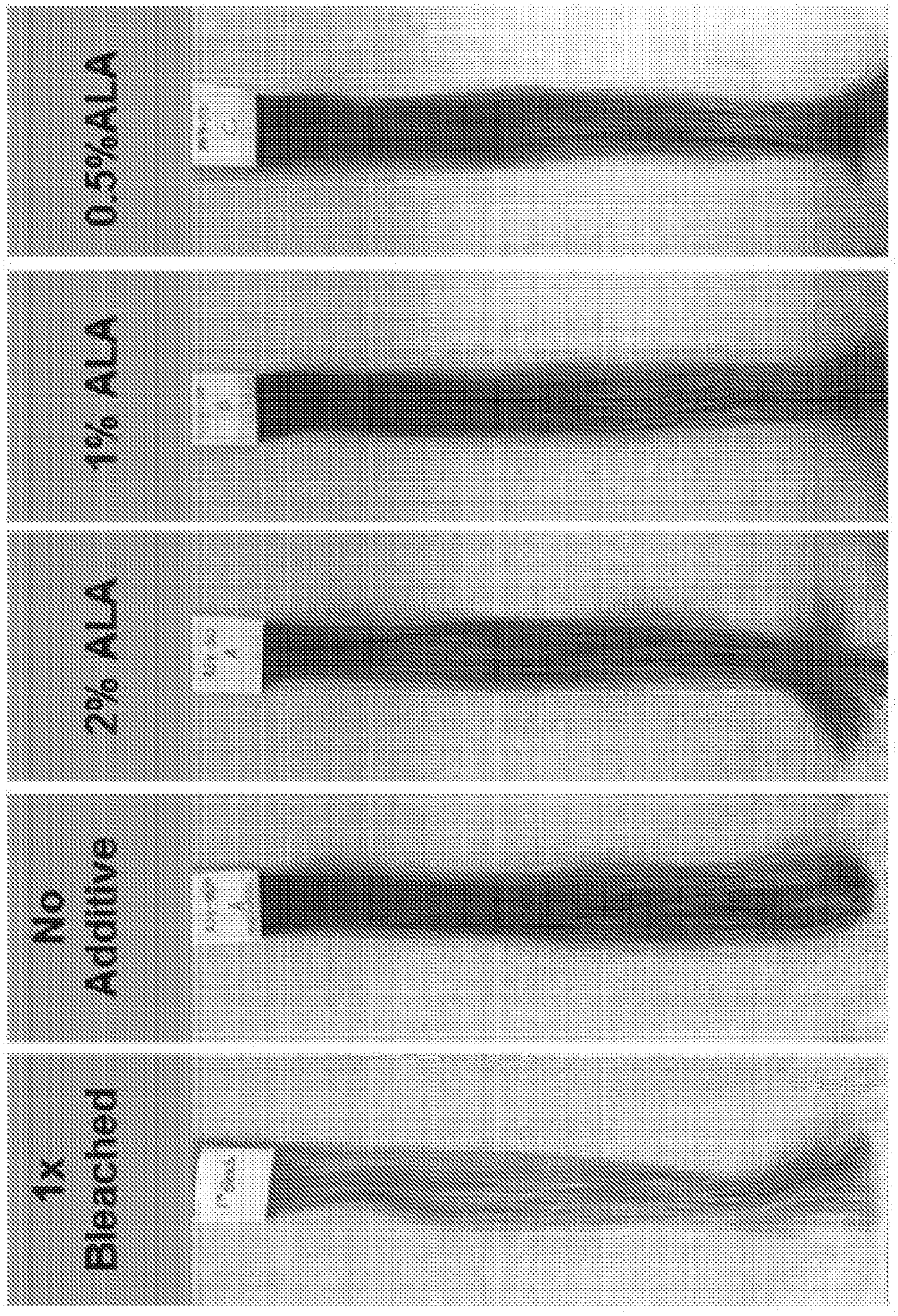
FIG. 1 depicts an image showing the color development on 1× bleached hair tresses at different alpha lipoic acid (ALA) concentrations, in the range of 0.5 wt % to 2 wt %, in the final color mixture compared to control with no additive.

A permanent hair dye generally consists of oxidative dye precursors (i.e., primary intermediates and couplers) that are oxidized by hydrogen peroxide and form large color molecules inside the hair. Although the oxidative dyes provide long-lasting color, the aggressive chemicals used or formed during the coloring process can cause extensive hair damage. Hair becomes weathered and damaged in response to stresses, including normal wear and tear, harsh cleaning agents (including solvents), washing, drying, brushing, combing, rubbing, styling, bleaching, dyeing, and sun exposure. To reduce the hair damage by coloring and other processes, various methods for coloring hair with additives have been developed. For example, an additive can be incorporated into a coloring mixture or can be used as a separate pre-treatment or post-treatment step before or after dyeing hair. Efforts were also made to deliver more consistent hair color throughout the hair and to provide improved color resistance to regular shampoo and conditioner washes, i.e., improved color retention. Methods to reduce damage and to deliver more consistent hair color with hair dyeing is still an unmet need.

Exemplary Methods for Coloring Hair with Additives

Provided herein are methods for coloring hair with additives. In some embodiments, an additive is in a mixture comprising one or more hair dyes. In some embodiments, an additive is applied before applying a mixture comprising one or more hair dyes. In some embodiments, an additive is applied after applying a mixture comprising one or more hair dyes.

In some embodiments of the methods disclosed herein, the additive composition comprises one or more additives. In some embodiments, the additive composition is a drop-in composition. In some embodiments, the additive is applied simultaneously with a hair dye composition comprising one or more hair dyes. In one aspect, the disclosure provides a method for coloring hair, comprising:

i) providing a hair sample; and
ii) applying to the hair sample for a period of time a mixture, comprising one or more hair dyes and an additive in a concentration of about 0.1% by weight to about 15% by weight, thereby producing a color-treated hair sample.

In another aspect, the disclosure provides a method for coloring hair, comprising:

i) providing a hair sample; and
ii) applying to the hair sample for a period of time a composition comprising one or more hair dyes and an additive in a concentration of about 0.1% by weight to about 15% by weight of the total weight of the composition, thereby producing a color-treated hair sample.

In another aspect, the disclosure provides a method for coloring hair, comprising:

i) providing a hair sample; and
ii) applying to the hair sample for a period of time a hair composition comprising a mixture of a hair dye, alpha lipoic acid, and at least one amino acid and/or N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, N-acetyl alanine, and N-acetyl L-cysteine or a combination thereof, wherein the total concentration of the alpha lipoic acid and the at least one amino acid and/or the at least one N-acetyl amino acid is about 0.1% by weight to about 15% (e.g., about 0.1% by weight to about 10%) by weight of the total weight of the hair composition, thereby producing a color-treated hair sample.

In some embodiments of the methods disclosed herein, the additive is applied as a pre-treatment. In some embodiments, the additive composition is applied before the hair dye composition. In one aspect, the disclosure provides a method for coloring hair, comprising:

i) providing a hair sample;
ii) applying an additive in a concentration of about 0.1% by weight to about 15% by weight to the hair sample for a period of time, thereby producing a treated hair sample; and
iii) applying to the treated hair sample a mixture, comprising one or more hair dyes, thereby producing a color-treated hair sample.

In another aspect, the disclosure provides a method for coloring hair, comprising:

i) providing a hair sample;
ii) applying a composition comprising an additive in a concentration of about 0.1% by weight to about 15% by weight of the total weight of the composition to the hair sample for a period of time, thereby producing a treated hair sample; and
iii) applying to the treated hair sample a mixture, comprising one or more hair dyes, thereby producing a color-treated hair sample.

In another aspect, the disclosure provides a method for coloring hair, comprising:

i) providing a hair sample;
ii) applying a composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetylserine, and N-acetylalanine or a combination thereof, wherein the total concentration of the N-acetyl-L-Cysteine and the at least one amino acid and/or the at least one N-acetyl amino acid is about 0.1% by weight to about 15% (e.g., about 0.1% by weight to about 10%) by weight of the total weight of the first hair composition to the hair sample for a period of time, thereby producing a treated hair sample; and iii) applying to the treated hair sample a mixture, comprising one or more hair dyes, thereby producing a color-treated hair sample.

In some embodiments of the methods disclosed herein, the additive is applied as a post-treatment. In some embodiments, the additive composition is applied after the hair dye composition. In one aspect, the disclosure provides a method for coloring hair, comprising:

i) providing a hair sample;

ii) applying to the hair sample for a period of time a mixture, comprising one or more hair dyes, thereby producing a color-treated hair sample; and iii) applying an additive in a concentration of about 0.1% by weight to about 15% by weight to the color-treated hair sample.

In another aspect, the disclosure provides a method for coloring hair, comprising:

i) providing a hair sample;

ii) applying to the hair sample for a period of time a mixture, comprising one or more hair dyes, thereby producing a color-treated hair sample; and iii) applying a composition comprising an additive in a concentration of about 0.1% by weight to about 15% by weight of the total weight of the composition to the color-treated hair sample.

In another aspect, the disclosure provides a method for coloring hair, comprising:

i) providing a hair sample; and ii) applying to the hair sample for a period of time a first hair composition comprising a hair dye, thereby producing a color-treated hair sample; and iii) applying to the hair a second hair composition comprising gluconolactone, citric acid, and at least one amino acid and/or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine and N-acetyl-L-cysteine or a combination thereof, wherein the total concentration of gluconolactone, citric acid, and the at least one amino acid and/or the at least one N-acetyl amino acid is about 0.1% by weight to about 15% (e.g., about 0.1% by weight to about 10%) by weight of the total weight of the second hair composition, thereby producing a color-treated hair sample.

In some embodiments, an additive is applied during multiple steps of the method for coloring hair. In some embodiments, the additives are different. In some embodiments, the additives are the same. In some embodiments, a first additive is applied as a pre-treatment and a second additive is applied simultaneously with a hair dye composition comprising one or more hair dyes. In one aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample; and iii) applying to the treated hair sample for a period of time a mixture, comprising one or more hair dyes and a second additive in a concentration of about 0.1% by weight to about 15% by weight, thereby producing a color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the first composition to the hair sample for a period of time, thereby producing a treated hair sample; and iii) applying to the treated hair sample for a period of time a second composition comprising one or more hair dyes and a second additive in a concentration of about 0.1% by weight to about 15% by weight of the total weight of the second composition, thereby producing a color-treated hair sample.

In another aspect, the disclosure provides a method for coloring hair, comprising:

i) providing a hair sample;

ii) applying a first composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the N-acetyl-L-Cysteine and the at least one amino acid and/or the at least one N-acetyl amino acid is about 0.1% by weight to about 15% (e.g., about 0.1% by weight to about 10%) by weight of the total weight of the first composition to the hair sample for a period of time, thereby producing a treated hair sample; and iii) applying to the treated hair sample for a period of time a second composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, and tryptophan, pyrrolidone carboxylic acid, N-acetyl glycine, N-acetyl serine, N-acetyl alanine, and N-acetyl L-cysteine or a combination thereof, wherein the total concentration of the alpha lipoic acid and the at least amino acid and/or the at least one N-acetyl amino acid is about 0.1% by weight to about 10% by weight of the total weight of the second composition, thereby producing a color-treated hair sample.

In some embodiments, a first additive is applied as a pre-treatment and a second additive is applied as a post-treatment. In one aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample;

iii) applying to the treated hair sample for a period of time a mixture, comprising one or more hair dyes, thereby producing a color-treated hair sample; and iv) applying a second additive in a concentration of about 0.1% by weight to about 15% by weight to the color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the first composition to the hair sample for a period of time, thereby producing a treated hair sample;

iii) applying to the treated hair sample for a period of time a mixture, comprising one or more hair dyes, thereby producing a color-treated hair sample; and iv) applying a second composition comprising a second additive in a concentration of about 0.1% by weight to about 15% by weight of the total weight of the second composition to the color-treated hair sample.

In another aspect, the disclosure provides a method for coloring hair, comprising:

i) providing a hair sample;

ii) applying a first composition comprising N-acetyl-L-cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the N-acetyl-L-cysteine and the at least one amino acid and/or the at least one N-acetyl amino acid is about 0.1% by weight to about 15% (e.g., about 0.1% by weight to about 10%) by weight of the total weight of the first composition to the hair sample for a period of time, thereby producing a treated hair sample;

iii) applying to the treated hair sample for a period of time a mixture, comprising one or more hair dyes, thereby producing a color-treated hair sample; and iv) applying a second composition comprising gluconolactone and citric acid, and at least one amino acid and/or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine, and N-acetyl-L-Cysteine or a combination thereof, wherein the total concentration of gluconolactone, citric acid and the at least one amino acid and/or the at least one N-acetyl amino acid is about 0.1% by weight to about 15% (e.g., about 0.1% by weight to about 10%) by weight of the total weight of the second composition to the color-treated hair sample.

In some embodiments, a first additive is applied simultaneously with a hair dye composition comprising one or more hair dyes and a second additive is applied as a post-treatment. In one aspect, the disclosure provides a method for coloring hair, comprising:

i) providing a hair sample;

ii) applying to the hair sample for a period of time a mixture, comprising one or more hair dyes and a first additive in a concentration of about 0.1% by weight to about 15% by weight, thereby producing a color-treated hair sample; and iii) applying a second additive in a concentration of about 0.1% by weight to about 15% by weight to the color-treated hair sample.

In another aspect, the disclosure provides a method for coloring hair, comprising:

i) providing a hair sample;

ii) applying to the hair sample for a period of time a first composition comprising one or more hair dyes and a first additive in a concentration of about 0.1% by weight to about 15% by weight of the total weight of the first composition, thereby producing a color-treated hair sample; and iii) applying a second composition comprising a second additive in a concentration of about 0.1% by weight to about 15% by weight of the total weight of the second composition to the color-treated hair sample.

In another aspect, the disclosure provides a method for coloring hair, comprising:

i) providing a hair sample;

ii) applying to the hair sample for a period of time a first composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, N-acetyl alanine, and N-acetyl L-cysteine or a combination thereof, wherein the total concentration of the alpha lipoic acid and the at least one amino acid and/or the at least one N-acetyl amino acid is about 0.1% by weight to about 15% (e.g., about 0.1% by weight to about 10%) by weight of the total weight of the first composition, thereby producing a color-treated hair sample; and iii) applying a second composition comprising gluconolactone and citric acid, and at least one amino acid or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine, and N-acetyl-L-Cysteine or a combination thereof, wherein the total concentration of gluconolactone, citric acid and the at least one amino acid or the at least one N-acetyl amino acid is about 0.1% by weight to about 15% (e.g., about 0.1% by weight to about 10%) by weight of the total weight of the second composition to the color-treated hair sample.

In some embodiments, a first additive is applied as a pre-treatment, a second additive is applied simultaneously with a hair dye composition comprising one or more hair dyes, and a third additive is applied as a post-treatment. In one aspect, the disclosure provides a method for coloring hair, comprising:

i) providing a hair sample;

ii) applying a first additive in a concentration of about 0.1% by weight to about 15% by weight to the hair sample for a period of time, thereby producing a treated hair sample;

iii) applying to the treated hair sample for a period of time a mixture, comprising one or more hair dyes and a second additive in a concentration of about 0.1% by weight to about 15% by weight, thereby producing a color-treated hair sample; and iv) applying a third additive in a concentration of about 0.1% by weight to about 15% by weight to the color-treated hair sample.

In another aspect, the disclosure provides a method for coloring hair, comprising:

i) providing a hair sample;

ii) applying a first composition comprising a first additive in a concentration of about 0.1% by weight to about 15% by weight of the total weight of the composition to the hair sample for a period of time, thereby producing a treated hair sample;

iii) applying to the treated hair sample for a period of time a second composition comprising one or more hair dyes and a second additive in a concentration of about 0.1% by weight to about 15% by weight of the total weight of the second composition, thereby producing a color-treated hair sample; and iv) applying a third composition comprising a third additive in a concentration of about 0.1% by weight to about 15% by weight of the total weight of the third composition to the color-treated hair sample.

In another aspect, the disclosure provides a method for coloring hair, comprising:

i) providing a hair sample;

ii) applying a first composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine or a combination thereof, wherein the total concentration of the N-acetyl-L-Cysteine and the at least one amino acid and/or the at least one N-acetyl amino acid is about 0.1% by weight to about 15% (e.g., about 0.1% by weight to about 10%) by weight of the total weight of the first composition to the hair sample for a period of time, thereby producing a treated hair sample;

iii) applying to the treated hair sample for a period of time a second composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, N-acetyl alanine, and N-acetyl L-cysteine or a combination thereof, wherein the total concentration of the alpha lipoic acid and the at least one amino acid and/or the at least one N-acetyl amino acid is about 0.1% by weight to about 15% (e.g., about 0.1% by weight to about 10%) by weight of the total weight of the second composition, thereby producing a color-treated hair sample; and iv) applying a third composition comprising gluconolactone and citric acid and at least one amino acid and/or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine, and N-acetyl-L-Cysteine or a combination thereof, wherein the total concentration of the gluconolactone, citric acid, and the at least one amino acid and/or the at least one N-acetyl amino acid is about 0.1% by weight to about 15% (e.g., about 0.1% by weight to about 10%) by weight of the total weight of the third composition to the color-treated hair sample.

Additives

In some embodiments, the additive reduces hair damage during color treatment, improves consistency of hair color delivery, and improves color retention upon washing. In some embodiments, the additive improves the sensory properties of the color-treated hair sample. In some embodiments, the sensory properties are tactile properties (e.g., manageability, smoothness, conditioned feeling) and/or visual properties (e.g., frizz, fiber alignment, and curl shape).

In some embodiments of the methods disclosed herein, one or more additives are applied as a pre-treatment, in combination with a hair dye composition comprising one or more hair dyes, as a post-treatment, or a combination thereof. In some embodiments, each step of applying the additive comprises applying one or more additives. In some embodiments, the additive is selected from the group consisting of one or more antioxidants, one or more amino acids, one or more amino acid derivatives, one or more acidifiers, one or more polycarboxylic acids, one or more fatty acids, one or more fatty alcohols, one or more fatty acid esters, one or more peptides, one or more thiol compounds, one or more monomers, one or more catalysts, and a mixture thereof.

Antioxidants

In some embodiments, the additive comprises one or more antioxidants. In some embodiments, the additive is one or more antioxidants selected from the group consisting of acetyl-L-carnitine, alpha-carotene, alpha lipoic acid, alpha-tocopherol, apigenin, ascorbic acid, astaxanthin, benserazide, beta-carotene, caffeic acid, canthaxanthin, catechin, catecholamine, chicoric acid, chlorogenic acid, cinnamic acid, coenzyme Q10, cryptoxanthin, curcumin, cyanidin, daidzein, delphinidin, dopamine, edravone, ellagic acid, epicatechin, epigallocatechin, eriodictyol, erythorbic acid, ferulic acid, gallic acid, gallocatechin, genistein, glutathione, glycitein, gossypetin, guaiacol, hesperidin, hesperetin, isoprenaline, isorhamnetin, kaempferol, lutein, luteolin, lycopene, malvidin, melatonin, mequinol, myricetin, naringenin, naringin, norepinephrine, p-coumaric acid, pelargonidin, peonidin, petunidin, protocatechuic acid, pterostilbene, pyrogallol, quercetin, resorcinol, resveratrol, retinol, rosmarinic acid, rutin, salicylic acid, sinapic acid, syringic acid, tangeritin, taxifolin, theaflavin, tocopherol, tocotrienol, ubiquinol, uric acid, vanillic acid, and zeaxanthin. In some embodiments, the additive is alpha lipoic acid, which has the following structural formula:

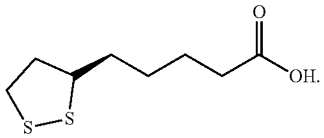

In some embodiments, the one or more antioxidants comprises one or more polyphenols. In some embodiments, the one or more polyphenols included, but are not limited to, apigenin, benserazide, catechin, chicoric acid, chlorogenic acid, cinnamic acid, curcumin, cyanidin, daidzein, delphinidin, ellagic acid, epicatechin, epigallocatechin, eriodictyol, ferulic acid, gallic acid, gallocatechin, genistein, glycitein, gossypetin, guaiacol, hesperidin, hesperetin, isoprenaline, isorhamnetin, kaempferol, luteolin, malvidin, mequinol, myricetin, naringenin, naringin, norepinephrine, p-coumaric acid, pelargonidin, peonidin, petunidin, protocatechuic acid, pterostilbene, pyrogallol, quercetin, resorcinol, resveratrol, rosmarinic acid, rutin, salicylic acid, sinapic acid, tangeritin, taxifolin, and theaflavin.

Amino Acids, Amino Acid Derivatives, and Peptides

In some embodiments, the additive comprises one or more amino acids, one or more amino acid derivatives, or one or more peptides. In some embodiments, the additive comprises one or more amino acids (naturally occurring L-form or D-form), which may be identified by the conventional three-letter abbreviations indicated in the below table.

TABLE 1

(Amino acid codes)

| Name | 3-letter code | Name | 3-letter code |
|---|---|---|---|
| Alanine | Ala | Leucine | Leu |
| Arginine | Arg | Lysine | Lys |
| Asparagine | Asn | Methionine | Met |
| Aspartic acid | Asp | Phenylalanine | Phe |
| Cysteine | Cys | Proline | Pro |

TABLE 1-continued

| (Amino acid codes) | | | |
|---|---|---|---|
| Name | 3-letter code | Name | 3-letter code |
| Glutamic acid | Glu | Serine | Ser |
| Glutamine | Gln | Threonine | Thr |
| Glycine | Gly | Tryptophan | Trp |
| Histidine | His | Tyrosine | Tyr |
| Isoleucine | Ile | Valine | Val |

In some embodiments, the additive comprises one or more amino acids or one and/or more amino acid derivatives. In some embodiments, the one or more amino acid derivatives are one or more N-acetyl amino acids (e.g., N-acetyl alanine and N-acetyl L-cysteine (NALC)). In some embodiments, the additive comprises one or more amino acids and/or one or more amino acid derivatives, which are selected from the group consisting of glycine (Gly), L-alanine (L-Ala), L-cysteine (L-Cys), L-serine (L-Ser), N-acetyl glycine (Ac-Gly), N-acetyl alanine (Ac-Ala), N-acetyl cysteine (Ac-Cys), and N-acetyl serine (Ac-Ser). In some embodiments, the additive comprises an amino acid mixture selected from the group consisting of Ac-Gly, Ac-Ala, Ac-Cys, and Ac-Ser. In some embodiments, the additive comprises at least one amino acid selected from glycine, alanine, serine, proline, tyrosine, arginine, lysine, aspartic acid, glutamic acid, tryptophan, and pyrrolidone carboxylic acid, or a combination thereof. In some embodiments, the additive is glycine. In some embodiments, the additive is a combination of glycine and tyrosine. In some embodiments, the additive is a combination of glycine, alanine and tyrosine. In some embodiments, the additive is a combination of glycine, tyrosine, and proline. In some embodiments, the concentration of the additive (e.g., the amino acid or combination of amino acids) is fixed at about 2% of the total weight of the composition to which is it in. In some embodiments the additive is an N-acetyl amino acid. In some embodiments, the additive comprises an amino acid mixture or a peptide mixture used in personal care industries. In some embodiments, the additive comprises one or more amino acids or the one or more peptides selected from the group consisting of FISION® KeraVeg 18 (blend of vegetable amino acids), PRODEW® 500 (amino acid blend), Vegetamide 18MEA-NJ (cetearamidoethyldiethonium succinoyl hydrolyzed pea protein), Vegetamide 18MEA-MR (cetearamidoethyl diethonium hydrolyzed rice protein), KERARICE™ (rice peptides and amino acids), KERATRIX™ (carob tree hydrolyzate), Promois WK-PD (hydrolyzed keratin), GLUADIN® Kera-P LM (low molecular weight vegetable peptides), and KERANUTRI™ (*Ceratonia Siliqua* seed extract and hydrolyzed soy protein). In some embodiments, the additive is selected from the group consisting of FISION® KeraVeg 18, PRODEW® 500, Vegetamide 18MEA-NJ, Vegetamide 18MEA-MR, KERARICE™, KERATRIX™, Promois WK-PD, GLUADIN® Kera-P LM, and KERANUTRI™. In some embodiments, the additive is KERATRIX™.

Acidifiers and Polycarboxylic Acids

In some embodiments, the additive comprises one or more acidifiers and/or one or more polycarboxylic acids. In some embodiments, the additive is one or more acidifiers and/or one or more polycarboxylic acids selected from the group consisting of aldobionic acid, azelaic acid, citric acid, ethylenediaminetetraacetic acid (EDTA), ethylenediamine-N,N'-disuccinic acid, gluconolactone, glutamic acid N,N-diacetic acid, lactic acid, methylglycinediacetic acid, tartaric acid, tartronic acid, gluconic acid, succinic acid, itaconic acid, acetic acid, malonic acid, malic acid, 1,2,3,4-butanetetracarboxylic acid, and a mixture thereof. In some embodiments, the one or more acidifiers and one or more polycarboxylic acids comprises citric acid and gluconolactone.

Fatty Acids, Fatty Alcohols, and Fatty Acid Esters

In some embodiments, the additive comprises one or more fatty acids, one or more fatty alcohols, and/or one or more fatty acid esters. In some embodiments, the additive is one or more fatty acids, one or more fatty alcohols, and/or one or more fatty acid esters selected from the group consisting of butyric acid, caproic acid, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoclaidic acid, linolenic acid, arachidonic acid, eicosapentaenoic acid, erucic acid, docosahexaenoic acid, argan oil, coconut oil, jojoba oil, olive oil, palm oil, tert-butyl alcohol, tert-amyl alcohol, 3-methyl-3-pentanol, ethchlorvynol, capryl alcohol, pelargonic alcohol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-octacosanol, 1-nonacosanol, myricyl alcohol, melissyl alcohol, lacceryl alcohol, geddyl alcohol cetearyl alcohol, ascorbyl palmitate, ascorbyl stearate, cetyl myristoleate, cetyl palmitate, a diglyceride, ethyl decanoate, ethyl macadmiate, ethyl octanoate, ethyl palmitate, ethylhexyl palmitate, glyceryl monostearate, glyceryl hydroxystearate, glycol distearate, glycol stearate, glycerol monolaurate, isopropyl palmitate, a monoglyceride, 2-olcoylglycerol, and a mixture thereof.

Thiol Compounds

In some embodiments, the additive comprises one or more thiol compounds. In some embodiments, each additive is a thiol compound comprising at least one free thiol group. In some embodiments, each additive is a thiol compound comprising at least two free thiol groups. In some embodiments, at least one additive is a thiol compound comprising at least two free thiol groups. In some embodiments, each additive is a thiol compound independently selected from the group consisting of a monothiol compound, a protected thiol compound, a dithiol compound, a trithiol compound, a tetrathiol compound, a thiomer, and a cyclic disulfide compound. In some embodiments, at least one thiol compound is a monothiol compound.

In some embodiments, the additive is a monothiol compound, which comprises at least one additional functional group. In some embodiments, the additive is a thiol compound comprising at least one free thiol groups and at least one additional functional group. In some embodiments, the additive is a thiol compound comprising at least two free thiol groups and at least one additional functional group. In some embodiments, the one or more additional functional groups are selected from the group consisting of an alkyl, an alkene, an alkoxyl, an acetate, a cycloalkyl, a heterocycloalkyl, an aryl, a heteroaryl, an aryloxy, a heteroaryloxy, a poly(ethylene glycol), a carborane, an alkyl amine, an alkyl amide, an aralkyl, a heteroaralkyl, and a ferrocene, wherein the alkyl, the alkene, the acetate, the cycloalkyl, the heterocycloalkyl, the aryl, the heteroaryl, the aryloxy, the heteroaryloxy, the poly(ethylene glycol), the carborane, the alkyl amine, the alkyl amide, the aralkyl, the heteroaralkyl, and the ferrocene are optionally substituted.

In some embodiments, the additive is one or more thiol compounds selected from the group consisting of 1-butanethiol; 1-decanethiol; 1-dodecanethiol; 1-heptanethiol; 1-hexadecanethiol; 1-hexanethiol; 1-nonanethiol; 1-octadecanethiol; 1-octanethiol; 1-pentadecanethiol; 1-pentanethiol; 1-propanethiol; 1-tetradecanethiol; 1-decanethiol; 1-undecanethiol; 1-dodecanethiol; (11-mercaptoundecyl)-N,N,N-trimethylammonium bromide; (11-mercaptoundecyl) hexa(ethylene glycol); (11-mercaptoundecyl)tetra(ethylene glycol); 1-(11-mercaptoundecyl)imidazole; 1-mercapto-2-propanol; 11-(1H-pyrrol-1-yl)undecane-1-thiol; 11-(ferrocenyl)undecanethiol; 11-amino-1-undecanethiol hydrochloride; 11-azido-1-undecanethiol; 11-mercapto-1-undecanol; 11-mercaptoundecanamide; 11-mercaptoundecanoic acid; 11-mercaptoundecylhydroquinone; 11-mercaptoundecylphosphonic acid; 12-mercaptododecanoic acid; 16-amino-1-hexadecanethiol hydrochloride; 16-mercaptohexadecanamide; 16-mercaptohexadecanoic acid; 3-amino-1-propanethiol hydrochloride; 3-chloro-1-propanethiol; 3-mercapto-1-propanol; 3-mercaptopropionic acid; 4-mercapto-1-butanol; 6-(ferrocenyl)hexanethiol; 6-amino-1-hexanethiol hydrochloride; 6-mercapto-1-hexanol; 6-mercaptohexanoic acid; 8-amino-1-octanethiol hydrochloride; 8-mercapto-1-octanol; 8-mercaptooctanoic acid; 9-mercapto-1-nonanol; tricthylene glycol mono-11-mercaptoundecyl ether; 11-mercaptoundecyl trifluoroacetate; 1H,1H,2H,2H-perfluorodecanethiol; 2-ethylhexanethiol; 2-methyl-1-propanethiol; 2-methyl-2-propanethiol; 3,3,4,4,5,5,6,6,6-nonafluoro-1-hexanethiol; 3-mercapto-N-nonylpropionamide; 3-methyl-1-butanethiol; 4-cyano-1-butanethiol; butyl 3-mercaptopropionate; cis-9-octadecene-1-thiol; methyl 3-mercaptopropionate; tert-dodecylmercaptan; tert-nonyl mercaptan; 1,1',4',1"-terphenyl-4-thiol; 1,4-benzenedimethanethiol; 1-adamantanethiol; 1-naphthalenethiol; 2-phenylethanethiol; 4'-bromo-4-mercaptobiphenyl; 4'-mercaptobiphenylcarbonitrile; 4,4'-bis(mercaptomethyl) biphenyl; 4-dimercaptostilbene; 4-(6-mercaptohexyloxy)benzyl alcohol; 4-mercaptobenzoic acid; 9-fluorenylmethylthiol; 9-mercaptofluorene; biphenyl-4-thiol; cyclohexanethiol; cyclopentanethiol; m-carborane-1-thiol; m-carborane-9-thiol; thiophenol; triphenylmethanethiol; L-cysteine; thioglycolic acid; thioglycerin; thiolactic acid; N-acetyl L-cysteine; 1,4-butanedithiol diacetate; [11-(methylcarbonylthio)undecyl] hexa(ethylene glycol) methyl ether; [11-(methylcarbonylthio)undecyl]tetra(ethylene glycol); [11-(methylcarbonylthio)-undecyl]-tri(ethylene glycol) acetic acid; [11-(methylcarbonylthio)undecyl]tri(ethylene glycol) methyl ether; hexa(ethylene glycol)mono-11-(acetylthio)undecyl ether; S,S'-[1,4-phenylenebis(2,1-ethynediyl-4,1-phenylene)]bis(thioacetate); S-[4-[2-[4-(2-phenylethynyl)phenyl]ethynyl]-phenyl] thioacetate; S-(10-undecenyl) thioacetate; S-(11-bromoundecyl) thioacetate; S-(4-azidobutyl)thioacetate; S-(4-bromobutyl) thioacetate; S-(4-cyanobutyl)thioacetate; dithiothreitol (DTT); 1,2-ethanedithiol; 1,3-propanedithiol; 1,4-butanedithiol; 1,5-pentanedithiol; 1,6-hexanedithiol; 1,7-heptanedithiol; 1,8-octanedithiol; 1,9-nonanedithiol; 1,10-decanedithiol; 1,11-undecanedithiol; 1,12-dodecanedithiol; 1,13-tridecanedithiol; 1,14-tetradecanedithiol; 1,16-hexadecanedithiol; dithiolbutylamine (DTBA); tetra (ethylene glycol) dithiol; hexa(ethylene glycol) dithiol; 2-mercaptoethyl ether; 2,2'-thiodiethanethiol; 2,2'-(ethylenedioxy) diethanethiol; propane-1,2,3-trithiol; trimethylolpropane tris(2-mercaptoacetate); trimethylolpropane tris(3-mercaptoacetate); pentaerythrityl tetrathiol; pentaerythritol tetrakis(3-mercaptopropionate); 4arm-PEG2K-SH, 4arm-PEG5K-SH, 4arm-PEG10K-SH, 4arm-PEG20K-SH, 4-arm poly(ethylene oxide) thiol-terminated, 8arm-PEG10K-SH (hexaglyerol core), 8arm-PEG10K-SH (tripentaerythritol core), 8arm-PEG20K-SH (hexaglycerol core), 8arm-PEG20K-SH (tripentaerythritol core), 8-arm poly(ethylene oxide) thiol-terminated; 1,2-dithiane-4,5-diol; alpha lipoic acid; beta lipoic acid; 3H-1,2-dithiole; 3-propyl-1,2-dithiolane; 3-acetyl-1,2-dithiolane; 1,2-dithiolane-4-carboxylic acid; 1,2-dithiolane-3-pentanol; 1,2,4-dithiazolidine; 1,2-dithiane; 1,2-dithiepane; 1,2-dithiocane; and 1,2-dithiocane-3,8-diol.

Monomers

In some embodiments, the additive comprises one or more monomers selected from the group consisting of an acrylate, a methacrylate, a monomer comprising a vinyl group, a monomer comprising an alkyne group, and a monomer comprising a maleimide group.

In some embodiments, the additive is one or more acrylate or methacrylate monomers selected from the group consisting of ethyl acrylate; propyl acrylate; isobutyl acrylate; butyl acrylate; pentyl acrylate; tert-butyl acrylate; hexyl acrylate; heptyl acrylate; octyl acrylate; isooctyl acrylate; nonyl acrylate; decyl acrylate; isodecyl acrylate; dodecyl acrylate; tridecyl acrylate; tetradecyl acrylate; hexadecyl acrylate; octadecyl acrylate; cyclopentyl acrylate; cyclohexyl acrylate; cycloheptyl acrylate; cyclooctyl acrylate; 2-(dimethylamino)ethyl acrylate; 2-(diethylamino)ethyl acrylate; 2-ethylhexyl acrylate; 3,5,5-trimethylhexyl acrylate; 8-methylnonyl acrylate; 3-isobutylnonyl acrylate; 3-(cyclohexylmethyl) nonyl acrylate; 3-butyl-7,11-dimethyldodecyl acrylate; (E)-3-butyl-7,11-dimethyldodec-2-en-1-yl acrylate; isobornyl acrylate; a PEG acrylate; 1,6-hexanediol diacrylate; octafluoropentyl acrylate; fluorescein-o-acrylate; fluorescein-o-o-diacrylate; a poly(ethylene glycol)-diacrylate (PEG-DA); and a multi-arm PEG-acrylate (PEG-AA). In some embodiments, the monomer is a poly(ethylene glycol)-diacrylate or polyethylene glycol diacrylate (PEG diacrylate or PEG-DA) selected from the group consisting of PEG-DA 250, PEG-DA 575, PEG-DA 700, PEG-DA 1 k, PEG-DA 1.5 k, PEG-DA 2 k, and PEG-DA 6 k.

In some embodiments, the additive is one or more monomers comprising a vinyl group selected from the group consisting of ethyl vinyl ether; propyl vinyl ether; isobutyl vinyl ether; butyl vinyl ether; pentyl vinyl ether; tert-butyl vinyl ether; hexyl vinyl ether; heptyl vinyl ether; octyl vinyl ether; isooctyl vinyl ether; nonyl vinyl ether; decyl vinyl ether; dodecyl vinyl ether; tetradecyl vinyl ether; hexadecyl vinyl ether; octadecyl vinyl ether; N,N-dimethyl-2-(vinyloxy)-ethylamine; cyclopentyl vinyl ether; cyclohexyl vinyl ether; cycloheptyl vinyl ether; cyclooctyl vinyl ether; 2-(dimethylamino)ethyl vinyl ether; 2-(diethylamino)ethyl vinyl ether; 2-ethylhexyl vinyl ether; 1-(vinyloxy)adamantane; vinyloxy-timethylsilane; and vinyloxy-triethylsilane.

In some embodiments, the additive is one or more monomers comprising a maleimide group selected from the group consisting of N-ethylmaleimide; N-cyclohexylmaleimide; N-arachidonylmaleimide; fluorescein-5-maleimide; a succinimidyl-[(N-maleimidopropionamido)-diethyleneglycol] ester; a poly(ethylene glycol) (PEG)-maleimide; and a methoxy-PEG-maleimide.

Catalysts

In some embodiments, the additive comprises one or more catalysts. In some embodiments, the additive comprises one or more thiol compounds and a catalyst. In some embodiments, the additive comprises one or more monomers and a catalyst. In some embodiments, the additive is one or more catalysts selected from the group consisting of an amine, a phosphine, and a radical initiator.

In some embodiments, the additive comprises one or more amine catalysts. In some embodiments, the one or more amine catalysts are selected from the group consisting of N,N-diisopropylethylamine, N-ethyldiisopropylamine, di-n-propylamine, trimethylamine, triethylamine, ethanolamine, diethanolamine, and triethanolamine.

In some embodiments, the additive comprises one or more phosphine catalysts. In some embodiments, the one or more phosphine catalysts are selected from the group consisting of dimethylphenylphosphine, diethylphenylphosphine, methyldiphenyl-phosphine, ethyldiphenylphosphine, trimethylphosphine, tripropylphosphine, triphenylphosphine, tri(o-tolyl)phosphine, tri(p-tolyl)phosphine, tris(2,4,6-trimethylphenyl)-phospine, tris(3,5-dimethylphenyl)phospine, dicyclohexyl-(2,6-diisopropylphenyl)phosphine, and tris(hydroxymethyl)phosphine.

In some embodiments of the methods disclosed herein, the additive comprises one or more radical initiator catalysts. In some embodiments, the one or more radical initiator catalysts are selected from the group consisting of a peroxide, an azo compound, a photoinitiator. In some embodiments, the radical initiator catalyst is a peroxide. In some embodiments, the radical initiator catalyst is a peroxide is selected from the group consisting of hydrogen peroxide, tert-butyl hydroperoxide, tert-butyl peracetate, cumene hydroperoxide, dicumyl peroxide, benzoyl peroxide, and tert-butyl peroxide.

In some embodiments, the radical initiator catalyst is an azo compound. In some embodiments, the azo compound is selected from the group consisting of 4,4'-azobis(4-cyanovaleric acid), 4,4'-azobis(4-cyanovaleric acid), 1,1'-azobis (cyclohexanecarbonitrile), 2,2'-azobis(2-methylpropionamidine) dihydrochloride, 2,2'-azobis(2-methylpropionitrile), and 2,2'-azobis(2-methylpropionitrile).

In some embodiments, the radical initiator catalyst is a photoinitiator. In some embodiments, the photoinitiator is an aryl ketone. In some embodiments, the photoinitiator is selected from the group consisting of acetophenone; anisoin; anthraquinone; anthroquinone-2-sulfonic acid; benzil; bezoin; benzoin ethyl ether; bezoin isobutyl ether; benzoin methyl ether; benzophenone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophen-one; 4,4'-bis(dimethylamino) benzophenone; camphorquinone; 2-chlorothioxanthen-2-one; dibenzosuberenone; 2,2'-diethoxyacetophenone; 4,4'-dihydroxybenzophenone; 2,2'-dmethoxy-2-phenylacetophenone; 4-(dimethylamino)benzophenone; 4,4'-dimethylbenzil; 2,5-dimethylbenzophenone; 3,4-dimethylbenzophenone; 2-hydroxy-2-methylpropiophenone; 4'-ethoxyacetophenone; 2-ethylantrhaquinone; 3'-hydroxyacetophenone; 4'-hydroxyaceto-phenone; 3-hydroxyacetophenone; 4-hydroxyacetophenone; 1-hydroxycyclohexyl phenyl ketone; 2-hydroxy-2-methylpropiophenone; 2-methylbenzophenone; 3-methylbenzophenone; methylbenzoylformate; 2-methyl-4'-(methylthio) 2-morpholinopropiophenone; phenantrene-quinone; 4'-phenyoxyacetophenone; thioxanthen-9-one; and diphenyl(2,4,6-trimethyl-benzoyl) phosphine oxide. In some embodiments, the photoinitiator is 2,2'-diethoxyacetophenone.

In some embodiments, when the additive comprises a monomer, the amount of the catalyst is about 0.1 mol % to about 100 mol % relative to the monomer. In some embodiments, when the additive comprises one or more thiol compounds, the amount of the catalyst is about 0.1 mol % to about 100 mol % relative to a thiol compound. In some embodiments, the amount of the catalyst is about 1 mol % to about 100 mol % relative to the monomer or relative to the thiol compound. In some embodiments, the amount of the catalyst is selected from the group consisting of about 1 mol %, about 2 mol %, about 3 mol %, about 4 mol %, about 5 mol %, about 6 mol %, about 7 mol %, about 8 mol %, about 9 mol %, about 10 mol %, 11 mol %, about 12 mol %, about 13 mol %, about 14 mol %, about 15 mol %, about 16 mol %, about 17 mol %, about 18 mol %, about 19 mol %, about 20 mol %, 21 mol %, about 22 mol %, about 23 mol %, about 24 mol %, about 25 mol %, about 26 mol %, about 27 mol %, about 28 mol %, about 29 mol %, about 30 mol %, 31 mol %, about 32 mol %, about 33 mol %, about 34 mol %, about 35 mol %, about 36 mol %, about 37 mol %, about 38 mol %, about 39 mol %, about 40 mol %, 41 mol %, about 42 mol %, about 43 mol %, about 44 mol %, about 45 mol %, about 46 mol %, about 47 mol %, about 48 mol %, about 49 mol %, about 50 mol %, 51 mol %, about 52 mol %, about 53 mol %, about 54 mol %, about 55 mol %, about 56 mol %, about 57 mol %, about 58 mol %, about 59 mol %, about 60 mol %, 61 mol %, about 62 mol %, about 63 mol %, about 64 mol %, about 65 mol %, about 66 mol %, about 67 mol %, about 68 mol %, about 69 mol %, about 70 mol %, 71 mol %, about 72 mol %, about 73 mol %, about 74 mol %, about 75 mol %, about 76 mol %, about 77 mol %, about 78 mol %, about 79 mol %, about 80 mol %, 81 mol %, about 82 mol %, about 83 mol %, about 84 mol %, about 85 mol %, about 86 mol %, about 87 mol %, about 88 mol %, about 89 mol %, about 90 mol %, 91 mol %, about 92 mol %, about 93 mol %, about 94 mol %, about 95 mol %, about 96 mol %, about 97 mol %, about 98 mol %, about 99 mol %, and about 100 mol % relative to the monomer or relative to the thiol compound. In some embodiments, the amount of the catalyst is about 1 mol % to about 75 mol % relative to the monomer or relative to the thiol compound. In some embodiments, the amount of the catalyst is about 20 mol % to about 50 mol % relative to the monomer or relative to the thiol compound.

In some embodiments, the concentration of each additive is about 0.1% by weight to about 15% by weight. In some embodiments, the total concentration of the one or more additives is about 0.1% by weight to about 15% by weight. In some embodiments, the concentration of each additive is independently selected from the group consisting of about 0.1%, about 0.2%, about 0.3%, about 0.4%, about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about % 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the one or more additives is about 0.1% by weight to about 10% by weight. In some embodiments, the concentration of each additive is about 0.1% by weight to about 10% by weight. In some embodiments, the concentration of the one or more additives is about 0.1% by weight to about 8% by weight. In some embodiments, the concentration of each additive is about 0.1% by weight to about 8% by weight. In some embodiments, the concentration of the one or more additives is about 0.1% by weight to about 5% by weight. In some embodiments, the concentration of each additive is about 0.1% by weight to about 5% by weight. In some embodiments, the concentration of the one or more additives is about 2% by weight. In some embodiments, the concentration of each additive is about 2% by weight.

Dye Compositions

In some embodiments, provided herein is a hair dye composition comprising one or more hair dyes. In some embodiments of the methods disclosed herein, a mixture comprises one or more hair dyes.

In some embodiments, the one or more hair dyes comprise one or more oxidative dyes. In some embodiments, the one or more oxidative dyes are formed from a plurality of oxidative dye precursors. In some embodiments, the plurality of oxidative dye precursors comprise one or more primary intermediates and one or more couplers. In some embodiments, the hair dye composition comprises a plurality of oxidative dye precursors.

In some embodiments, the concentration of the one or more hair dyes or of the one or more oxidative dye precursors is about 0.01% by weight to about 15% by weight. In some embodiments, the concentration of the one or more hair dyes or of the one or more oxidative dye precursors is selected from the group consisting of about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.41%, about 0.42%, about 0.43%, about 0.44%, about 0.45%, about 0.46%, about 0.47%, about 0.48%, about 0.49%, about 0.5%, about 0.51%, about 0.52%, about 0.53%, about 0.54%, about 0.55%, about 0.56%, about 0.57%, about 0.58%, about 0.59%, about 0.6%, about 0.61%, about 0.62%, about 0.63%, about 0.64%, about 0.65%, about 0.66%, about 0.67%, about 0.68%, about 0.69%, about 0.7%, about 0.71%, about 0.72%, about 0.73%, about 0.74%, about 0.75%, about 0.76%, about 0.77%, about 0.78%, about 0.79%, about 0.8%, about 0.81%, about 0.82%, about 0.83%, about 0.84%, about 0.85%, about 0.86%, about 0.87%, about 0.88%, about 0.89%, about 0.9%, about 0.91%, about 0.92%, about 0.93%, about 0.94%, about 0.95%, about 0.96%, about 0.97%, about 0.98%, about 0.99%, about 1%, about 1.01%, about 1.02%, about 1.03%, about 1.04%, about 1.05%, about 1.06%, about 1.07%, about 1.08%, about 1.09%, about 1.1% about 1.11%, about 1.12%, about 1.13%, about 1.14%, about 1.15%, about 1.16%, about 1.17%, about 1.18%, about 1.19%, about 1.2%, about 1.21%, about 1.22%, about 1.23%, about 1.24%, about 1.25%, about 1.26%, about 1.27%, about 1.28%, about 1.29%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2%, about 2.05%, about 2.1%, about 2.15%, about 2.2%, about 2.25%, about 2.3%, about 2.35%, about 2.4%, about 2.45%, about 2.5%, about 2.55%, about 2.6%, about 2.65%, about 2.7%, about 2.75%, about 2.8%, about 2.85%, about 2.9%, about 2.95%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, a about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the one or more hair dyes or of the one or more oxidative dye precursors is about 0.01% by weight to about 10% by weight. In some embodiments, the concentration of the one or more hair dyes or of the one or more oxidative dye precursors is about 0.01% by weight to about 5% by weight.

In some embodiments, the one or more primary intermediates are selected from the group consisting of para-phenylenediame, 4-aminophenol, 1-hydroxyethyl 4,5-diamino pyrazole, N,N-bis-(2-hydroxyethyl)-para-phenylene diamine, toluene-2,5-diamine, and cosmetically acceptable salts thereof.

In some embodiments, the one or more couplers are selected from the group consisting of 3-aminophenol, resorcinol, 2-methylresorcinol, 1-naphthol, 2-methyl-5-aminophenol, 4-amino-2-hydroxytoluene, 4-chlororesorcinol, 2,4-diaminophenoxyethanol, 2-amino-hydroxyethylaminoanisole, meta-phenylenediamine, 2-methyl-5-hydroxy-ethylaminophenol, 6-hydroxyindole, and cosmetically acceptable salts thereof.

In some embodiments, the mixture is selected from the group consisting of a solution, a spray, a rinse, a mousse, a gel, a powder, a shampoo and a cream. In some embodiments, the additive composition is selected from the group consisting of a solution, a spray, a rinse, a mousse, a gel, a powder, a shampoo and a cream.

In some embodiments, the mixture further comprises an alkalizing agent. In some embodiments, the alkalizing agent is selected from the group consisting of ammonium hydroxide, ammonia, an alkylamine, an alkanediamine, an alkanolamine, a polyalkylenepolyamine, a heterocyclic amine, an alkaline earth hydroxide, an alkali metal hydroxide, and a carbonate. In some embodiments, the alkalizing agent is selected from the group consisting of ammonium hydroxide; ammonia; ethylamine; dipropylamine; triethylamine; n-propylamine; isobutylamine; 2-ethylbutylamine; diethylamine; 1,3-diaminopropane; ethylenediamine; 1,2-diaminopropane; diethylenetriamine; triethylenetriamine; 2,2'-iminodipropylamine; 3,3-iminodipropylamine; bis-hexamethylenetriamine; ethanolamine; diethanolamine; isopropanolamine; di-isopropanolamine; triethanolamine; triisopropanolamine; N-methyldiethanolamine; diisopropylethanolamine; dimethylisopropanolamine; 2-amino-2-methylpropane-1,3-diol; tris(hydroxymethyl)methylamine; N-(2-hydroxyethyl) aniline; N-methyl-N(2-hydroxyethyl) aniline; N,N-bis(2-hydroxyethyl) aniline; diethylenetriamine; morpholine; N-methylmorpholine;

N-ethylmorpholine; N-hydroxyethylmorpholine; N-phenylmorpholine; piperidine; N-hydroxyethylpiperidine; piperazine; calcium hydroxide; magnesium hydroxide; sodium hydroxide; potassium hydroxide; sodium carbonate; and sodium bicarbonate. In some embodiments, the alkalizing agent is ammonia. In some embodiments, the alkalizing agent is monoethanolamine.

In some embodiments, the concentration of the alkalizing agent is about 0.05% by weight to about 15% by weight. In some embodiments, the concentration of the alkalizing agent is selected from the group consisting of about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight. In some embodiments, the concentration of the alkalizing agent is about 0.05% by weight to about 10% by weight. In some embodiments, the concentration of the alkalizing agent is about 0.1% by weight to about 5% by weight. In some embodiments, the concentration of the alkalizing agent is about 1.5% by weight to about 3.5% by weight.

In some embodiments of the methods disclosed herein, the mixture further comprises an oxidizing agent. In some embodiments of the methods disclosed herein, the oxidizing agent is packaged separately from the hair dye composition before mixing for application to the hair. In some embodiments, the oxidizing agent is a peroxide is selected from the group consisting of hydrogen peroxide, tert-butyl hydroperoxide, tert-butyl peracetate, cumene hydroperoxide, dicumyl peroxide, benzoyl peroxide, and tert-butyl peroxide. In some embodiments, oxidizing agent is hydrogen peroxide.

In some embodiments, the concentration of the oxidizing agent is about 0.5% by weight to about 15% by weight, about 0.5%, about 0.6%, about 0.7%, about 0.75%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about % 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, and about 15% by weight.

In some embodiments, the concentration of the oxidizing agent is selected from about 2.5 volume (2.5V, 0.75% by weight), 5 volume (5V, 1.5% by weight), 10 volume (10V, 3% by weight), 15 volume (15V, 4.5% by weight), 20 volume (20V, 6% by weight), 25 volume (25V, 7.5% by weight), 30 volume (30V, 9% by weight), 35 volume (35V, 10.5% by weight), 40 volume (40V, 12% by weight), and 50 volume (50V, 15% by weight).

In some embodiments, the one or more hair dyes comprise one or more direct hair dyes. In some embodiments, the one or more direct hair dyes are selected from the group consisting of Acid Blue 1, Acid Blue 3, Acid Blue 5, Acid Blue 7, Acid Blue 9, Acid Blue 62, Acid Blue 104, Acid Brown 13, Acid Orange 3, Acid Orange 6, Acid Orange 7, Acid Orange 10, Acid Orange 11, Acid Orange 20, Acid Orange 24, Acid Red 14, Acid Red 33, Acid Red 35, Acid Red 41, Acid Red 50, Acid Red 51, Acid Red 52, Acid Red 87, Acid Red 92, Acid Red 94, Acid Red 95, Acid Red 98, Acid Red 184, Acid Green 1, Acid Green 9, Acid Green 22, Acid Green 25, Acid Green 50, Acid Yellow 1, Acid Yellow 9, Acid Yellow 73, Acid Violet 9, Acid violet 50, Basic Blue 3, Basic Blue 6, Basic Blue 7, Basic Blue 9, Basic Blue 26, Basic Blue 41, Basic Blue 47, Basic Blue 99, Basic Brown 4, Basic Brown 16, Basic Brown 17, Basic Green 1, Basic Green 4, Basic Orange 1, Basic Orange 2, Basic Orange 31, Basic Red 1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11, Basic Violet 14, Basic Violet 16, Basic Yellow 11, Basic Yellow 28, Basic Yellow 40, Basic Yellow 57, Basic Yellow 87, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 72, Disperse Brown 1, Disperse Orange 3, Disperse Red 1, Disperse Red 3, Disperse Red 11, Disperse Red 13, Disperse Red 14, Disperse Red 15, Disperse Red 17, Disperse Red 19, Disperse Violet 1, Disperse Violet 4, Disperse Violet 15, Disperse Violet 27, HC Blue 2, HC Blue 4, HC Blue 5, HC Blue 6, HC Blue 8, HC Blue 9, HC Blue 10, HC Blue 11, HC Blue 12, HC Blue 13, HC Blue 14, HC Blue 15, HC Brown 1, HC Brown 2, HC Green 1, HC Orange 1, HC Orange 2, HC Orange 3, HC Orange 5, HC Red 1, HC Red 3, HC Red 7, HC Red 8, HC Red 9, HC Red 10, HC Red 11, HC Red 13, HC Red 14, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, Disperse Red 3, Disperse Red 19, Acid Black 1, Acid Red 1, Acid Red 73, Solvent Red 23, Scarlet Red, Brilliant Black 1, Brown 1, CI 20040, CI 21100, CI 21108, CI 21230, CI 27755, CI 28440, Acid Black 52, Acid Red 18, Acid Red 27, Lithol Rubin B, Betanine, Lithol Red, CI 15800, CI 15880, Hansa Red B, CI 12085, Pigment Red 22, CI 15865:2, CI 16155, Acid Red 26, CI 14700, Solvent Orange 7, Acid Red 88, CI 11680, CI 11710, CI 11725, CI 11920, CI 12010, CI 12085, CI 12120, CI 12150, CI 12370, CI 12420, CI 12480, CI 12490, Acid Yellow 23, Acid Red 195, CI 12700, CI 14700, CI 14815, CI 15525, CI 15580, CI 15630, CI 15850, CI 15980, CI 15985, CI 16035, Acid Red 155, Acid Yellow 121, Acid Red 180, Acid Yellow 11, CI 12075, CI 12100, CI 42053, Acid Violet 43, CI 69825, Solvent Blue 63, CI 58000, CI 61565, Acid Blue 80, CI 69800, CI 10006, Rhodamine B, Japan Red 104, Japan Red 223, Acid Yellow 73, CI 45396, CI 45410, CI 45370, CI 51319, and cosmetically acceptable salts thereof.

In some embodiments, the mixture further comprises one or more of the following ingredients surfactants, thickeners, fragrances, sequestering agents, UV-screening agents, waxes, silicones, preserving agents, ceramides, oils, vitamins, provitamins, opacifiers, emulsifiers, chelating agents, color retarders, solvents and buffers. In some embodiments, the additive composition, the first additive composition, the second additive composition, and/or the third additive composition further comprises one or more of the following ingredients surfactants, thickeners, fragrances, sequestering agents, UV-screening agents, waxes, silicones, preserving agents, ceramides, oils, vitamins, provitamins, opacifiers, emulsifiers, chelating agents, color retarders, solvents and buffers. Examples of the foregoing agents may be found in the International Cosmetic Ingredient Dictionary and Handbook, Tenth Ed., 2004 (herein incorporated by reference in its entirety). Examples of surfactants include, but are not limited to, oleth 5, oleic acid, and sodium lauryl sulfate.

Examples of thickeners include, but are not limited to, fatty alcohols (e.g., oleyl alcohol), ethoxylated phenols (e.g., octoxynol-1, nonoxynol-4, and nonoxynol-9), and polymers (e.g., hydroxyethylcellulose).

Examples of emulsifiers include, but are not limited to, Pluracare L64™ and Inconam 30™.

An example of a chelating agent includes, but is not limited to, EDTA.

Examples of solvents include, but are not limited to, buffer, water, $C_1$-$C_4$ lower alcohols (e.g., ethanol, 2-propanol and isopropanol), acetone, methylethylcetone, ethyl acetate, methyl acetate, butyl acetate, diethoxyethane, dimethoxyethane, $C_1$-$C_{10}$ alkyl, dimethyl isosorbide, ethoxydiglycol, propylene glycol, dimethylsulfoxide, and a mixture thereof. In some embodiments, the solvent is benign. In some embodiments, the solvent is not an organic solvent. In some embodiments, the solvent comprises water. In some embodiments, the solvent is water.

In some embodiments of the methods disclosed herein, the pH of the mixture is about 0.1 to about 14. In some embodiments of the methods disclosed herein, the pH of the additive composition is about 0.1 to about 14. In some embodiments, the pH of the mixture is about 1 to about 13. In some embodiments, the pH of the mixture or of the additive composition is about 5 to about 14. In some embodiments, the pH of the mixture or of the additive composition is selected from the group consisting of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, and about 14.0. In some embodiments, the pH of the mixture or of the additive composition is about 7 to about 14. In some embodiments, the pH of the mixture or of the additive composition is about 8 to about 13. In some embodiments, the pH of the mixture or of the additive composition is about 10 to about 11.

In some embodiments of the methods disclosed herein, the pH of the mixture is about 0.1 to about 6. In some embodiments of the methods disclosed herein, the pH of the additive composition is about 0.1 to about 6. In some embodiments, the pH of the mixture or of the additive composition is selected from the group consisting of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, and about 6.0. In some embodiments, the pH of the mixture or of the additive composition is about 1 to about 5. In some embodiments, the pH of the mixture or of the additive composition is about 1 to about 4.

In some embodiments of the methods disclosed herein, the mixture is applied for about 30 seconds to about 180 minutes. In some embodiments, the mixture is applied for a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, the mixture is applied for about 30 seconds to about 60 minutes. In some embodiments, the mixture is applied for about 1 minute to about 45 minutes. In some embodiments, the mixture is applied for about 15 minutes to about 45 minutes. In some embodiments, the mixture is applied for about 30 minutes. In some embodiments, the mixture is applied for about 25 minutes.

In some embodiments of the methods disclosed herein, each additive is applied for about 30 seconds to about 180 minutes. In some embodiments, each additive is applied for a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, and about 180 minutes. In some embodiments, each additive is applied for about 30 seconds to about 60 minutes. In some embodiments, each additive is applied for about 1 minute to about 45 minutes. In some embodiments, each additive is applied for about 15 minutes to about 45 minutes. In some embodiments, each additive is applied for about 30 minutes. In some embodiments, each additive is applied for about 5 minutes to about 30 minutes In some embodiments, each additive is applied for about 15 minutes.

In some embodiments, the mixture is applied to the treated hair sample within about 30 minutes after applying the additive to the hair sample. In some embodiments, the mixture is applied to the treated hair sample within about 30 minutes after applying the first additive to the hair sample. In some embodiments, the mixture is applied to the treated hair sample within a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, and about 30 minutes after applying the additive or after applying the first additive to the hair sample. In some embodiments, the mixture is applied to the treated hair sample within about 15 minutes after applying the additive to the hair sample. In some embodiments, the mixture is applied to the treated hair sample within about 15 minutes after applying the first additive to the hair sample. In some embodiments, the mixture is applied to the treated hair sample within about 10 minutes after applying the additive to the hair sample. In some embodiments, the mixture is applied to the treated hair sample within about 10 minutes after applying the first additive to the hair sample. In some embodiments, the mixture is applied to the treated hair sample within about 5 minutes after applying the additive to the hair sample. In some embodiments, the mixture is applied to the treated hair sample within about 5 minutes after applying the first additive to the hair sample. In some embodiments, the mixture is applied to the treated hair sample within about 1 minute after applying the additive to the hair sample. In some embodiments, the mixture is applied to the treated hair sample within about 1 minute after applying the first additive to the hair sample.

In some embodiments, the additive is applied to the color-treated hair sample within about 30 minutes after applying the mixture to the hair sample. In some embodiments, the first additive is applied to the color-treated hair sample within about 30 minutes after applying the mixture to the hair sample. In some embodiments, the second additive is applied to the color-treated hair sample within about 30 minutes after applying the mixture to the hair sample. In some embodiments, the third additive is applied to the color-treated hair sample within about 30 minutes after applying the mixture to the hair sample. In some embodiments, the additive, the first additive, the second additive, or the third additive is applied to the color-treated hair sample within a period of time selected from the group consisting of about 30 seconds, about 45 seconds, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, and about 30 minutes after applying the mixture to the hair sample. In some embodiments, the additive is applied to the color-treated hair sample within about 15 minutes after applying the mixture to the hair sample. In some embodiments, the first additive is applied to the color-treated hair sample within about 15 minutes after applying the mixture to the hair sample. In some embodiments, the second additive is applied to the color-treated hair sample within about 15 minutes after applying the mixture to the hair sample. In some embodiments, the third additive is applied to the color-treated hair sample within about 15 minutes after applying the mixture to the hair sample. In some embodiments, the additive is applied to the color-treated hair sample within about 10 minutes after applying the mixture to the hair sample. In some embodiments, the first additive is applied to the color-treated hair sample within about 10 minutes after applying the mixture to the hair sample. In some embodiments, the second additive is applied to the color-treated hair sample within about 10 minutes after applying the mixture to the hair sample. In some embodiments, the third additive is applied to the color-treated hair sample within about 10 minutes after applying the mixture to the hair sample. In some embodiments, the additive is applied to the color-treated hair sample within about 5 minutes after applying the mixture to the hair sample. In some embodiments, the first additive is applied to the color-treated hair sample within about 5 minutes after applying the mixture to the hair sample. In some embodiments, the second additive is applied to the color-treated hair sample within about 5 minutes after applying the mixture to the hair sample. In some embodiments, the third additive is applied to the color-treated hair sample within about 5 minutes after applying the mixture to the hair sample. In some embodiments, the additive is applied to the color-treated hair sample within about 1 minute after applying the mixture to the hair sample. In some embodiments, the first additive is applied to the color-treated hair sample within about 1 minute after applying the mixture to the hair sample. In some embodiments, the second additive is applied to the color-treated hair sample within about 1 minute after applying the mixture to the hair sample. In some embodiments, the third additive is applied to the color-treated hair sample within about 1 minute after applying the mixture to the hair sample.

In some embodiments of the methods disclosed herein, the method further comprises one or more of the following steps:

1) rinsing the hair;
2) washing the hair; and
3) drying the hair.

Exemplary Properties of a Keratin-Containing Material

In some embodiments, hair is damaged by coloring hair. In some embodiments, hair is also damaged in response to one or more stresses selected from the group consisting of washing, drying, brushing, combing, rubbing, styling, bleaching, sun exposure, heat treatment, and chemical services. For example, hair chemical services include permanent waving (perming), straightening, relaxing, and smoothing.

In some embodiments of the methods disclosed herein, the additive is selected from the group consisting of one or more antioxidants, one or more amino acids, one or more amino acid derivatives, one or more acidifiers, one or more polycarboxylic acids, one or more fatty acids, one or more fatty alcohols, one or more fatty acid esters, one or more peptides, one or more thiol compounds, one or more monomers, one or more catalysts, and a mixture thereof. In some embodiments of the methods disclosed herein, the additive comprises one or more antioxidants. In some embodiments, the additive comprises one or more amino acids, one or more amino acid derivatives, or one or more peptides. In some embodiments, the additive comprises one or more thiol compounds. In some embodiments, the additive comprises one or more monomers. In some embodiments, the additive comprises one or more catalysts. In some embodiments, the additive comprises one or more thiol compounds and one or more catalysts. In some embodiments, the additive comprises one or more monomers and one or more catalysts.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample; and
ii) applying to the hair sample for a period of time a mixture, comprising one or more hair dyes and an additive in a concentration of about 0.1% by weight to about 15% by weight;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample; and
ii) applying to the hair sample for a period of time a composition comprising one or more hair dyes and an additive in a concentration of about 0.1% by weight to about 15% by weight of the total weight of the composition, thereby producing a color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample; and
ii) applying to the hair sample for a period of time a hair composition comprising a mixture of a hair dye, alpha lipoic acid, and at least one amino acid or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, N-acetyl alanine, and N-acetyl L-cysteine or a combination thereof, wherein the total concentration of the alpha lipoic acid and the at least one amino acid or the at least one N-acetyl amino acid is about 0.1% by weight to about 15% (e.g., about 0.1% by weight to about 10%) by weight of the total weight of the hair composition, thereby producing a color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying an additive in a concentration of about 0.1% by weight to about 15% by weight to the hair sample for a period of time, thereby producing a treated hair sample; and
iii) applying to the treated hair sample a mixture, comprising one or more hair dyes;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a composition comprising an additive in a concentration of about 0.1% by weight to about 15% by weight of the total weight of the composition to the hair sample for a period of time, thereby producing a treated hair sample; and iii) applying to the treated hair sample a mixture, comprising one or more hair dyes, thereby producing a color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying a composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanineor a combination thereof, wherein the total concentration of the N-acetyl-L-Cysteine and the at least one amino acid and/or the at least N-acetyl amino acid is about 0.1% by weight to about 15% (e.g., about 0.1% by weight to about 10%) by weight of the total weight of the second hair composition to the hair sample for a period of time, thereby producing a treated hair sample; and iii) applying to the treated hair sample a mixture, comprising one or more hair dyes, thereby producing a color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying to the hair sample for a period of time a mixture, comprising one or more hair dyes, thereby producing a color-treated hair sample; and iii) applying an additive in a concentration of about 0.1% by weight to about 15% by weight to the color-treated hair sample;

thereby improving the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying to the hair sample for a period of time a mixture, comprising one or more hair dyes, thereby producing a color-treated hair sample; and iii) applying a composition comprising an additive in a concentration of about 0.1% by weight to about 15% by weight of the total weight of the composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample; and ii) applying to the hair sample for a period of time a first hair composition comprising a hair dye, thereby producing a color-treated hair sample; and iii) applying to the hair a second hair composition comprising gluconolactone and citric acid and at least one amino acid and/or at least one N-acetyl amino acid selected from glycine, alanine, serine, proline, tyrosine, arginine, lysine, aspartic acid, glutamic acid, tryptophan, and N-acetyl glycine, N-acetyl serine, N-acetyl alanine, and N-acetyl-L-Cysteine, or a combination thereof, wherein the total concentration of gluconolactone, citric acid and the at least one amino acid and/or the at least one N-acetyl amino acid is about 0.1% by weight to about 15% (e.g., about 0.1% by weight to about 10%) by weight of the total weight of the second hair composition, thereby producing a color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying a first additive in a concentration of about 0.1% by weight to about 15% by weight to the hair sample for a period of time, thereby producing a treated hair sample; and iii) applying to the treated hair sample for a period of time a mixture, comprising one or more hair dyes and a second additive in a concentration of about 0.1% by weight to about 15% by weight, thereby producing a color-treated hair sample;

thereby improving the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a first composition comprising a first additive in a concentration of about 0.1% by weight to about 15% by weight of the total weight of the first composition to the hair sample for a period of time, thereby producing a treated hair sample; and
iii) applying to the treated hair sample for a period of time a second composition comprising one or more hair dyes and a second additive in a concentration of about 0.1% by weight to about 15% by weight of the total weight of the second composition, thereby producing a color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a first composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the N-acetyl-L-Cysteine and the at least one amino acid and/or the at least one N-acetyl amino acid is about 0.1% by weight to about 15% (e.g., about 0.1% by weight to about 10%) by weight of the total weight of the first composition to the hair sample for a period of time, thereby producing a treated hair sample; and
iii) applying to the treated hair sample for a period of time a second composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, and tryptophan, pyrrolidone carboxylic acid, N-acetyl glycine, N-acetyl serine, and N-acetyl alanine, or a combination thereof, wherein the total concentration of the alpha lipoic acid and amino acid is about 0.1% by weight to about 10% by weight of the total weight of the second composition, thereby producing a color-treated hair sample.

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a first additive in a concentration of about 0.1% by weight to about 15% by weight to the hair sample for a period of time, thereby producing a treated hair sample;
iii) applying to the treated hair sample for a period of time a mixture, comprising one or more hair dyes, thereby producing a color-treated hair sample; and
iv) applying a second additive in a concentration of about 0.1% by weight to about 15% by weight to the color-treated hair sample;

thereby improving the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a first composition comprising a first additive in a concentration of about 0.1% by weight to about 15% by weight of the total weight of the first composition to the hair sample for a period of time, thereby producing a treated hair sample;
iii) applying to the treated hair sample for a period of time a mixture, comprising one or more hair dyes, thereby producing a color-treated hair sample; and
iv) applying a second composition comprising a second additive in a concentration of about 0.1% by weight to about 15% by weight of the total weight of the second composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;
ii) applying a first composition comprising N-acetyl-L-Cysteine and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the N-acetyl-L-Cysteine and the at least one amino acid and/or the at least one N-acetyl amino acid is about 0.1% by weight to about 15% (e.g., about 0.1% by weight to about 10%) by weight of the total weight of the first composition to the hair sample for a period of time, thereby producing a treated hair sample;

iii) applying to the treated hair sample for a period of time a mixture, comprising one or more hair dyes, thereby producing a color-treated hair sample; and iv) applying a second composition comprising gluconolactone, citric acid and at least one amino acid and/or at least one N-acetyl amino acid selected from glycine, alanine, serine, proline, tyrosine, arginine, lysine, aspartic acid, glutamic acid, tryptophan, and N-acetyl glycine, N-acetyl serine, N-acetyl alanine, and N-acetyl-L-Cysteine or a combination thereof, wherein the total concentration of the gluconolactone, citric acid and the at least one amino acid and/or the at least one N-acetyl amino acid is about 0.1% by weight to about 15% (e.g., about 0.1% by weight to about 10%) by weight of the total weight of the second composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying to the hair sample for a period of time a mixture, comprising one or more hair dyes and a first additive in a concentration of about 0.1% by weight to about 15% by weight, thereby producing a color-treated hair sample; and iii) applying a second additive in a concentration of about 0.1% by weight to about 15% by weight to the color-treated hair sample;

thereby improving the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying to the hair sample for a period of time a first composition comprising one or more hair dyes and a first additive in a concentration of about 0.1% by weight to about 15% by weight of the total weight of the first composition, thereby producing a color-treated hair sample; and iii) applying a second composition comprising a second additive in a concentration of about 0.1% by weight to about 15% by weight of the total weight of the second composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying to the hair sample for a period of time a first composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the alpha lipoic acid and the at least one amino acid and/or the at least one N-acetyl amino acid is about 0.1% by weight to about 15% (e.g., about 0.1% by weight to about 10%) by weight of the total weight of the first composition, thereby producing a color-treated hair sample; and iii) applying a second composition comprising gluconolactone, citric acid and at least one amino acid and/or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine, and N-acetyl-L-Cysteine or a combination thereof, wherein the total concentration of the gluconolactone, citric acid and the at least one amino acid and/or at least one N-acetyl amino acid is about 0.1% by weight to about 15% (e.g., about 0.1% by weight to about 10%) by weight of the total weight of the second composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying a first additive in a concentration of about 0.1% by weight to about 15% by weight to the hair sample for a period of time, thereby producing a treated hair sample;

iii) applying to the treated hair sample for a period of time a mixture, comprising one or more hair dyes and a second additive in a concentration of about 0.1% by weight to about 15% by weight, thereby producing a color-treated hair sample; and iv) applying a third additive in a concentration of about 0.1% by weight to about 15% by weight to the color-treated hair sample;

thereby improving the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying a first composition comprising a first additive in a concentration of about 0.1% by weight to about 15% by weight of the total weight of the composition to the hair sample for a period of time, thereby producing a treated hair sample;

iii) applying to the treated hair sample for a period of time a second composition comprising one or more hair dyes and a second additive in a concentration of about 0.1% by weight to about 15% by weight of the total weight of the second composition, thereby producing a color-treated hair sample; and iv) applying a third composition comprising a third additive in a concentration of about 0.1% by weight to about 15% by weight of the total weight of the third composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In another aspect, the disclosure provides a method for coloring hair, wherein one or more properties selected from the group consisting of a hydrophobicity, an elongation at break, a Young's modulus, an ultimate tensile strength, a protein loss value, a denaturation temperature, and a color retention of the color-treated hair sample are improved, comprising:

i) providing a hair sample;

ii) applying a first composition comprising N-acetyl-L-Cysteine and at least one amino acid and/or at least one N-acetyl amino acid at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the N-acetyl-L-Cysteine and the at least one amino acid and/or at least one N-acetyl amino acid is about 0.1% by weight to about 15% (e.g., about 0.1% by weight to about 10%) by weight of the total weight of the first composition to the hair sample for a period of time, thereby producing a treated hair sample;

iii) applying to the treated hair sample for a period of time a second composition comprising one or more hair dyes, alpha lipoic acid and at least one amino acid and/or at least one N-acetyl amino acid selected from glycine, alanine, serine, proline, tyrosine, arginine, lysine, aspartic acid, glutamic acid, tryptophan, pyrrolidone carboxylic acid, N-acetyl glycine, N-acetyl serine, and N-acetyl alanine, or a combination thereof, wherein the total concentration of the alpha lipoic acid and the at least one amino acid and/or the at least one N-acetyl amino acid is about 0.1% by weight to about 15% (e.g., about 0.1% by weight to about 10%) by weight of the total weight of the second composition, thereby producing a color-treated hair sample; and iv) applying a third composition comprising gluconolactone, citric acid and at least one amino acid and/or at least one N-acetyl amino acid selected from glycine, alanine, serine, proline, tyrosine, arginine, lysine, aspartic acid, glutamic acid, tryptophan, N-acetyl glycine, N-acetyl serine, N-acetyl alanine, and N-acetyl-L-Cysteine, or a combination thereof, wherein the total concentration of gluconolactone, citric acid and the at least one amino acid and/or the at least one N-acetyl amino acid is about 0.1% by weight to about 15% (e.g., about 0.1% by weight to about 10%) by weight of the total weight of the third composition to the color-treated hair sample;

thereby improving one or more properties selected from the group consisting of the hydrophobicity, the elongation at break, the Young's modulus, the ultimate tensile strength, the protein loss value, the denaturation temperature, and the color retention of the color-treated hair sample.

In some embodiments of the methods disclosed herein, the method for coloring hair improves one or more properties selected from the group consisting of a hydrophobicity, an elongation at break, a Young's modulus, an ultimate tensile strength, a protein loss value, a denaturation temperature, and a color retention of the color-treated hair sample.

In some embodiments, the hydrophobicity of color-treated hair sample is used to evaluate improvement in hair properties. In general, an advancing water contact angle greater than about 90° the surface is considered hydrophobic. In some embodiments, the advancing water contact angle is greater than about 70°. In some embodiments, the advancing water contact angle is greater than about 80°. In some embodiments, the advancing water contact angle is greater than about 90°. In some embodiments, the advancing water contact angle is greater than about 100°.

In some embodiments, the advancing water contact angle is selected from the group consisting of about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89°, about 90°, about 91°, about 92°, about 93°, about 94°, about 95°, about 96°, about 97°, about 98°, about 99°, about 100°, about 101°, about 102°, about 103°, about 104°, about 105°, about 106°, about 107°, about 108°, about 109°, and about 110°. In some embodiments, the advancing water contact angle is about 100°.

In some embodiments, the elongation at break of the color-treated hair sample is used to evaluate the strength of the hair. Stronger materials can withstand more stress and strain. Stronger materials can be elongated further before breaking.

In some embodiments, the Young's modulus of the color-treated hair sample is used to evaluate the strength of the hair. The Young's modulus (or modulus of elasticity) is a measure of the ability of a material to withstand changes in length when under lengthwise tension or compression. Young's modulus is equal to the longitudinal stress divided by the strain.

In some embodiments, the ultimate tensile strength of the color-treated hair sample is used to evaluate the structural integrity of the material. Ultimate tensile strength is the capacity of a material to withstand loads tending to elongate the material.

In some embodiments, the protein loss value of the color-treated hair sample is used to evaluate the strength and the structural integrity of the material. For example, after chemical treatments such as dyeing, bleaching, perming, or straightening, hair becomes damaged, which results in higher protein loss. A higher protein loss value is correlated with more damage and less structural integrity.

In some embodiments, the denaturation temperature of the color-treated hair sample is used to evaluate the strength and the structural integrity of the material. For example, after chemical treatments such as dyeing, bleaching, perming, or straightening, hair becomes damaged. Damaged materials are correlated with decreased denaturation temperatures.

In some embodiments, the color retention of the color-treated hair sample is used to evaluate improvement in hair properties. Color retention is evaluated over multiple shampoo cycles to simulate the number of shampoos during 4-6 weeks after a consumer has dyed his or her hair. Color retention can be evaluated qualitatively by eye and quantitatively using a colorimeter.

In some embodiments of the methods disclosed herein, the color-treated hair sample is evaluated by "sensory evaluation". As used herein, "sensory evaluation" refers to comparative sensory evaluations of color-treated hair samples by people. These people have been trained in sensory evaluations to evaluate tactile (e.g., manageability, smoothness, conditioned feeling) and visual properties (e.g., color, frizz, fiber alignment, and curl shape) of the samples. The evaluation is often side-by-side, that is, comparison of a color-treated hair sample with an untreated or control color-treated hair sample. In some embodiments, the sensory evaluation is blinded. That is, the evaluator does not know the treatment status of the samples before the evaluation. In some embodiments, the results of the sensory evaluation are categorized as nothing, moderately conditioned, or very product-y. In In some embodiments, the results of the sensory evaluation are presented as "sensory scores". Typically, color-treated hair samples as well as an untreated or control color-treated hair samples are prepared in duplicate, blinded randomly, and evaluated for visual, tactile and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes. In some embodiments, the color-treated hair sample mimics virgin hair. In some embodiments, the color-treated hair sample has similar characteristics to virgin hair.

In some embodiments, the color-treated hair sample with additive provides wash-resistant color retention. In some embodiments, the color-treated hair has improved alignment. In some embodiments, the color-treated hair has long-lasting smoothness. In some embodiments, the color-treated hair has improved shine. For example, properties of color-treated hair with additives can be assessed based on one or more of a hydrophobicity, an elongation at break, a Young's modulus, an ultimate tensile strength, a protein loss value, a denaturation temperature, and a color retention.

In some embodiments, the hair treatment provides a wash-resistant functional (i.e. hydrophobic) layer in addition to improved color retention. In some embodiments, the treated hair has improved alignment. In some embodiments, the treated hair has long-lasting smoothness. In some embodiments, the treated hair has improved shine. For example, hair health can be assessed based on one or more of an elongation at break, a Young's modulus, an ultimate tensile strength, a protein loss value, and a denaturation temperature.

Exemplary Kits

One aspect of the disclosure provides a kit comprising i) an additive composition comprising one or more additives; and ii) instructions for use.

One aspect of the disclosure provides a kit comprising i) a hair dye composition comprising one or more hair dyes; ii) an additive composition comprising one or more additives; and iii) instructions for use.

In some embodiments, the kit comprises i) a hair dye composition comprising a plurality of oxidative dye precursors; ii) an additive composition comprising one or more additives; and iii) instructions for use.

One aspect of the disclosure provides a kit comprising i) a first additive composition comprising one or more additives; ii) a second additive composition comprising one or more additives; and iii) instructions for use.

One aspect of the disclosure provides a kit comprising i) a hair dye composition comprising one or more hair dyes; ii) a first additive composition comprising one or more additives; iii) a second additive composition comprising one or more additives; and iv) instructions for use.

In some embodiments, the kit comprises i) a hair dye composition comprising a plurality of oxidative dye precursors; ii) a first additive composition comprising one or more additives; iii) a second additive composition comprising one or more additives; and iv) instructions for use.

One aspect of the disclosure provides a kit comprising i) a first additive composition comprising one or more additives; ii) a second additive composition comprising one or more additives; iii) a third additive composition comprising one or more additives; and iv) instructions for use.

One aspect of the disclosure provides a kit comprising i) a hair dye composition comprising one or more hair dyes; ii) a first additive composition comprising one or more additives; iii) a second additive composition comprising one or more additives; iv) a third additive composition comprising one or more additives; and v) instructions for use.

In some embodiments, the kit comprises i) a hair dye composition comprising a plurality of oxidative dye precursors; ii) a first additive composition comprising one or more additives; iii) a second additive composition comprising one or more additives; iv) a third additive composition comprising one or more additives; and v) instructions for use.

In some embodiments, the kit further comprises a) an oxidizing agent composition comprising an oxidizing agent. In some embodiments, the oxidizing agent is separate from the other components.

In some embodiments, each additive composition comprises one or more additives; and a solvent. In some embodiments, the additive composition comprises one or more additives; and a solvent. In some embodiments, the first additive composition comprises one or more additives; and a solvent. In some embodiments, the second additive composition comprises one or more additives; and a solvent. In some embodiments, the third additive composition comprises one or more additives; and a solvent. In some embodiments of the kits disclosed herein, the additive is in a concentration of about 0.1% by weight to about 15% by weight. In some embodiments of the kits disclosed herein, each additive is in a concentration of about 0.1% by weight to about 15% by weight. In some embodiments of the kits disclosed herein, the first additive is in a concentration of about 0.1% by weight to about 15% by weight. In some embodiments of the kits disclosed herein, the second additive is in a concentration of about 0.1% by weight to about 15% by weight. In some embodiments of the kits disclosed herein, the third additive is in a concentration of about 0.1% by weight to about 15% by weight.

In some embodiments, each additive is independently selected from the group consisting of one or more antioxidants, one or more amino acids, one or more amino acid derivatives, one or more acidifiers, one or more polycarboxylic acids, one or more fatty acids, one or more fatty alcohols, one or more fatty acid esters, one or more peptides, one or more thiol compounds, one or more monomers, one or more catalysts, and a mixture thereof.

In some embodiments, the hair dye composition comprises one or more hair dyes; and a solvent. In some embodiments, the hair dye composition comprises one or more oxidative dye precursors; and a solvent.

In some embodiments of the kits disclosed herein, the concentration of the one or more hair dyes or of the one or more oxidative dye precursors is about 0.01% by weight to about 15% by weight.

In some embodiments, the solvent comprises dimethyl sulfoxide, water, $C_1$-$C_4$ lower alcohols (e.g., ethanol, 2-propanol and isopropanol), acetone, methylethylcetone, ethyl acetate, methyl acetate, butyl acetate, diethoxyethane, dimethoxyethane, $C_1$-$C_{10}$ alkyl, dimethyl isosorbide, ethoxydiglycol, propylene glycol, buffer, or a mixture thereof. In some embodiments, the solvent comprises water. In some embodiments, the solvent is water.

EXEMPLIFICATION

The invention now being generally described, it will be more readily understood by reference to the following, which is included merely for purposes of illustration of certain aspects and embodiments of the present invention, and is not intended to limit the invention.

Example 1—Additive During Color Treatment

Alpha-Lipoic Acid

Alpha-Lipoic Acid Concentration

A study was carried out to incorporate alpha-lipoic acid (ALA) as an additive during color treatment. Lipoic acid has been reported to exhibit strong antioxidant properties, based on its capacity to chelate metal ions (e.g., $Fe^{2+}$ and $Cu^{2+}$), ability to scavenge reactive oxygen species, and ability to repair oxidative damage. Without being bound by any theory, it is proposed that the use of an antioxidant, such as ALA, during the hair coloring process can reduce the hair damage caused by the oxidative hair dye process. As an initial screening, a L'OREAL® Paris Intense Red Copper (RR07/warmer) at-home color product comprising a color gel (comprising primary intermediates and couplers, including 2-methyl-5-hydroxy-ethylaminophenol, p-aminophenol, p-phenylenediamine, and 6-hydroxyindole) and a developer ($H_2O_2$, 20 Vol-6% by weight) was used. To study the effect of ALA concentrations, ALA concentrations in the range of 0.5 wt % to 2 wt % were tested by mixing ALA powder into a coloring mixture containing 1 g of color gel and 1 g of developer. The final color mixture had a pH of 10.5, and the addition of ALA did not affect the mixture pH. The final color mixture was mixed for 5 min, massaged thoroughly (~1 min) onto a one-time (1×) bleached hair tress (1.5 g) and kept on for 25 min for color development. FIG. 1 shows the color development on 1× bleached hair tresses at different ALA concentrations in the range of 0.5 wt % to 2 wt % compared to the tress treated with no additive. No noticeable color interference was observed for a ALA concentration up to 1 wt %.

Figure 2:
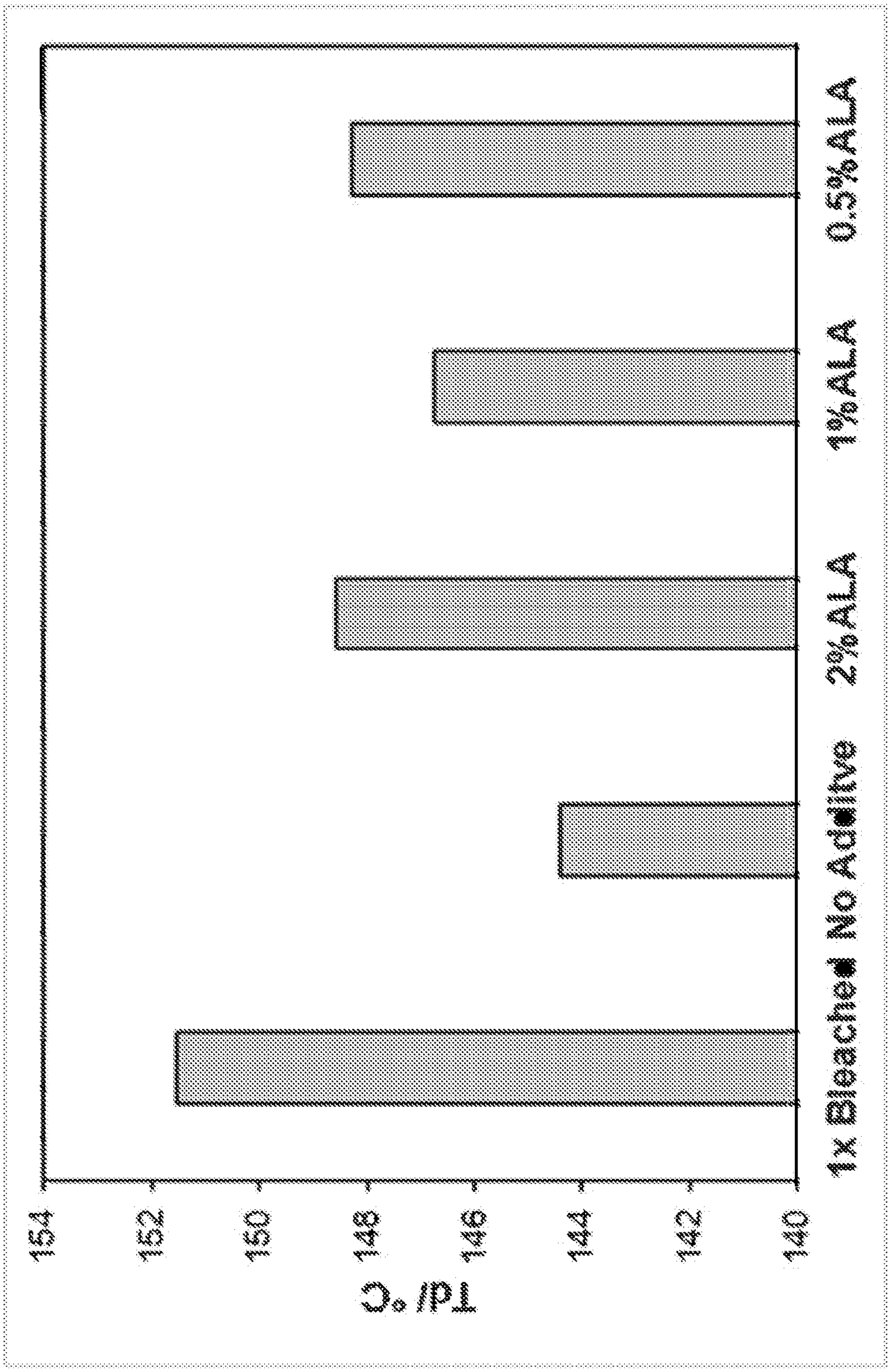
FIG. 2 depicts denaturation temperatures collected on color-treated hair tresses with alpha lipoic acid (ALA) as an additive at different concentrations compared to control with no additive.

Differential scanning calorimetry was performed on tresses to determine the effect of ALA concentration on hair denaturation temperature (Td). FIG. 2 shows denaturation temperatures collected on color-treated hair tresses with or without ALA additive. The color-treated hair tress with no additive showed ~8° C. decrease in Td after the treatment. However, when ALA was added, a 3-5° C. recovery in Td was observed. The highest Td increase was achieved by using 2 wt % ALA. The significant increase in Td values indicates improvements in hair strength by using ALA as an additive during color treatment.

Figure 3:
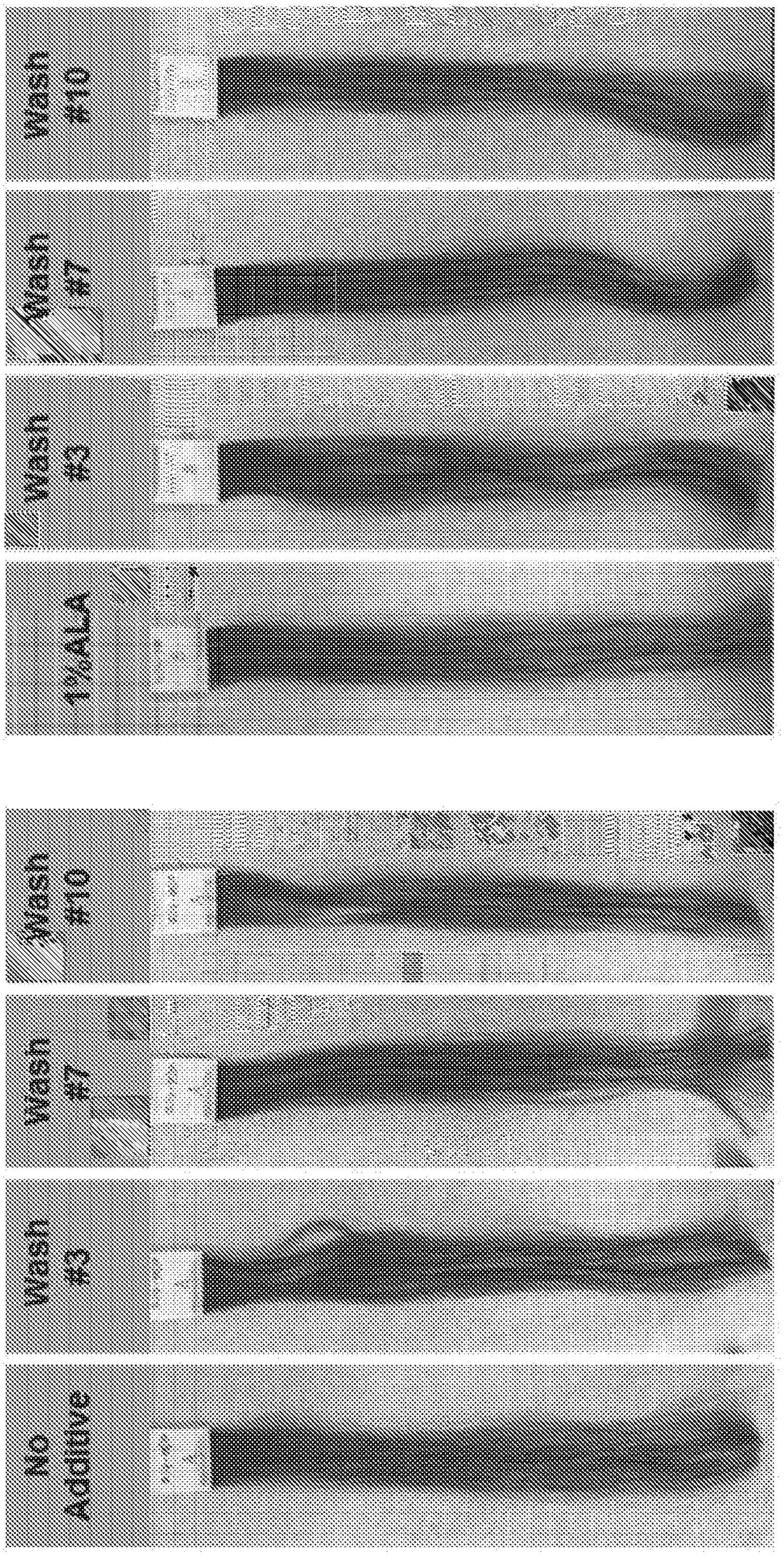
FIG. 3 depicts an image showing the color retention performance over 10 washes of color-treated hair samples in the presence of 1 wt % ALA compared to the control with no additive.

The color retention for all colored tresses was evaluated by subjecting the tresses to repetitive washing and drying cycles. The hair samples were washed with PHD shampoo and conditioner, and color changes after 3, 7 and 10 washes were evaluated. FIG. 3 shows the color-treated tress in the presence of 1 wt % ALA as compared to the control with no additive. Although both tresses became slightly lighter after 10 washes, very similar color retention was observed.

Figure 4:
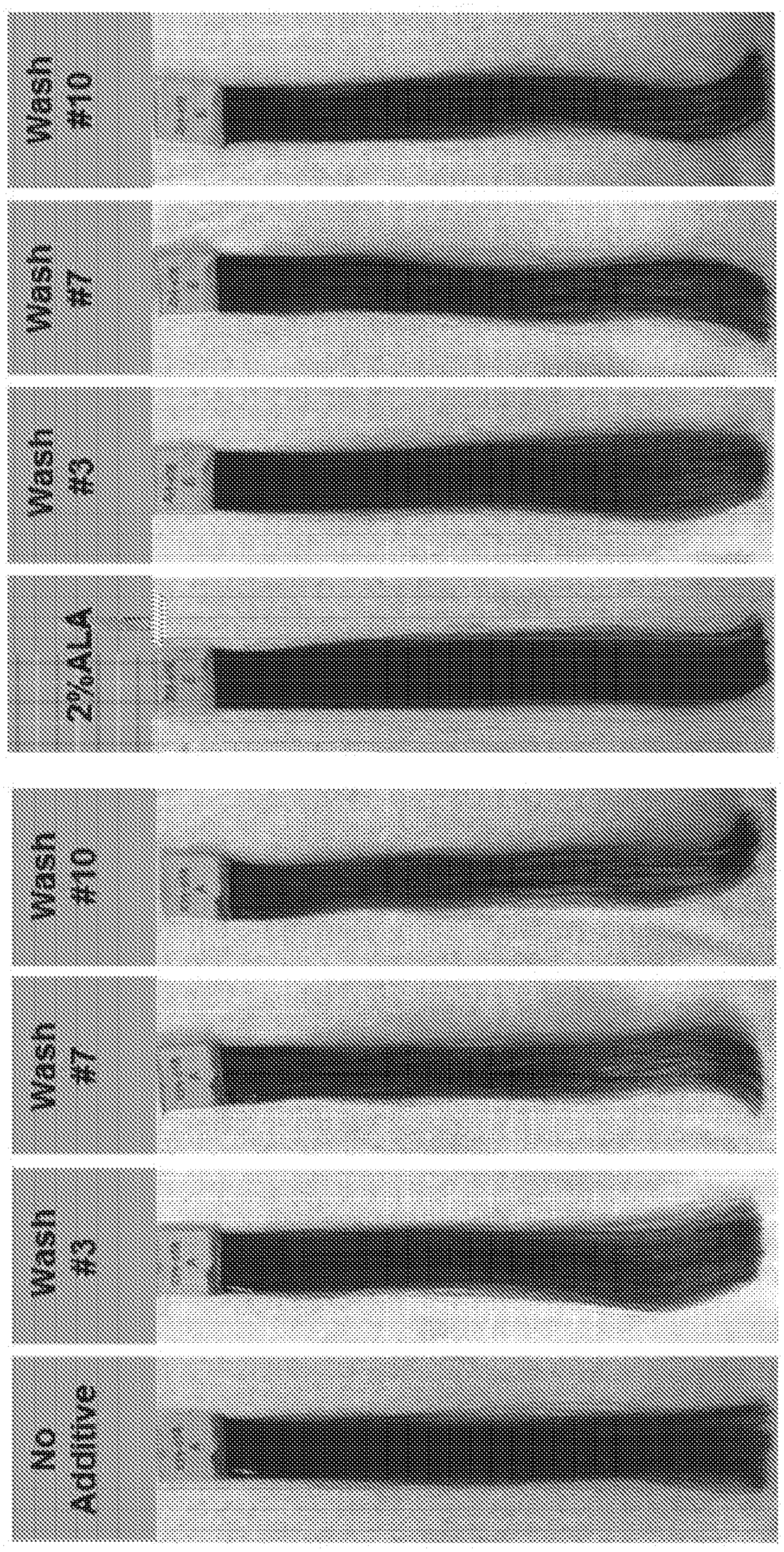
FIG. 4 depicts an image of showing the color development on 1× bleached hair tresses treated with 2 wt % ALA in the final color mixture compared to control with no additive.

Similarly, lipoic acid was also explored as an additive during salon hair color treatment. A mixture of Wella (Colortango) permanent masque (4VR-Mahogany) hair color product, which comprises hair colorants (comprising primary intermediates and couplers including 2-methyl-5-hydroxy-ethylaminophenol, 1-hydroxyethyl 4,5-diamino pyrazole sulfate, and toluene-2,5-diamine sulfate) and Wella professional's (Welloxon Perfect™) developer ($H_2O_2$, 20 Vol-6% by weight) were used as the color treatment. For preliminary testing, a 2 wt % ALA powder was directly mixed into a color mixture containing 1 g color cream and 1 g developer. The final color mixture was mixed for 5 min, massaged thoroughly (~1 min) onto a 1× bleached hair tress (1.5 g) and kept on for 30 min for color development. As shown in FIG. 4, a minimal color interference was observed when a 2 wt % ALA was used as an additive during the color treatment. Washing study also shows that color retention was improved for the color-treated hair tress with ALA additive (FIG. 4).

Figure 5:
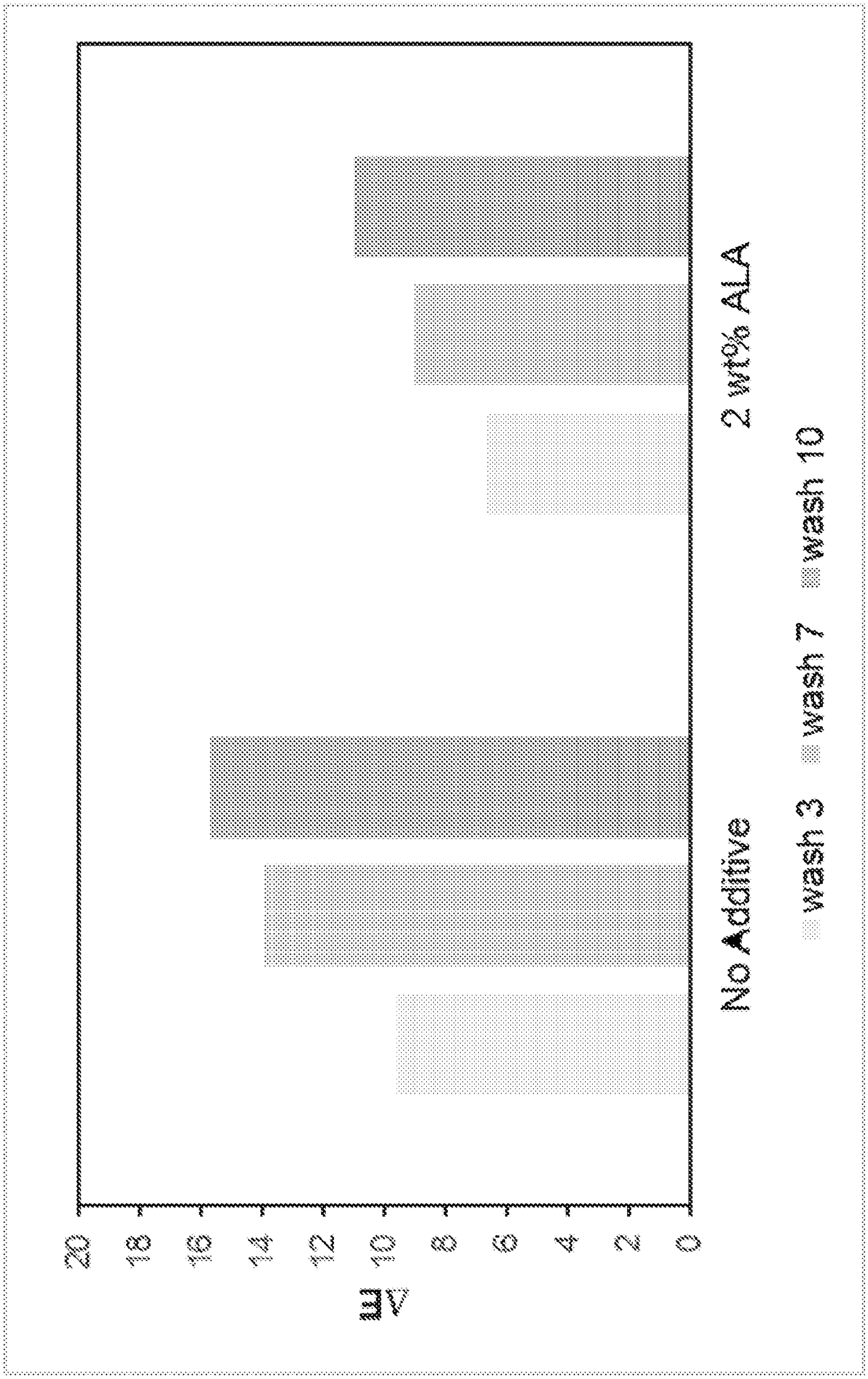
FIG. 5 depicts an image showing overall color difference (ΔE) after 3, 7 and 10 washes of color-treated hair samples with 2% ALA as an additive compared to control with no additive.

To further quantify the color changes, colorimetry analysis was performed on color-treated hair tresses with or without 2% ALA as an additive. FIG. 5 shows the total color difference (ΔE) for color-treated hair tresses with or without 2% ALA as an additive. Lower ΔE was achieved when 2 wt % ALA was used as an additive, suggesting enhanced color protection by ALA.

Figure 6:
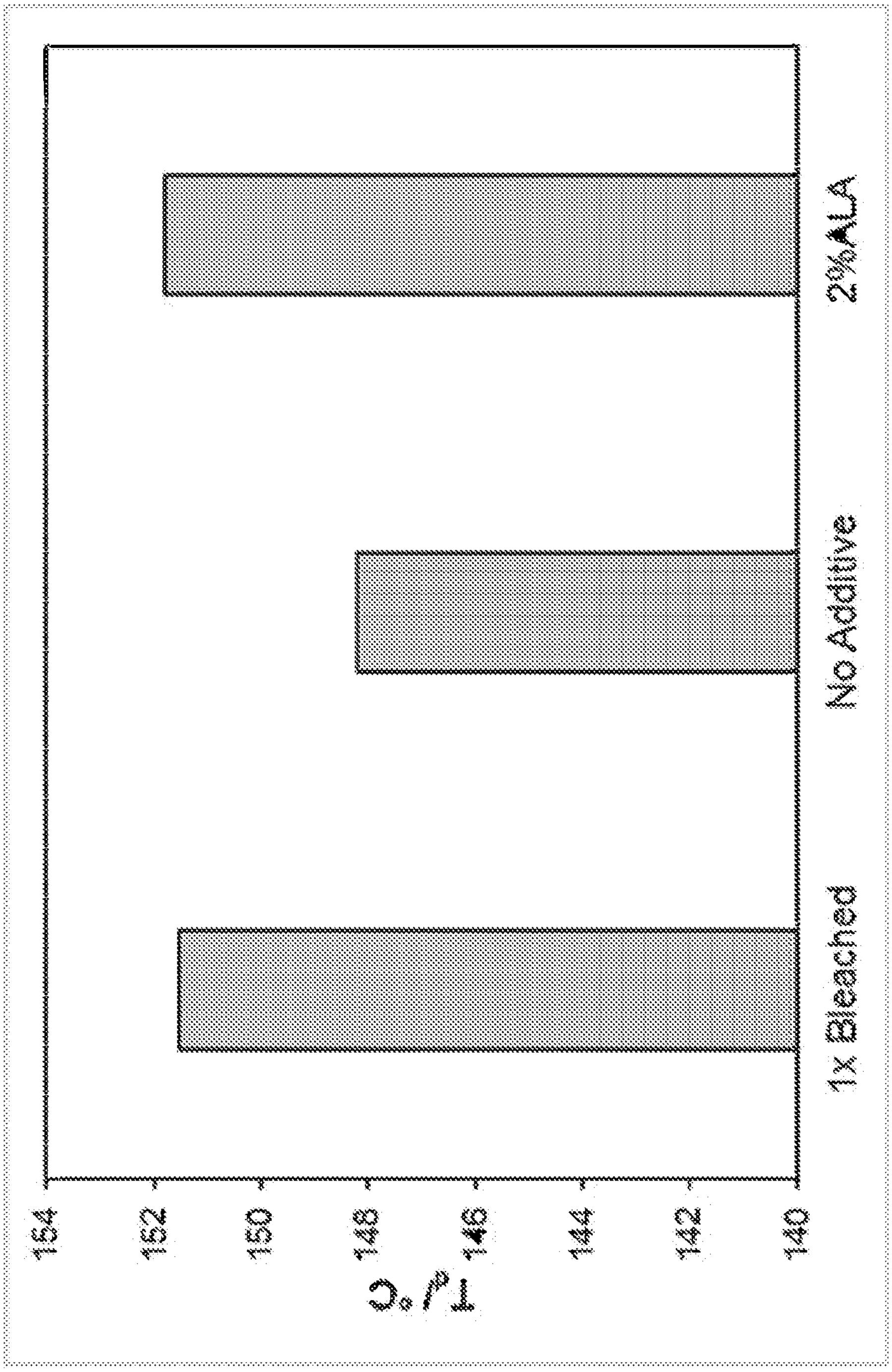
FIG. 6 depicts denaturation temperatures collected on salon color-treated hair tresses with 2 wt % ALA as an additive compared to control with no additive.

Differential scanning calorimetry shows that, when no additive was used, hair denaturation temperature decreased by 3° C. after the color treatment (FIG. 6). However, when 2 wt % ALA was used as an additive, no detectable decrease in Td was observed after the color treatment, suggesting minimal hair damage by the color treatment in the presence of ALA.

Mannequin Head Testing with ALA

Figure 7:
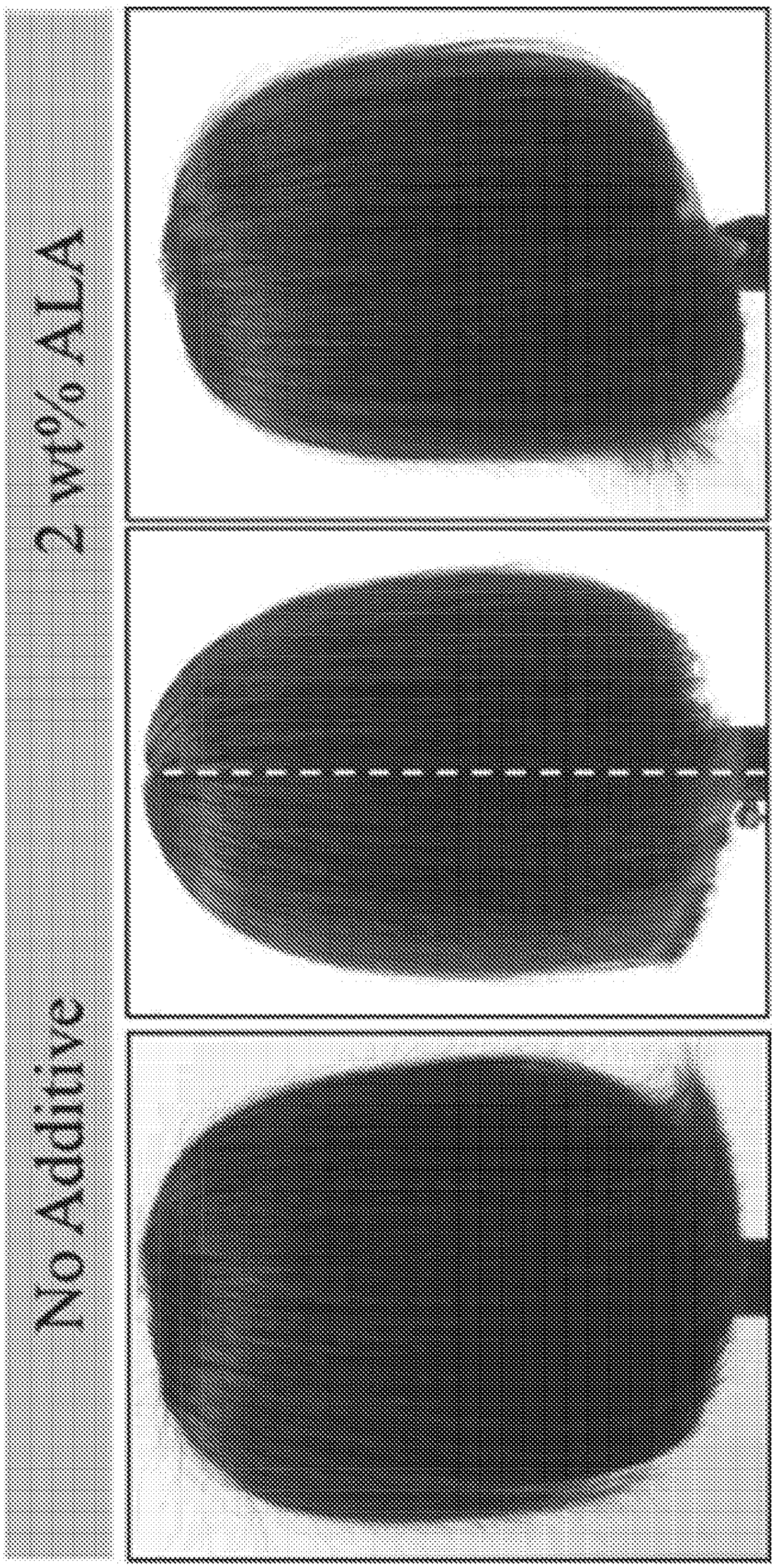
FIG. 7 depicts the image of bleached mannequin with one side color-treated with no additive (left) and on one side color-treated with 2 wt % ALA as an additive (right).

Various tests were conducted using mannequin heads to evaluate the effect of using ALA as an additive. A study on salon color treatment with 2 wt % ALA as an additive was carried out both on bleached and unbleached mannequins (MQs). MQ Hair ("Helen" Deluxe Lesson Head with 18" 100% Human hair, Medium Brown Color, Rubber Base-J6) was bleached before the treatment (Clairol Professional BW2 powder bleach 32 g. Salon Care developer ($H_2O_2$, 30 Vol-9% by weight, 48 g)) for 15 min under dryer. A mixture of Wella (Colortango) permanent masque (4VR-Mahogany)

hair color product (comprising primary intermediates and couplers including 2-methyl-5-hydroxy-ethylaminophenol, 1-hydroxyethyl 4,5-diamino pyrazole sulfate, and toluene-2,5-diamine sulfate) and Wella professional's (Welloxon Perfect™) developer ($H_2O_2$, 20 Vol-6% by weight), was used as the color treatment. In this test, one side of MQ was color treated with no additive and the other side was treated with 2 wt % ALA as an additive. A 75 g of final color mixture was used for each side, which was mixed for 5 min, massaged thoroughly onto a 1× bleached MQ and kept on for 30 min for color development followed by rinsing with water. FIG. 7 shows that the right side, which was color treated with 2 wt % ALA, appeared slightly deeper in color. Sensory evaluation by a blinded sensory and color evaluation panel shows that the right side with ALA feels smoother, shinier, and softer compared to the left side without any additive.

Figure 8:
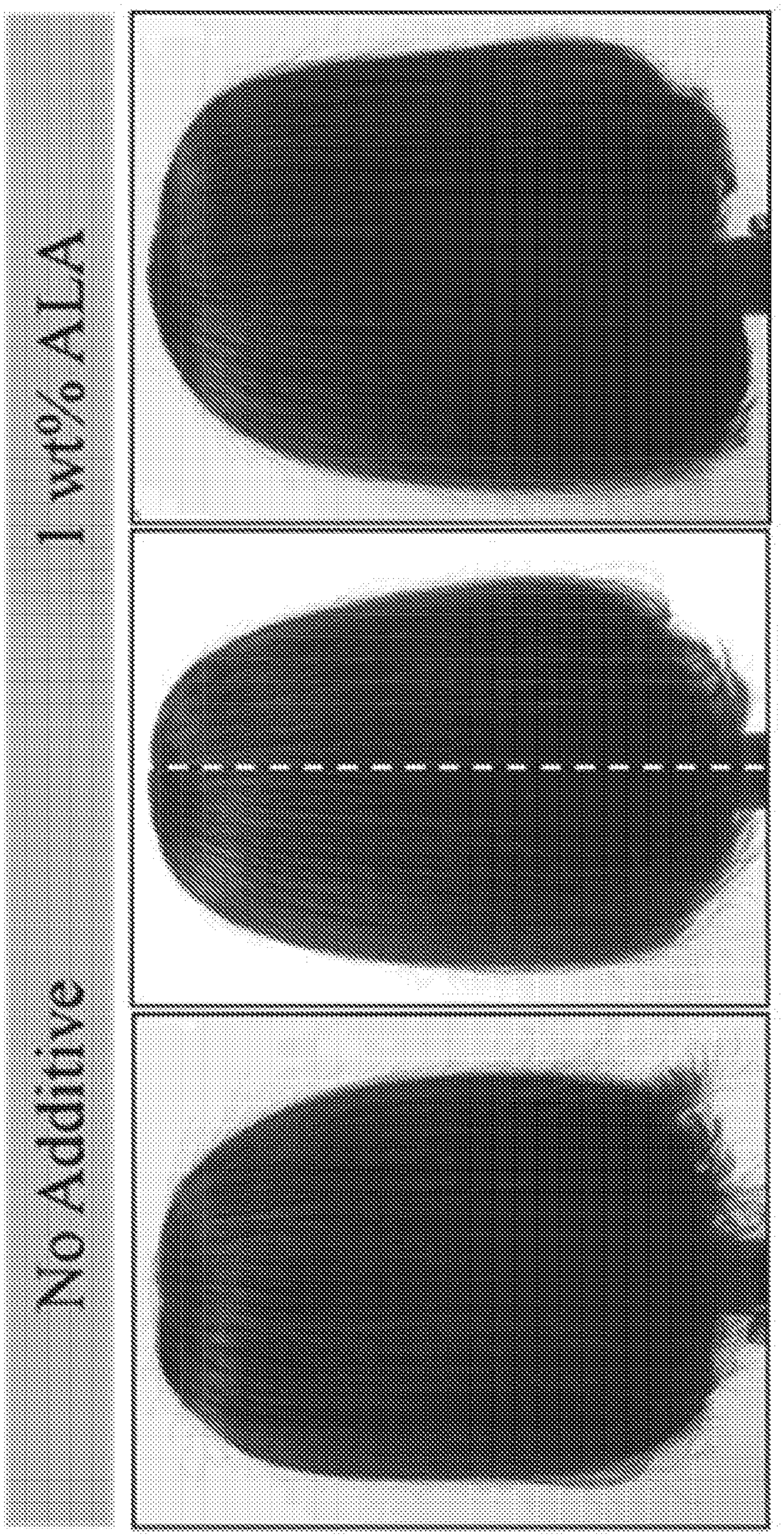
FIG. 8 depicts an image showing bleached mannequin with one side color-treated with no additive (left) and one side color-treated with 1 wt % ALA as an additive (right).

To achieve minimal color interference, another MQ study with a lower ALA concentration at 1 wt % was carried out. FIG. 8 shows that overall both sides had very similar color development. However, the left side with no additive exhibited less homogeneous color distribution. Consistent with the treatment with 2 wt % ALA, the treatment with 1 wt % ALA also showed improved sensory properties, i.e., smoother, shinier, and softer compared to the side without any additive.

Figure 9:
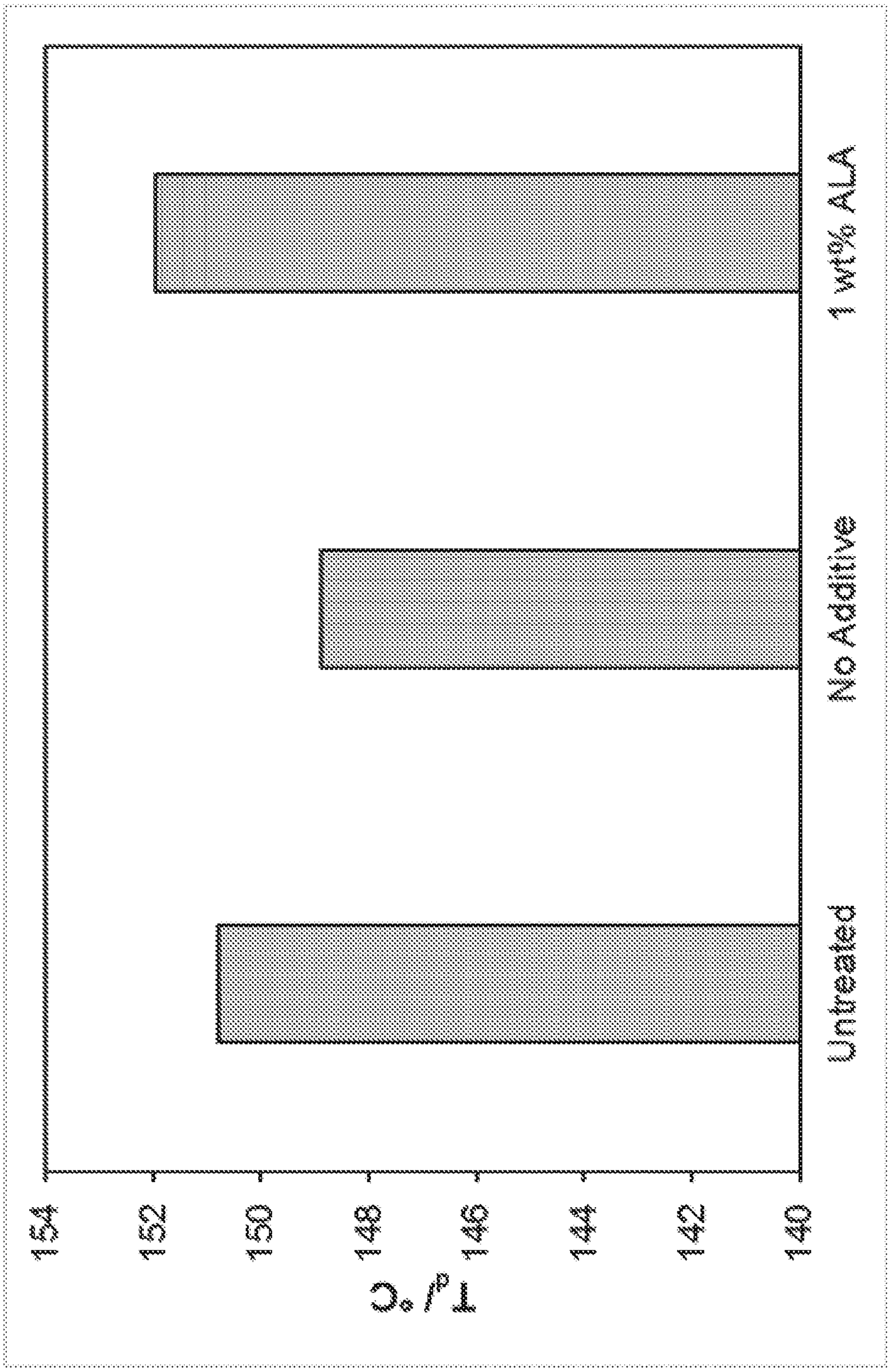
FIG. 9 depicts denaturation temperatures collected on a salon color-treated hair sample with 1 wt % ALA as additive compared to an untreated hair sample and a color-treated hair sample with no additive.

Hair denaturation temperature for both sides of the MQ was also collected. As shown in FIG. 9, the color treatment with no additive led to a 2° C. decrease in Td. By contrast, a significant increase in Td was observed for the side color treated in the presence of 1 wt % ALA. The fact that the Td became even higher than the level of the untreated hair suggests improved hair strength after the color treatment with an additive.

α-Lipoic Acid with Amino Acids as Coadditives

The incorporation of amino acids as coadditives with ALA to further improve healthy benefits was also explored. A series of amino acids was studied in a single, binary and ternary blend systems with ALA. Additionally, commercially available amino acid mixtures were also tested.

i. α-Lipoic Acid with Single Amino Acid

Studies herein focused on the amino acids most commonly known to be leached out of the hair (alanine; Ala, glycine; Gly, serine; Ser, proline; Pro), amino acids with basic side chains (arginine; Arg, lysine; Lys), acidic side chains (aspartic acid; Asp, glutamic acid; Glu), acetylated amino acids (N-acetyl glycine, N-acetyl serine, N-acetyl alanine, N-acetyl L-cysteine), and hydrophobic amino acids (tyrosine; Tyr, tryptophan; Trp).

Figure 22:
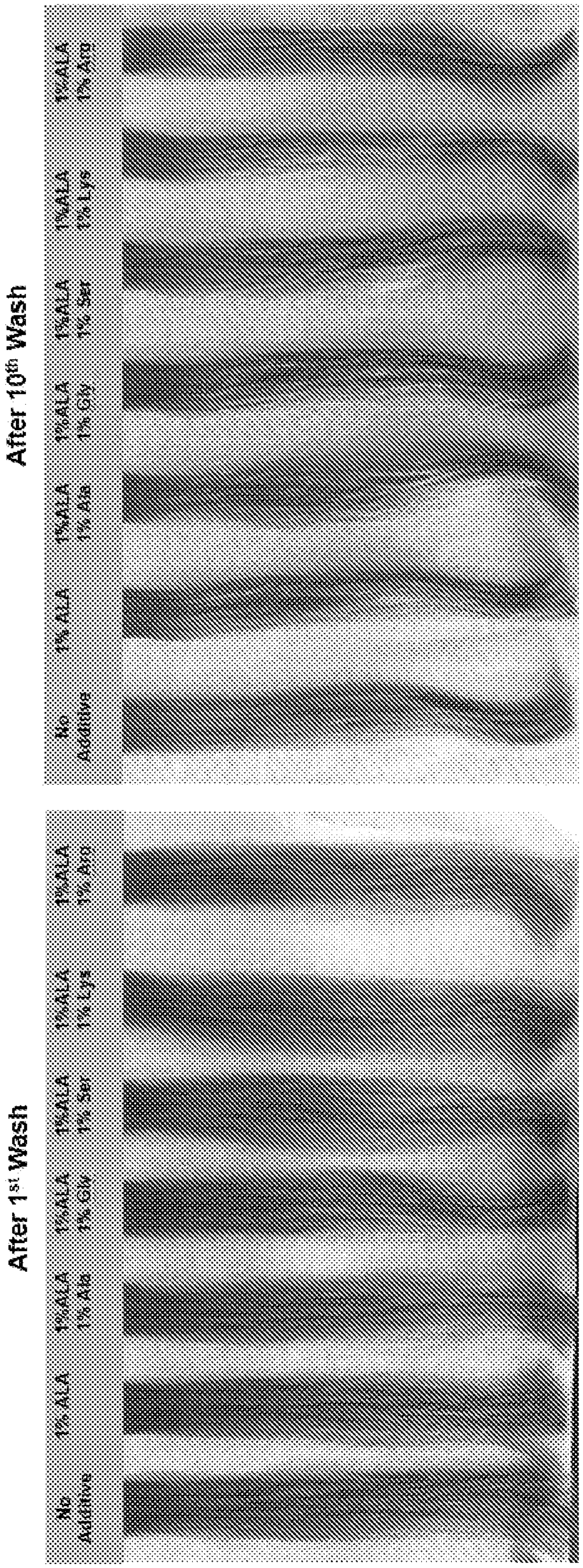
FIG. 22 depicts an image showing color retention performance for hair tresses colored in the presence of a mixture of ALA with single amino acid additives after 1st and 10th wash.

L'OREAL Paris Intense red copper (PR07/warmer) at-home color product consisting of a color gel (hair colorants) and a developer ($H_2O_2$, 20 Vol-6%) was used as a color treatment. ALA and amino acids were added in a powder form directly into a mixture containing 1 g of color gel and 1 g of developer. The total ALA and amino acid concentration was kept below 3 wt %. The color mixture was mixed for 5 mins, massaged thoroughly (~1 min) onto a bleached hair tress (1.5 g) and kept for 30 min for color development. After the treatment, tress was thoroughly washed with water and air dried. Sensory and color evaluation by a blinded evaluation panel showed that almost all tresses treated with amino acid additives led to improved sensory and tresses treated with alanine and glycine were the most preferred. FIG. 22 shows that tresses treated in the presence of a mixture of ALA with an amino acid additive like alanine, glycine, and serine exhibited similar color to that of the controls treated with no additive or with 1 wt % ALA alone after 1st wash. After 10 washes, lower degree of color fading was observed for tresses treated with ALA and amino acid mixtures compared to no additive and among amino acids, ALA-glycine system showed the best visual color retention.

Figure 23:
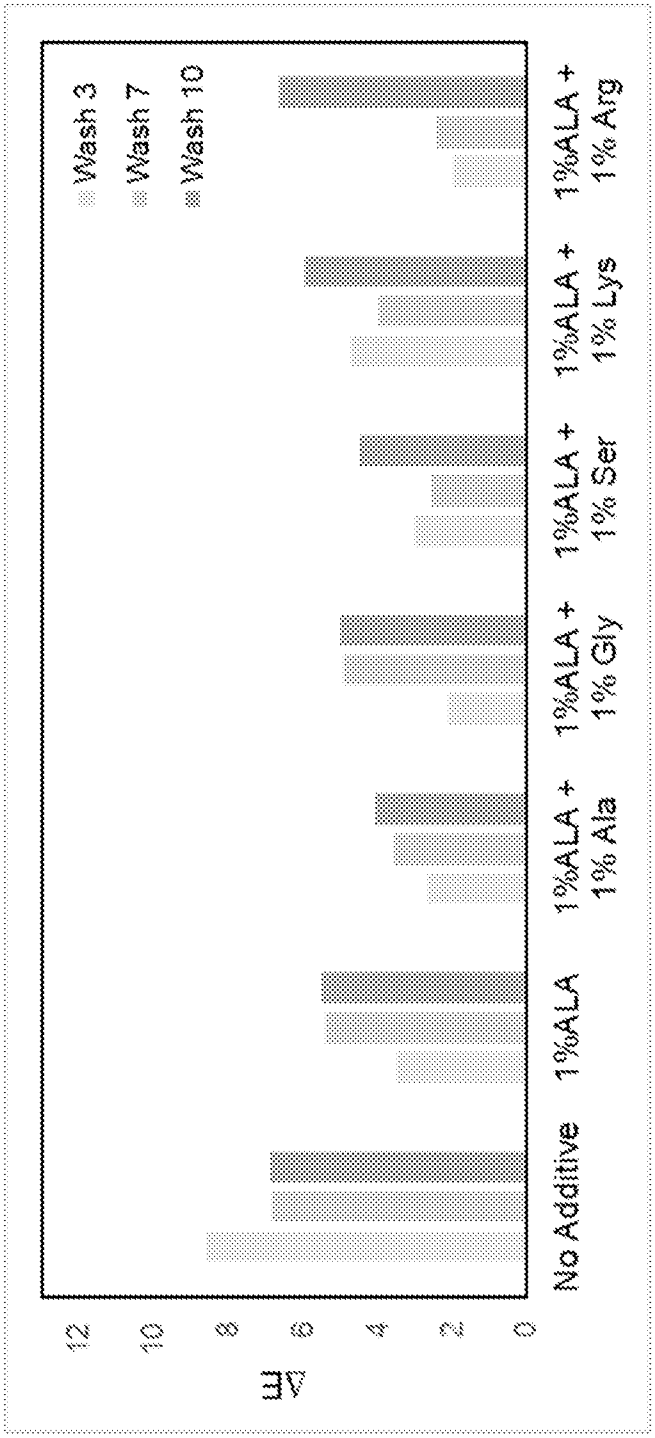
FIG. 23 depicts total color difference (ΔE) for hair tresses colored in the presence of a mixture of 1 wt % ALA and 1 wt % single amino acid compared to hair tresses colored with 1 wt % ALA alone and without any additive after 3, 7, and 10 washes.
Figure 24:
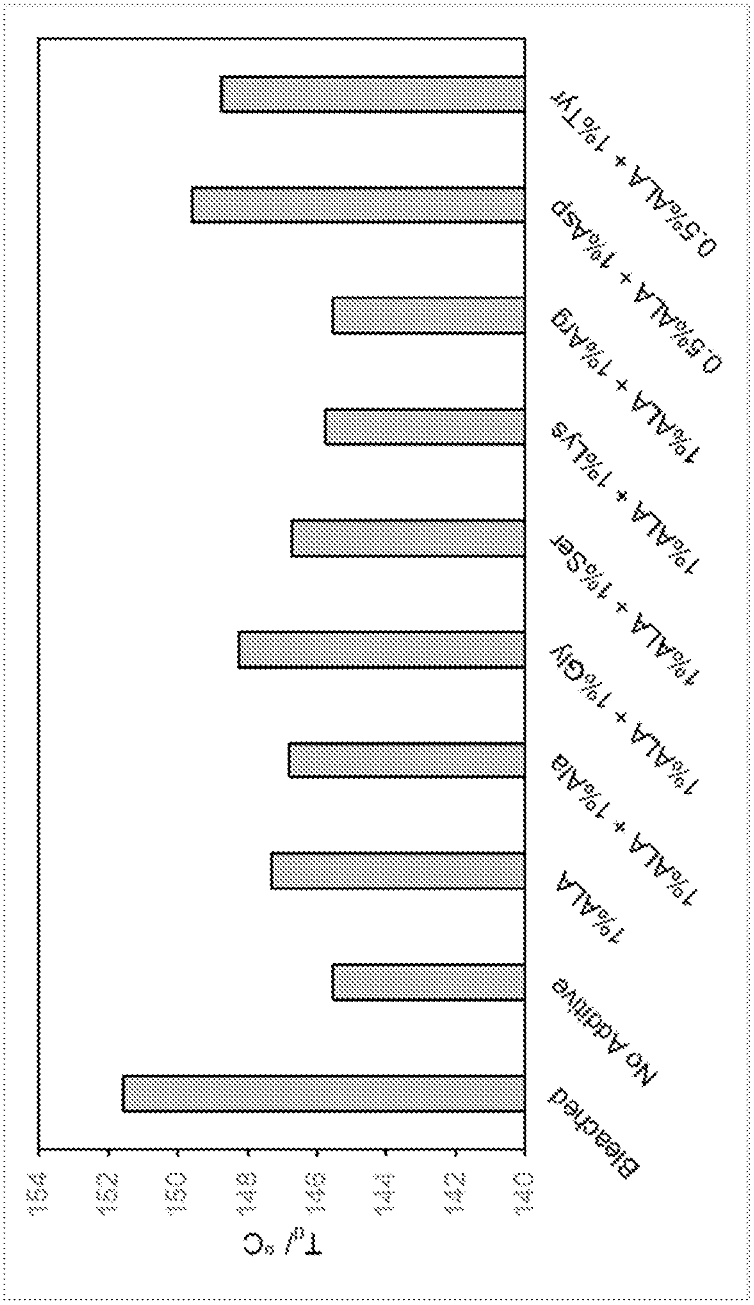
FIG. 24 depicts denaturation temperatures for hair tresses colored in the presence of a mixture of 1 wt % ALA and 1 wt % single amino acid compared to hair tresses colored without an additive mixture and in the presence of 1 wt % ALA alone.

Colorimetry analysis (FIG. 23) also shows that a much lower ΔE achieved when alanine, glycine, or serine were used as a coadditive with ALA, suggesting enhanced color protection by these amino acids. DSC analysis (FIG. 24) shows that additional boost in hair denaturation temperatures (Td) was achieved for a mixture of 1 wt % ALA and 1 wt % glycine, aspartic acid, or tyrosine. Overall, glycine was identified as a lead single amino acid coadditive based on the boost in Td and color retention benefits.

ii. α-Lipoic Acid with Binary Amino Acid Blends

Figure 25:
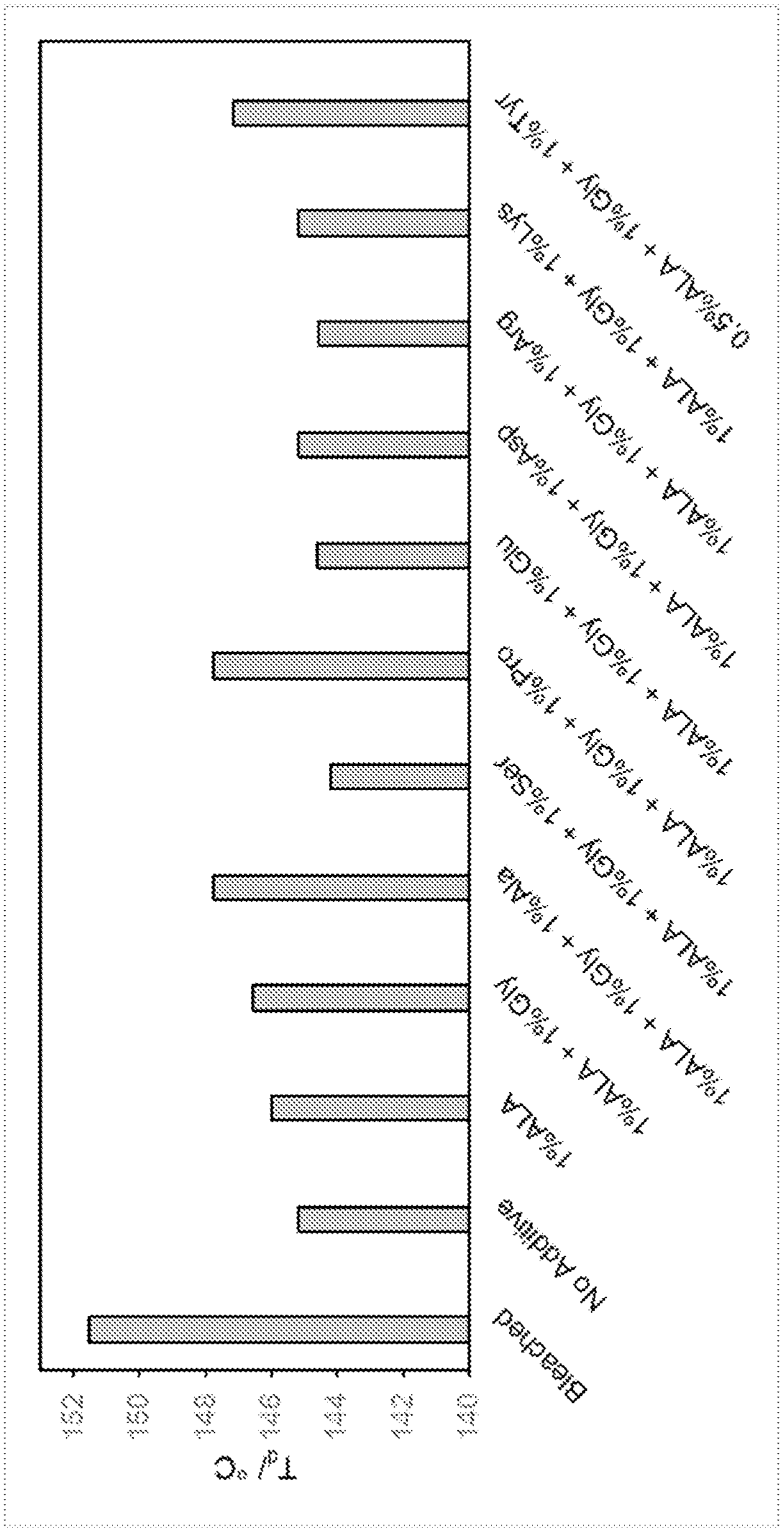
FIG. 25 depicts denaturation temperatures for hair tresses colored in the presence of a mixture of ALA with binary amino acid blend.

A series of experiments were also carried out to identify lead binary amino acids blend to use with ALA during coloring treatment. Specifically, a second amino acid such as alanine, serine, proline, tyrosine, arginine, lysine, aspartic acid, glutamic acid at a 1 wt % concentration was added with 1 wt % glycine. FIG. 25 depicts denaturation temperatures for hair tresses colored in the presence of a mixture of either 0.5 or 1 wt % ALA, 1 wt % glycine, and one more amino acid at 1 wt % concentration compared to untreated hair tresses and hair tresses colored without an additive.

Figure 26:
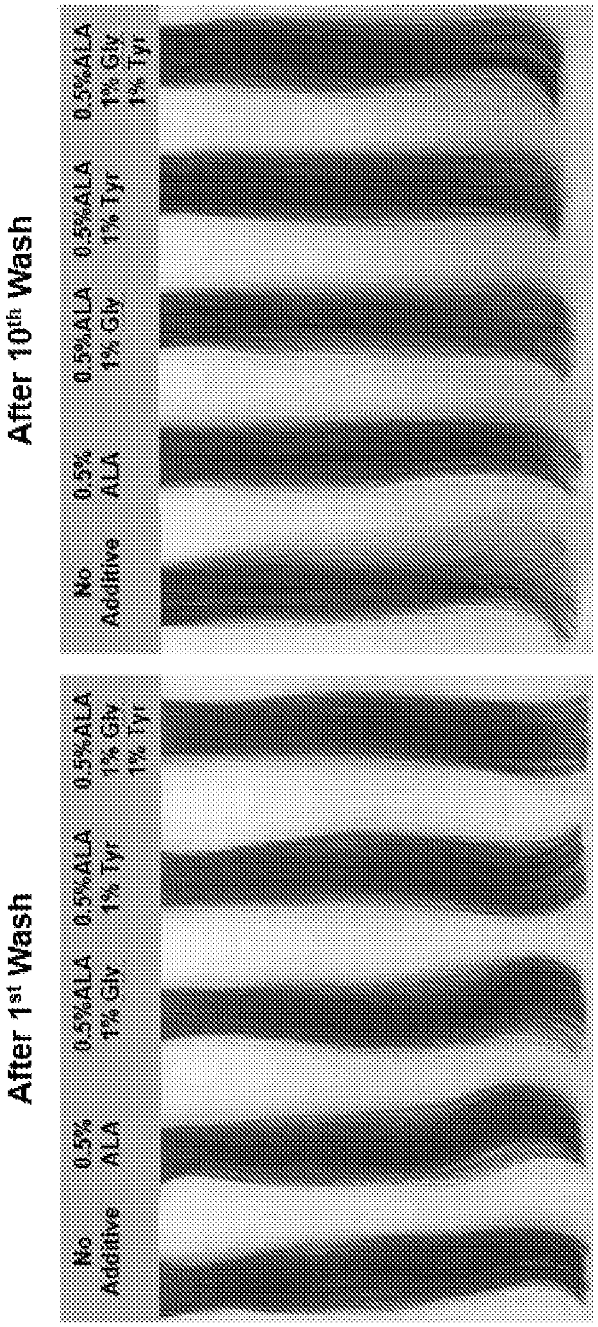
FIG. 26 depicts an image showing the color retention performance after 1st and 10th wash for hair tresses color treated with or without a mixture of ALA with binary amino acid blend.
Figure 27:
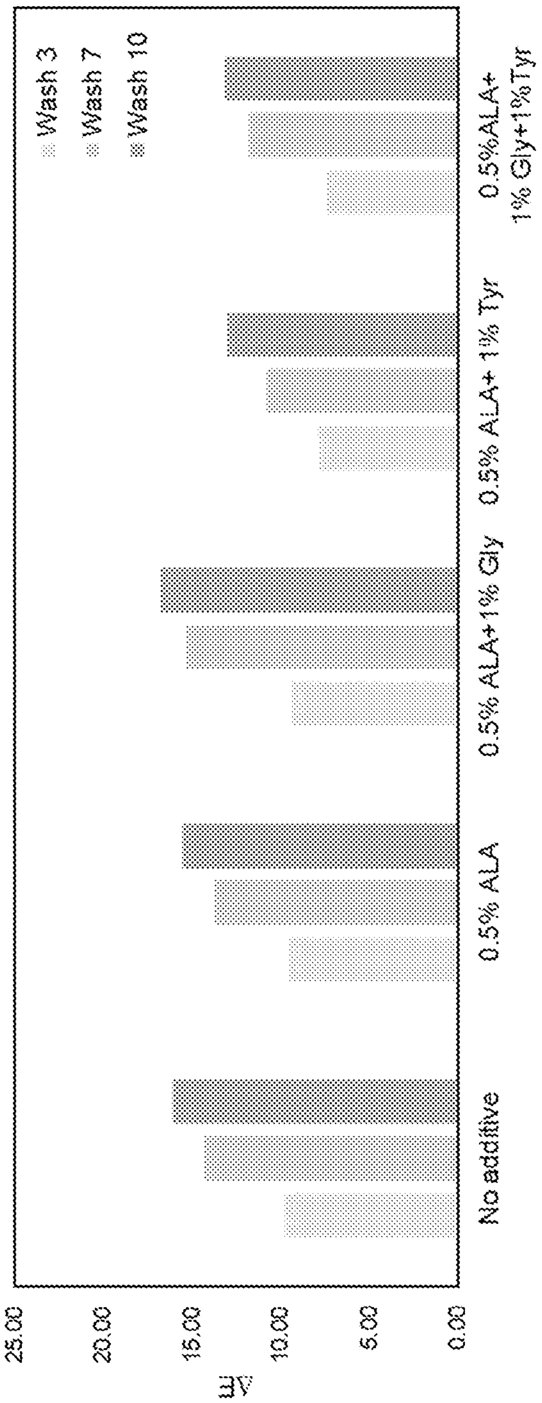
FIG. 27 depicts an image showing the overall color difference (ΔE) after 3, 7 and 10 washes for hair tresses color treated with or without a mixture of ALA with binary amino acid blend.

Sensory evaluation by a blinded evaluation panel showed that tresses treated with glycine-tyrosine amino acid blend led to most preferred sensory. Both visual observation and colorimetry analysis (FIG. 26 and FIG. 27) showed that tresses treated in the presence of a mixture of 0.5 wt % ALA with lead binary amino acid blend (1 wt % glycine and 1 wt % tyrosine) exhibited minimal color interference after 1st wash and slower color fading after 10th wash, suggesting enhanced color protection benefits by this binary amino acid blend.

iii. α-Lipoic Acid with Ternary Amino Acid Blends

Figure 28:
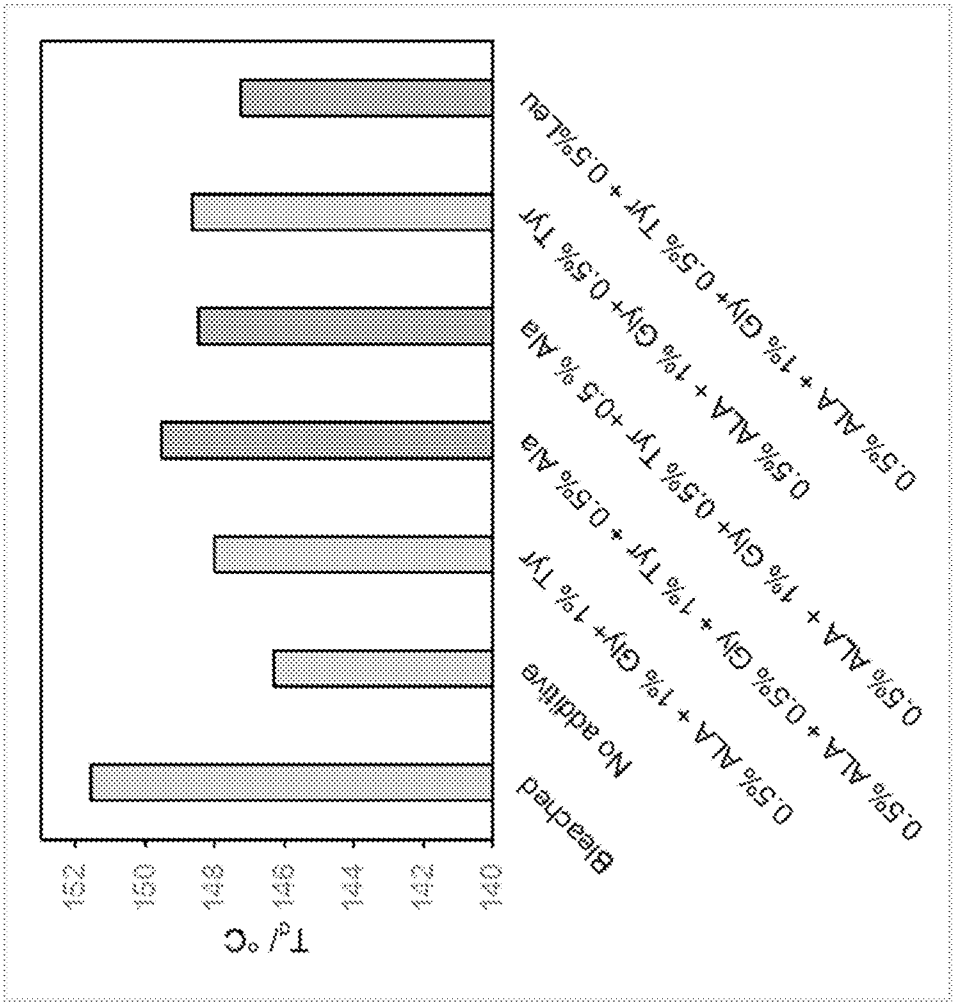
FIG. 28 depicts denaturation temperatures for hair tresses colored in the presence of a mixture of either 0.5 or 1 wt % ALA, 1 wt % glycine, with one or two more amino acids at either 0.5 or 1 wt % concentrations compared to untreated hair tress and hair tress colored without additives.

Previous experiments showed that a mixture of glycine and tyrosine was identified as the lead binary coadditive system. Ternary amino acid coadditive systems were further explored. Alanine, proline, glutamic acid and leucine were screened as a 3rd amino acid at a 0.5 wt % concentration with glycine and tyrosine. Among screened amino acids, alanine resulted in a further Td boost when used as a 3rd amino acid (FIG. 28). Some color protection benefits were also observed when alanine was used as a 3rd amino acid coadditive.

iv. α-Lipoic Acid with Commercial Amino Acid Mixtures

Figure 29:
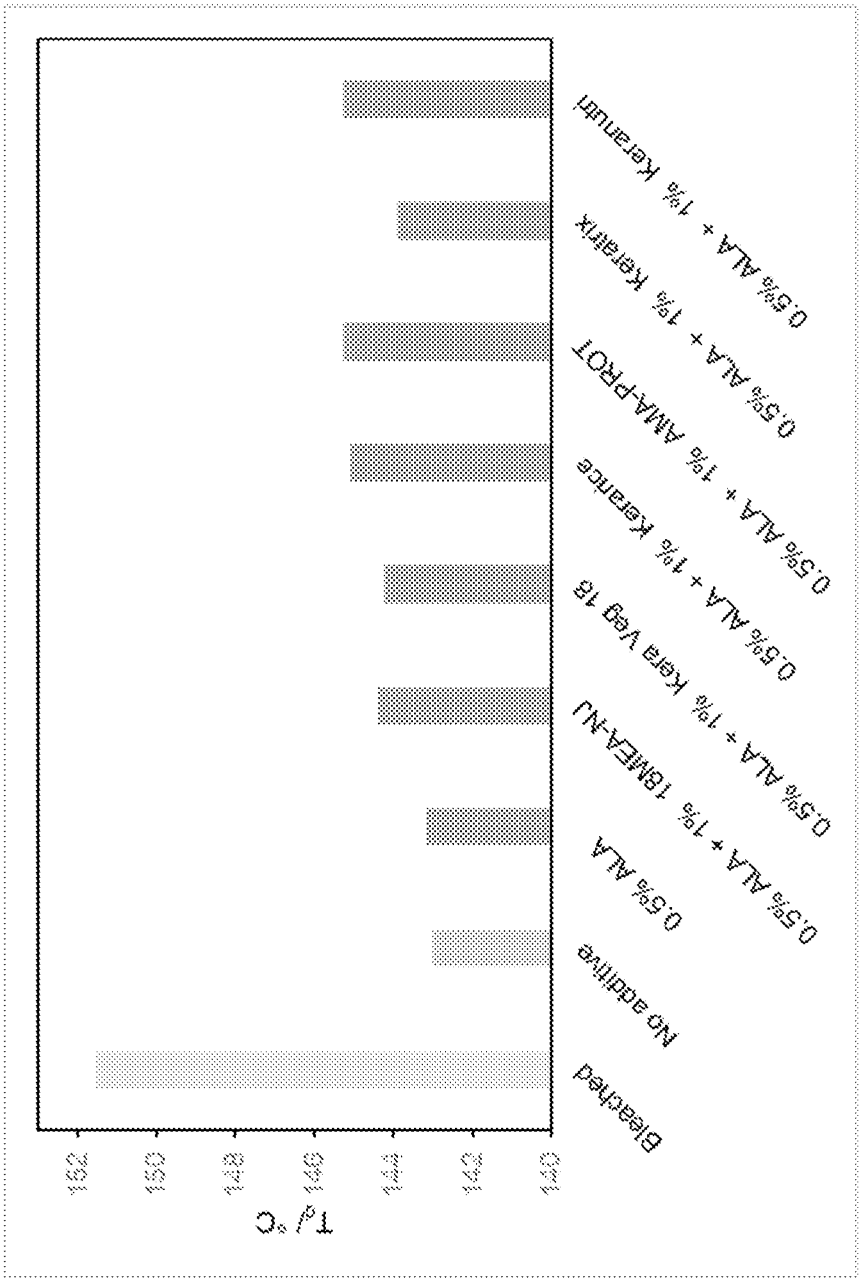
FIG. 29 depicts denaturation temperatures collected on hair tresses colored in the presence of a mixture of 0.5 wt % ALA and 1 wt % commercial amino acid blends in liquid form compared to the untreated hair tresses and hair tresses colored without addition of additives.

Various commercial amino acid mixtures as coadditives to the ALA system were also screened. The tested commercial amino acid blends in liquid form included 18MEA-NJ, Kera Veg 18, Kerarice, Ama-Prot, Keratrix, and Keranutri, while blends in solid form included Crotein-HKP and VARI-KER 100. Tresses treated with 18MEA-NJ and Keratrix showed improved sensory. Additionally, a significant improvement in denaturation temperature was observed with Kerarice, Keranutri and AMA-PROT coadditives (FIG. 29). Overall, no noticeable color protection benefits were observed for these commercial amino acid mixtures.

v. α-Lipoic Acid with Fatty Acids and Fatty Alcohols as Coadditives

A series of fatty acids that are known to leach out as a part of hair lipids including linoleic, oleic, palmitic, stearic, and palmitoleic acids were tested as coadditives. In addition, fatty alcohols such as stearyl, cetyl, and myristyl alcohols were also explored. The lead systems of 0.5 wt % ALA-1 wt % glycine and 0.5 wt % ALA-0.5 or 1 wt % glycine—0.5 or 1 wt % tyrosine were used. Fatty acids and fatty alcohols were tested at concentrations in the range of 0.1 to 0.5 wt %.

Figure 30:
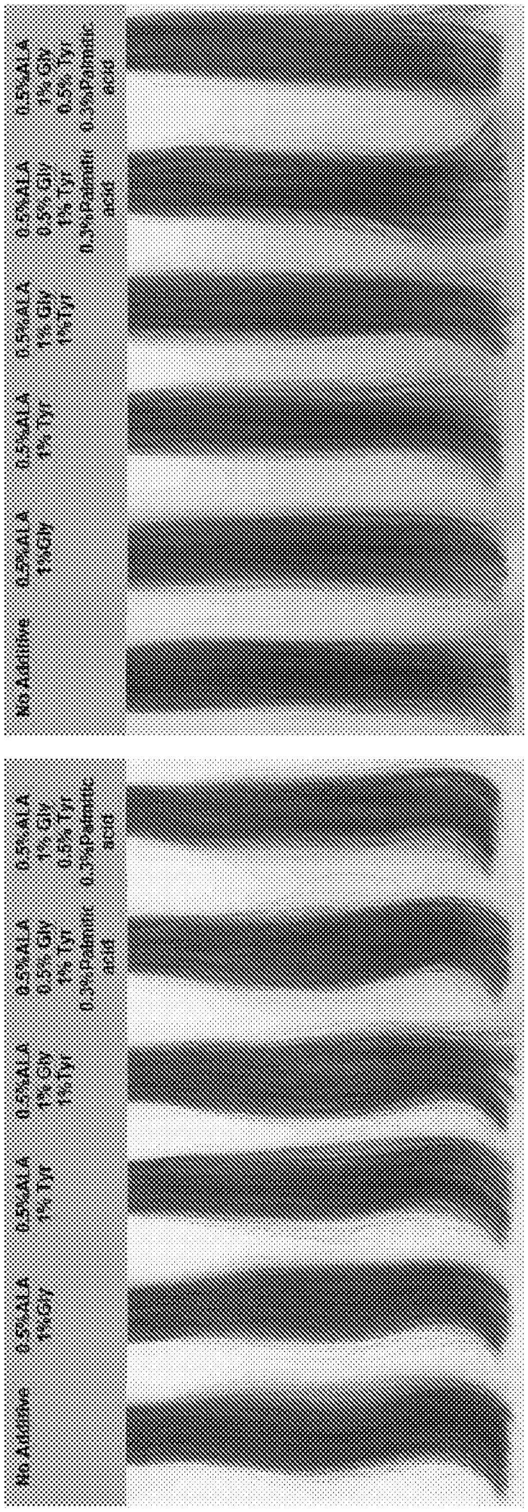
FIG. 30 depicts an image showing the color retention performance after 1st and 10th wash and overall color difference (ΔE) after 3, 7 and 10 washes for hair tresses colored in the presence of a mixture of ALA, glycine, tyrosine, and palmitic acid.
Figure 31:
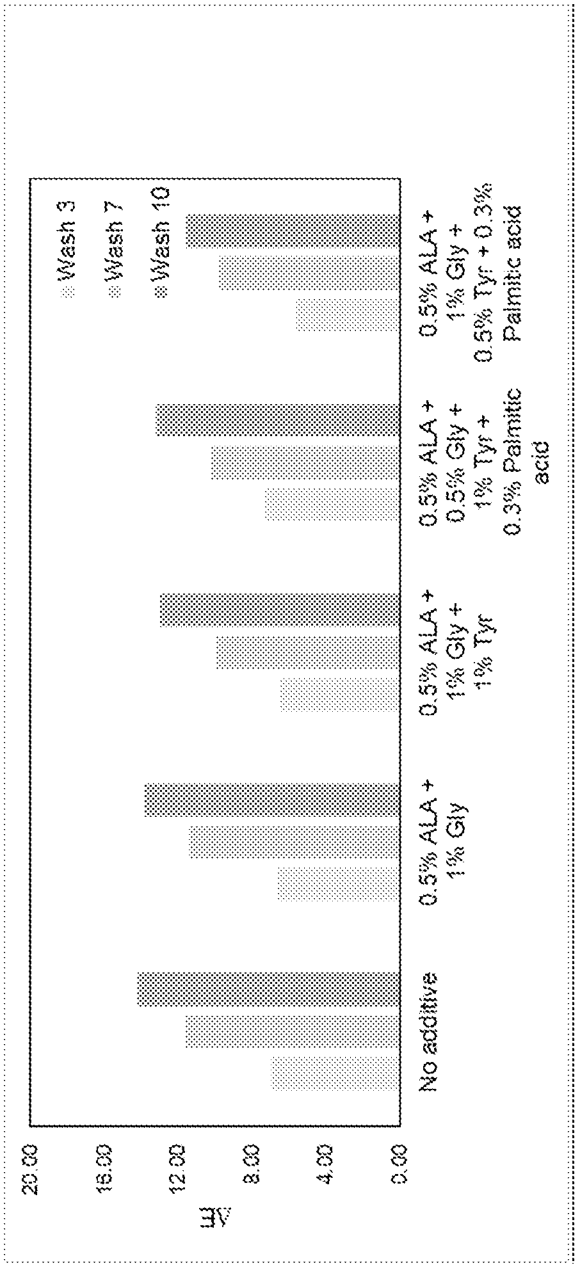
FIG. 31 depicts an image showing the color retention performance after 1st and 10th wash and overall color difference (ΔE) after 3, 7 and 10 washes for hair tresses colored in the presence of a mixture of ALA, glycine, tyrosine, and palmitic acid.

Improved sensory was achieved when palmitic and stearic acids were used as coadditives. Similar or lower ΔE was achieved when palmitic acid was used with ALA-glycine-tyrosine system at 0.3 wt % concentration indicating added color retention benefit (FIG. 30 and FIG. 31). An additional 2° C. Td boost was also observed when palmitic acid was used with the ALA-glycine-tyrosine system. No clear sensory or color protection benefits were observed for those fatty alcohols.

Amino Acids and N-Acetyl Amino Acids

Figure 10:
FIG. 10 depicts an image showing the color development on 1× bleached hair tresses treated with 1 wt % amino acid or N-acetyl amino acid in the final color mixture compared to the control with no additive.

Amino acids (e.g., glycine, serine, and alanine) or N-acetyl amino acids (e.g., N-acetyl glycine, N-acetyl serine, and N-acetyl alanine) were explored as additives during color treatment. A Wella (Colortango) permanent masque (4VR-Mahogany) salon color product comprising hair colorants (comprising primary intermediates and couplers including 2-methyl-5-hydroxy-ethylaminophenol, 1-hydroxyethyl 4,5-diamino pyrazole sulfate, and toluene-2,5-diamine sulfate) and Wella professional's (Welloxon Perfect™) developer ($H_2O_2$, 20 Vol-6% by weight) were used as the color treatment. All amino acids were added in a powder form directly into a color mixture containing 1 g color cream and 1 g developer, resulting in a 1 wt % amino acid final concentration. The color mixture was mixed for 5 min, massaged thoroughly (~1 min) onto a 1× bleached hair tress (1.5 g) and kept on for 30 min for color development. After the treatment, the colored tresses were washed thoroughly with deionized water and air dried. FIG. 10 shows that all tresses treated in the presence of amino acid and N-acetyl amino acid additives exhibited similar color to that of the control with no additive, suggesting minimal color interference by the amino acid and the N-acetyl amino acid additives. Sensory evaluation by a blinded sensory and color evaluation panel shows that almost all tresses treated with amino acid and N-acetyl amino acid additives led to improved sensory and the tress with N-acetyl alanine is preferred by all evaluators.

Figure 11A:
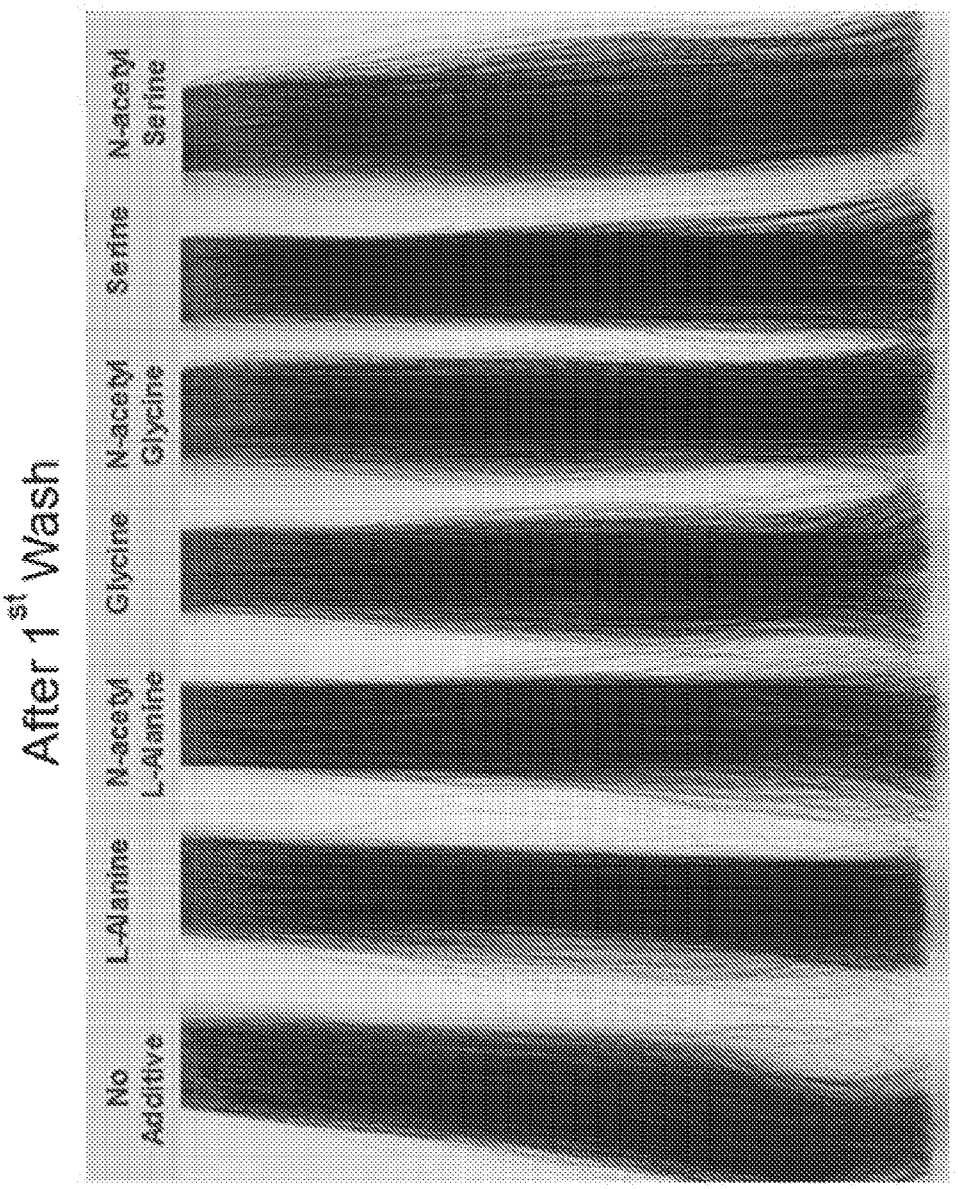
FIG. 11A depicts an image showing the color retention performance for color-treated hair tresses with or without amino acid or N-acetyl amino acid additives after 1 wash.
Figure 11B:
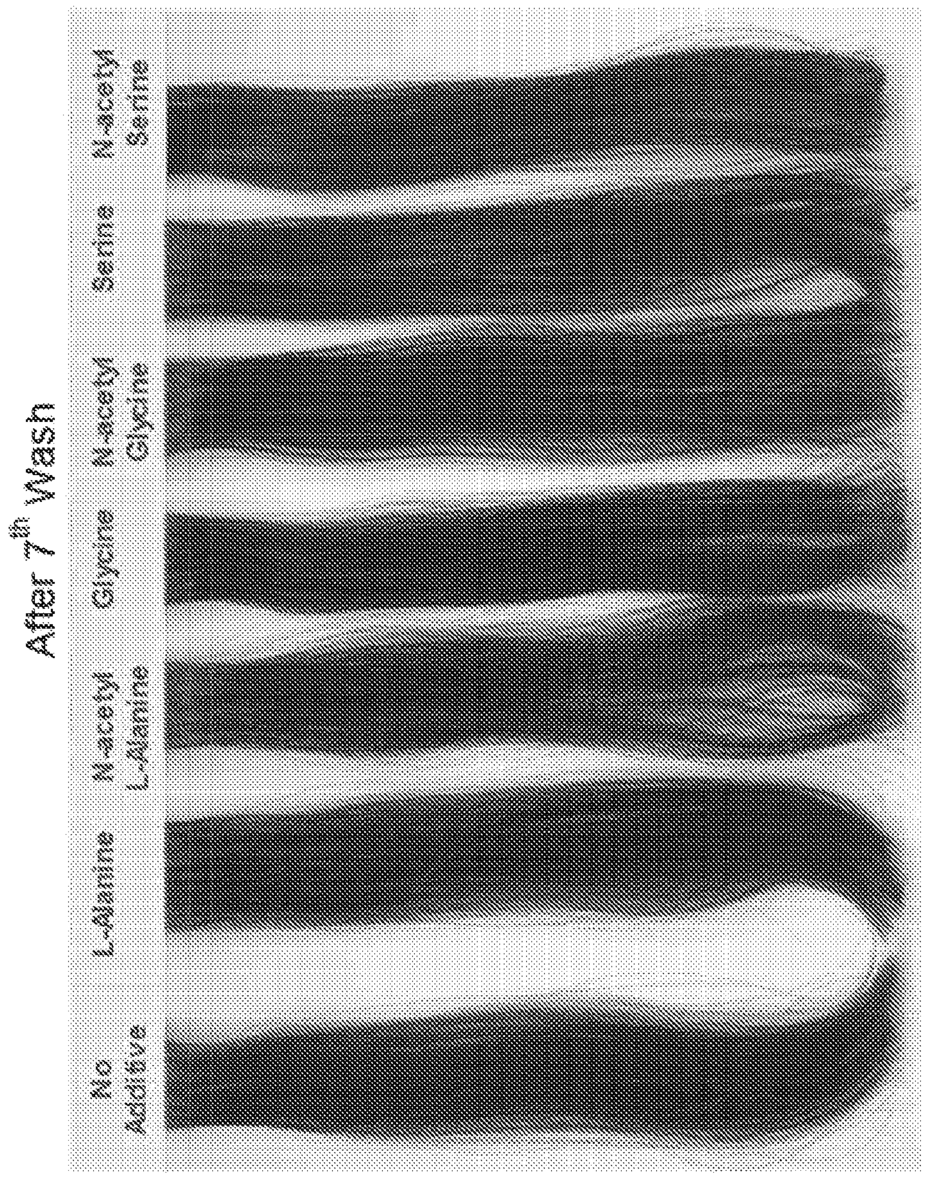
FIG. 11B depicts an image showing the color retention performance for color-treated hair tresses with or without amino acid or N-acetyl amino acid additives after 7 washes.
Figure 11C:
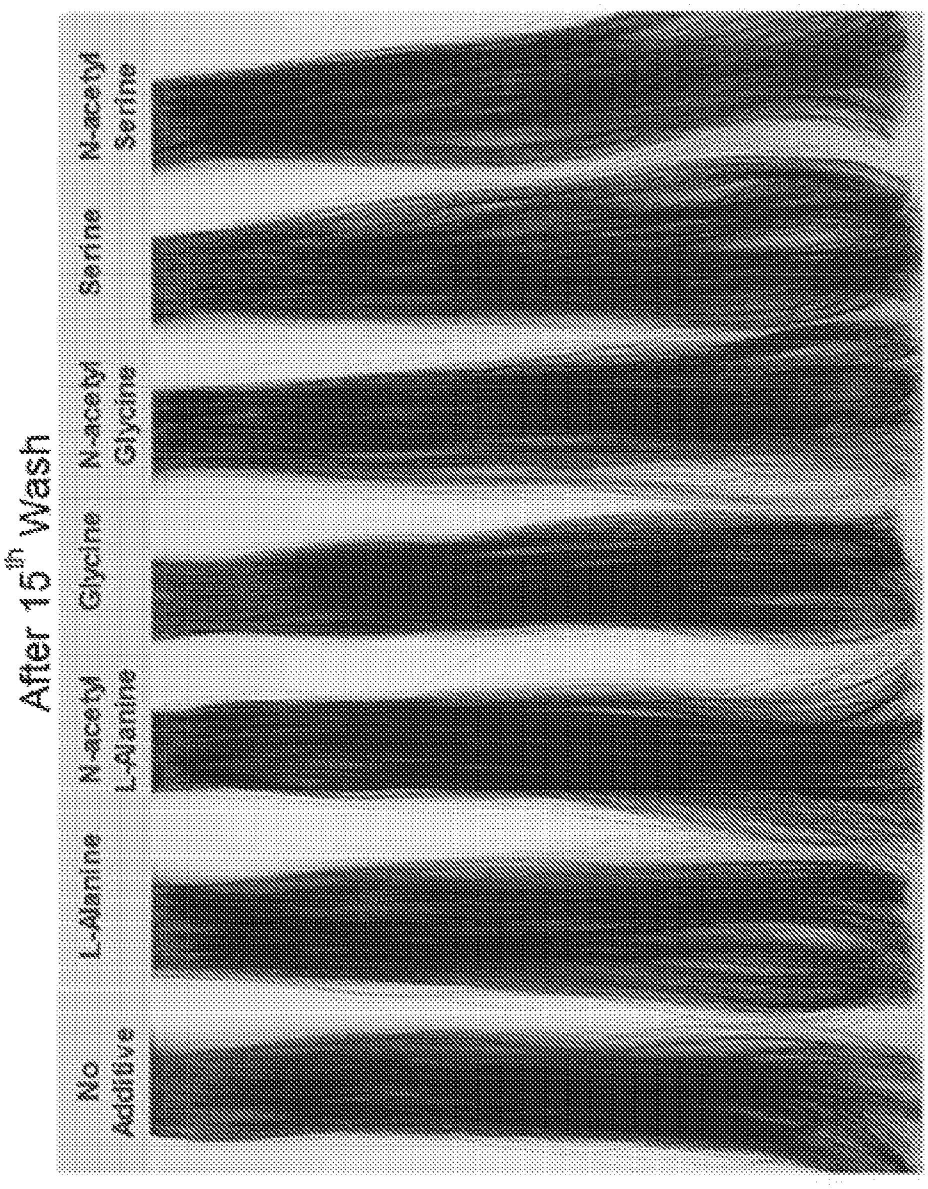
FIG. 11C depicts an image showing the color retention performance for color-treated hair tresses with or without amino acid or N-acetyl amino acid additives after 15 washes.
Figure 12:
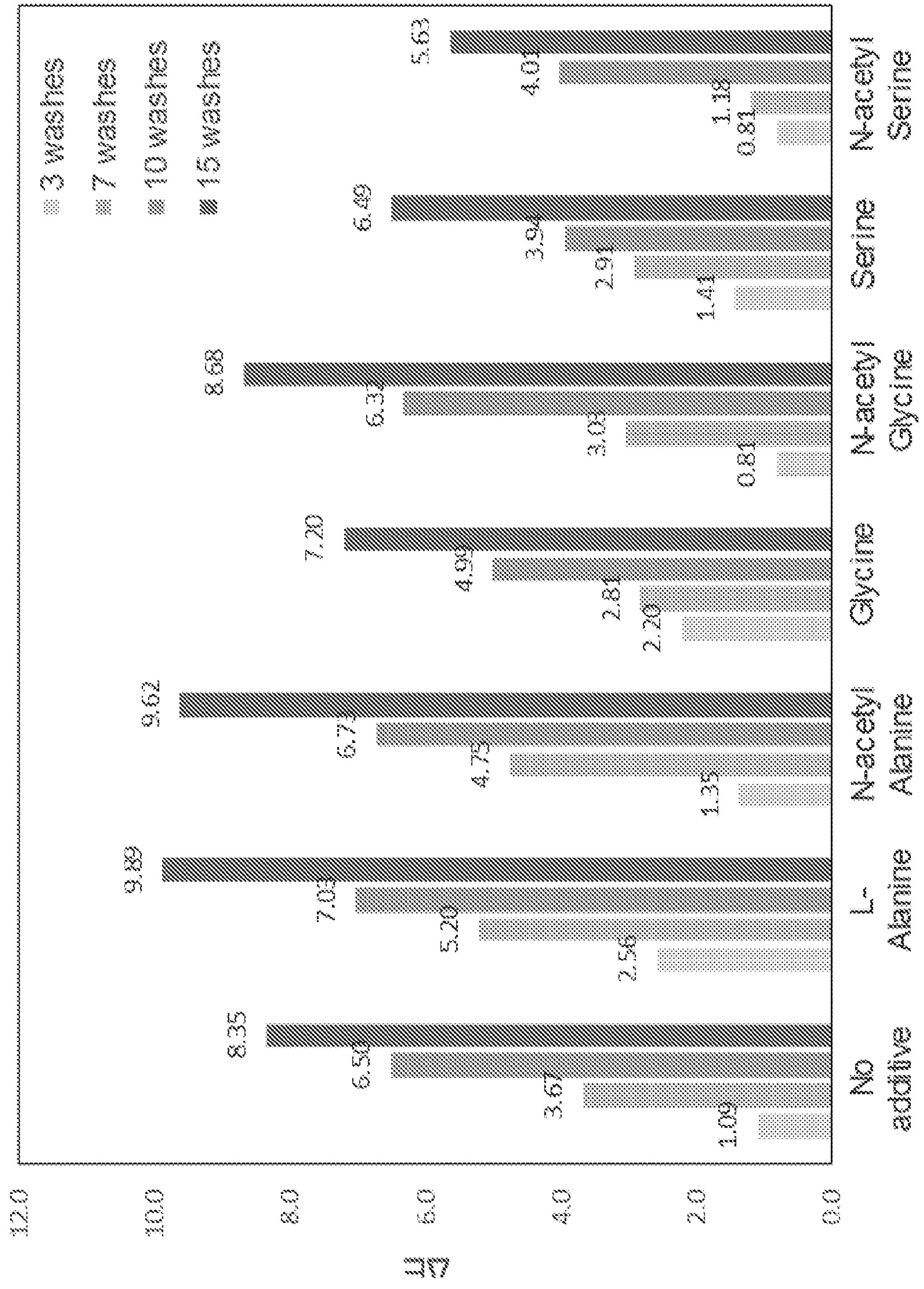
FIG. 12 depicts total color difference (ΔE) for color-treated hair tresses treated with or without amino acid or N-acetyl amino acid additives after 3, 7, 10, and 15 washes.

The color retention was also evaluated by subjecting the hair tresses to repetitive washing and drying cycles, and color changes after 3, 7 and 10 washes were evaluated. FIG. 11A-11C shows the washing studies of color-treated hair tresses in the presence of different amino acids as compared to the control with no additive. Although all tresses underwent gradual color fading over the washing studies, slower color fading was observed for some of the tresses treated with amino acid or N-acetyl amino acid additives. To further quantify the color changes, colorimetry analysis was performed on all of the colored tresses. FIG. 12 shows the total color difference (ΔE) for tresses treated with or without amino acid additives. Lower ΔE values were achieved when serine, N-acetyl serine, or glycine was used as an additive, suggesting enhanced color protection by those amino acids and N-acetyl amino acids.

Amino Acid Blends

Based on the previous results of ALA and amino acid blend systems, glycine and tyrosine were identified as lead amino acid additives. In the next studies, a series of tests were performed using glycine (Gly) and tyrosine (Tyr) blend alone or with additional various amino acids. For all experiments, glycine and tyrosine concentration was fixed at 1 and 0.5 wt %, respectively.

Ternary AA Blends

Figure 32:
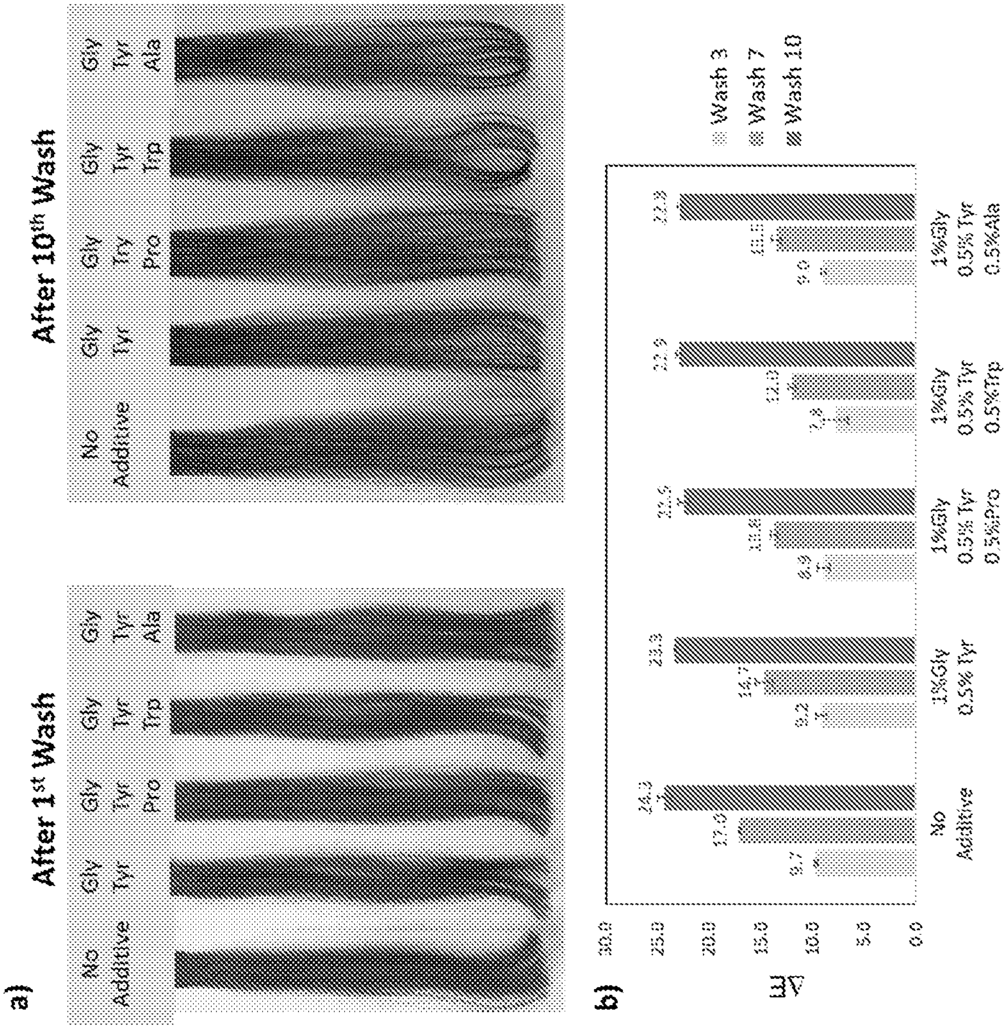
FIG. 32(*a*) depicts hair tresses colored in the presence of ternary amino acid blends systems after 1st and 10th wash.

In the first set of experiments, hydrophobic amino acids such as alanine (Ala) and tryptophan (Trp), along with proline (Pro) were explored at 0.5 wt % concentration each. As seen in FIG. 32, when any of the amino acid mixtures were added during coloring, less total color loss was observed compared to tresses that were colored without any additives. Among those blends, glycine-tyrosine-proline and glycine-tyrosine-alanine systems showed the least color loss over 10 washes.

Basic amino acid, polylysine (polymer of lysine amino acid), which is expected to have a high affinity towards negatively charged hair and thus creating a protective barrier against loss of dye molecules, was also studied as an additional amino acid at a 0.25-1 wt % concentration with the glycine-tyrosine blend. However both visual evaluation and colorimetry analysis showed that only a slight color protection benefits were achieved.

Tertiary Amino Acid Blends

Pyrrolidone carboxylic acid (PCA) and arginine (Arg) were screened at various concentrations together with glycine and tyrosine, with the total amino acid concentration fixed at 2 wt %. Among all different PCA:Arg ratios tested, the least color loss without immediate color interference was observed for 2:1 PCA:Arg (0.33% PCA and 0.17% Arg) concentration ratio.

Figure 33:
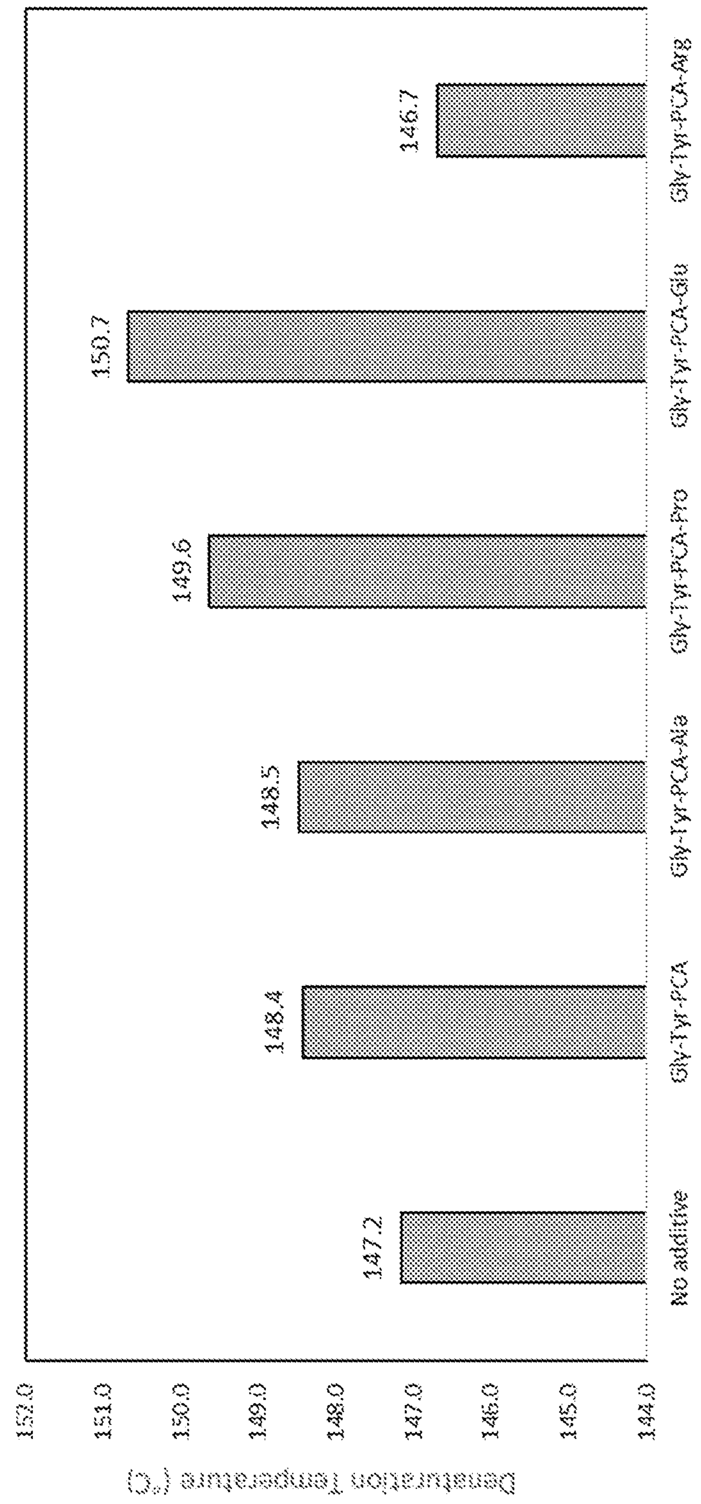
FIG. 33 depicts denaturation temperatures of hair tresses after coloring treatment with and without various tertiary amino acid blends.

Based on the results obtained for glycine-tyrosine-alanine glycine-tyrosine-proline systems, PCA was incorporated on top of those amino acids to further boost color retention. In addition, PCA with glutamic acid or arginine were also explored. It was found that hair tresses treated with glycine-tyrosine-PCA-proline and glycine-tyrosine-PCA-glutamic acid systems, both showed significant Td boost compared to hair tresses treated with coloring mixture alone (FIG. 33), indicating protective benefits from hair damage with these systems.

Gluconolactone and Citric Acid Mixture

Figure 13:
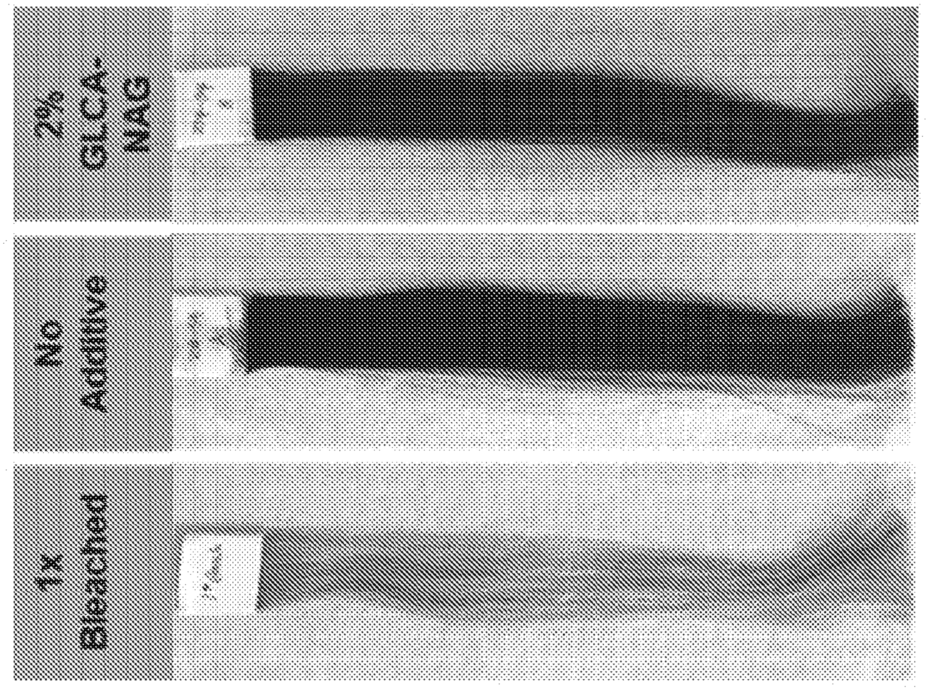
FIG. 13 depicts an image showing the color development on 1× bleached hair tresses treated with 2 wt % GLCA-NAG in the final color mixture compared to control with no additive.

Studies showed that hair can be strengthened by a treatment with a mixture of gluconolactone and citric acid (GLCA). The addition of N-acetyl-glycine (NAG) can also further improve hair sensory properties. Therefore, in this study, a mixture of gluconolactone, citric acid, and N-acetyl-glycine (GLCA-NAG) was explored as an additive during color treatment. A Wella (Colortango) permanent masque (4VR-Mahogany) salon color product comprising hair colorants (comprising primary intermediates and couplers including 2-methyl-5-hydroxy-ethylaminophenol, 1-hydroxyethyl 4,5-diamino pyrazole sulfate, and toluene-2,5-diamine sulfate) and Wella professional's (Welloxon Perfect™) developer ($H_2O_2$, 20 Vol-6% by weight) were used as the color treatment. For preliminary testing, a GLCA-NAG powder mixture was directly mixed into a color mixture containing 1 g color cream and 1 g developer, resulting in a 2 wt % GLCA-NAG final concentration. The final color mixture was mixed for 5 min, massaged thoroughly (~1 min) onto a 1× bleached hair tress (1.5 g) and kept on for 30 min for color development. As shown in FIG. 13, both the tresses treated with or without GLCA-NAG additive showed similar color development, suggesting minimal color interference by the GLCA-NAG mixture.

Figure 14:
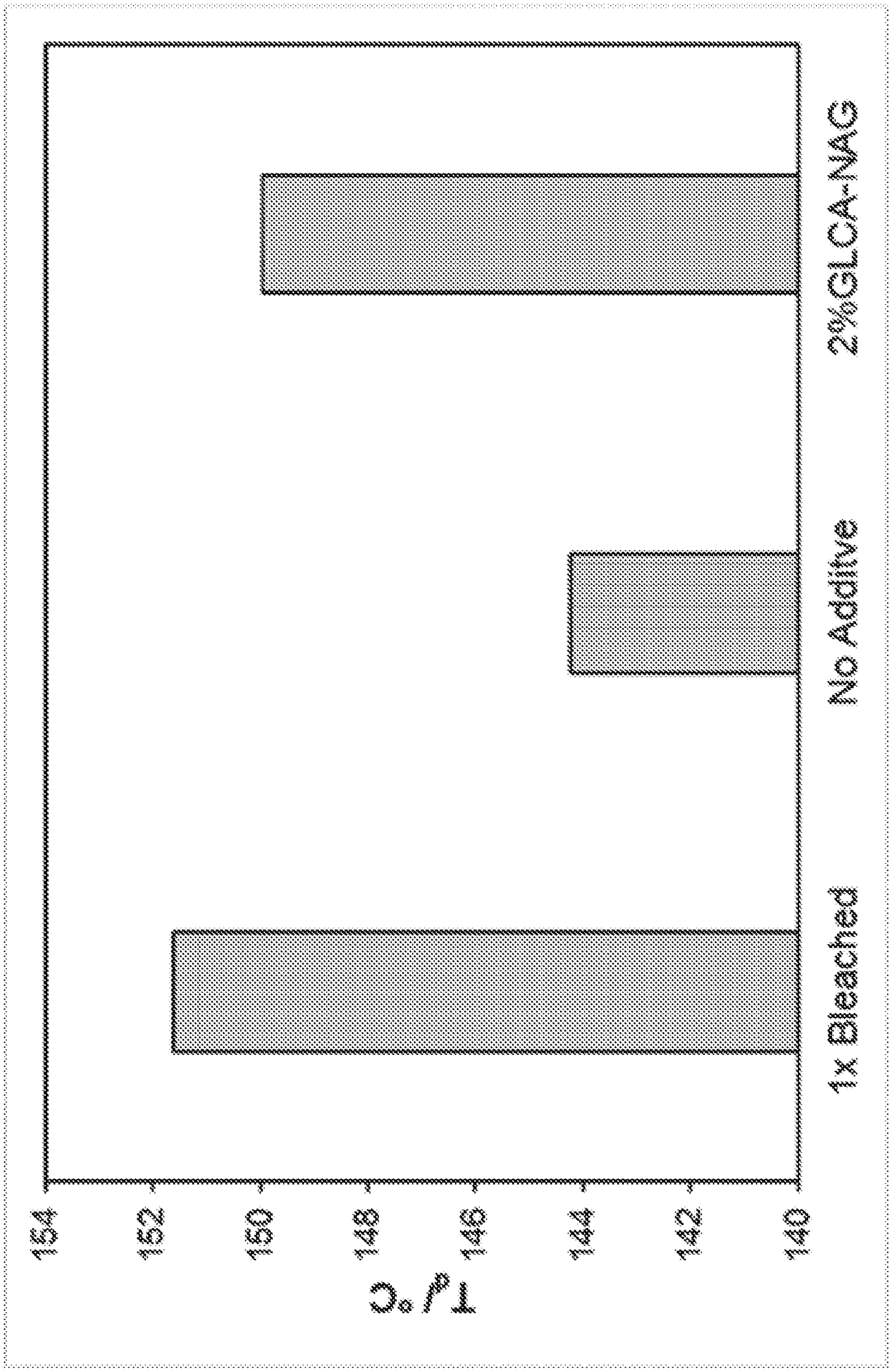
FIG. 14 depicts denaturation temperatures collected on salon color-treated hair tresses with 2 wt % GLCA-NAG as an additive compared to control with no additive.

FIG. 14 shows that, when no additive was used, hair denaturation temperature decreased by 8° C. after the color treatment. However, when 2 wt % GLCA-NAG was used as an additive, only a minimal decrease in Td (~2° C.) was observed after the color treatment, suggesting minimal hair damage and improvements in hair strength by the color treatment in the presence of GLCA-NAG. In addition, concentration for GLCA-NAG could be further lowered to 0.5 wt % for each of the key ingredients without sacrifice in Td or color retention. In addition to N-acetyl glycine (NAG) as the main secondary amino acid, other amino acid additives were also explored, including alanine (Ala), glycine (Gly), glutamic acid (Glu), aspartic acid (Asp), and lysine (Lys) at 1 wt % concentration each. Among all the amino acid screened, glutamic acid, aspartic acid, and lysine showed the best color protection benefits.

Polyphenols

Figure 15:
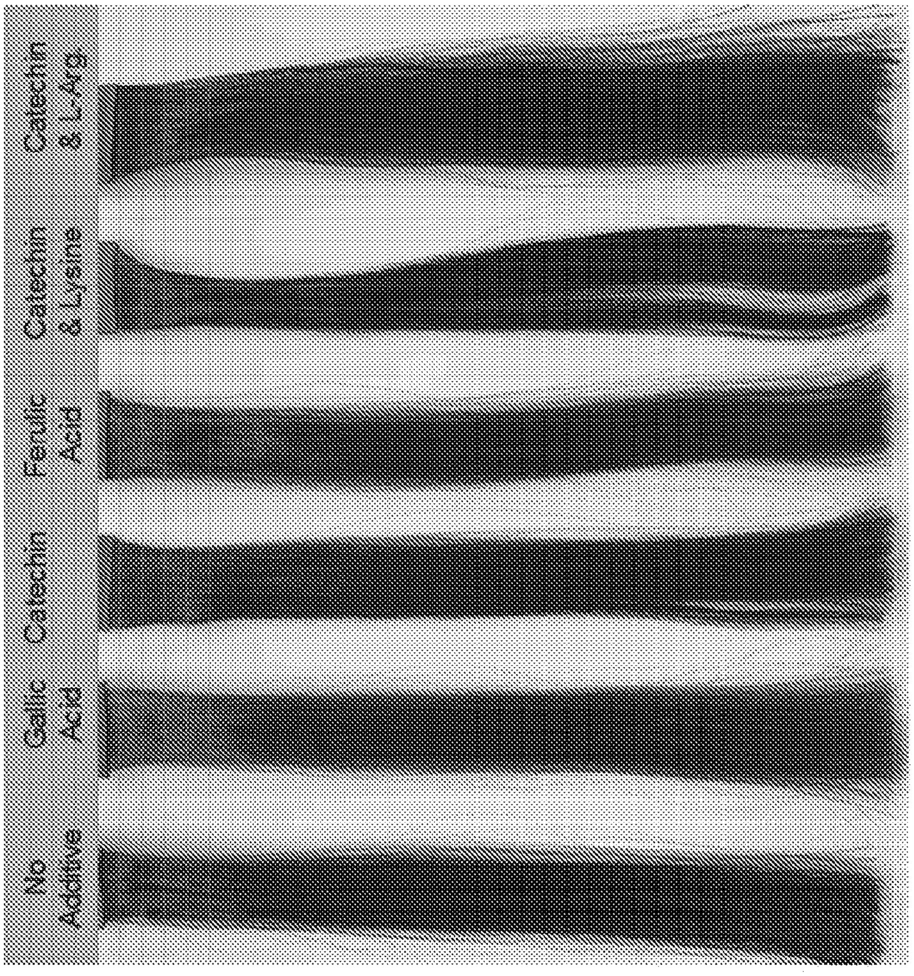
FIG. 15 depicts an image showing the color development on 1× bleached hair tresses treated with 2 wt % gallic acid, catechin, or ferulic acid or 2% polyphenol (catechin)+2% amino acid (Lysine or L-arginine) in the final color mixture compared to control with no additive.

A list of polyphenols including gallic acids, catechin, ferulic acid were also explored as additives during color treatment. Amino acids like lysine and L-arginine, which were shown to improve the performance by polyphenols in previous studies, were also added together with selected polyphenols. In this study, a Wella (Color Touch) permanent masque (6/75-Dark Blonde/Brown Red-Violet) salon color product comprising hair colorants (comprising primary intermediates and couplers including N,N-bis-(2-hydroxyethyl)-para-phenylene diamine and 2-Amino-4-Hydroxyethylaminoanisole) and Wella professional's (Welloxon Perfect™) developer ($H_2O_2$, 20 Vol-6% by weight) was used for the color treatment. For preliminary testing, all polyphenols were added in powder form into a color mixture containing 1 g color cream and 1 g developer, resulting in a 2 wt % polyphenol final concentration. The final color mixture was mixed for 5 min, massaged thoroughly (~1 min) onto a 1× bleached hair tress (1.5 g) and kept on for 30 min for color development. FIG. 15 shows that the treatment with gallic acid or ferulic acid additive led to a slightly lighter red color compared to the control without any additive. However no obvious color interference was noticed for all tresses treated with catechin additive (with or without amino acid).

Example 2—Additive as a Pre-Treatment

N-Acetyl L-Cysteine

Figure 16:
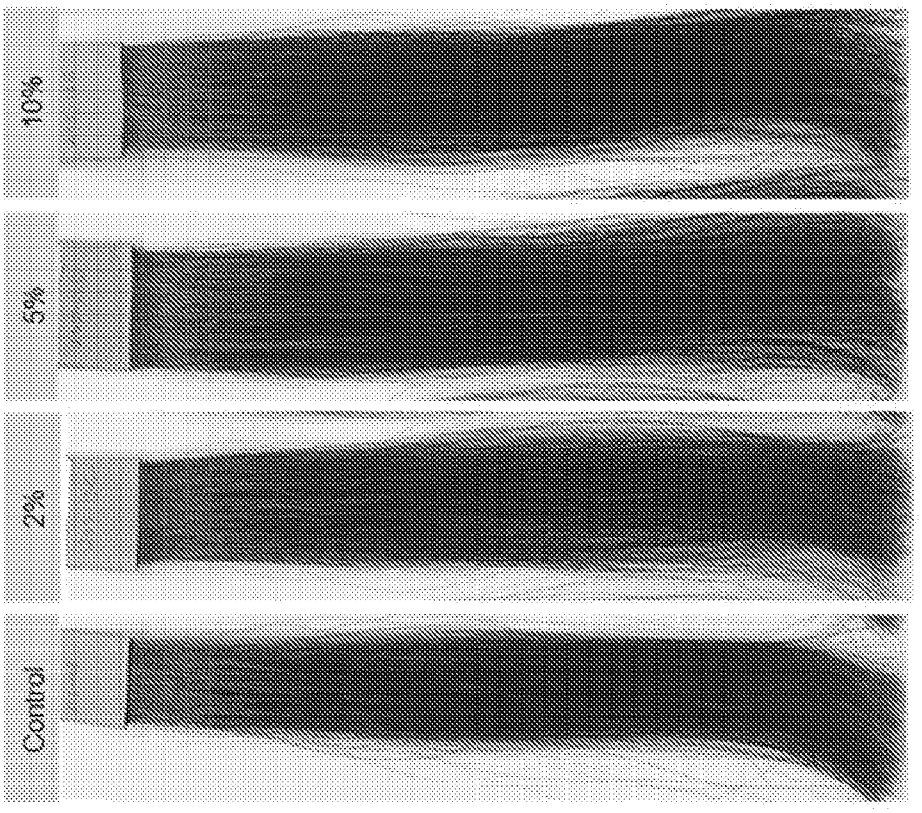
FIG. 16 depicts an image of hair tresses pre-treated with N-acetyl-L-Cys (NALC) at 3 different concentrations (2 wt %, 5 wt %, and 10 wt %) compared to the color-treated hair tress without any pre-treatment.
Figure 17:
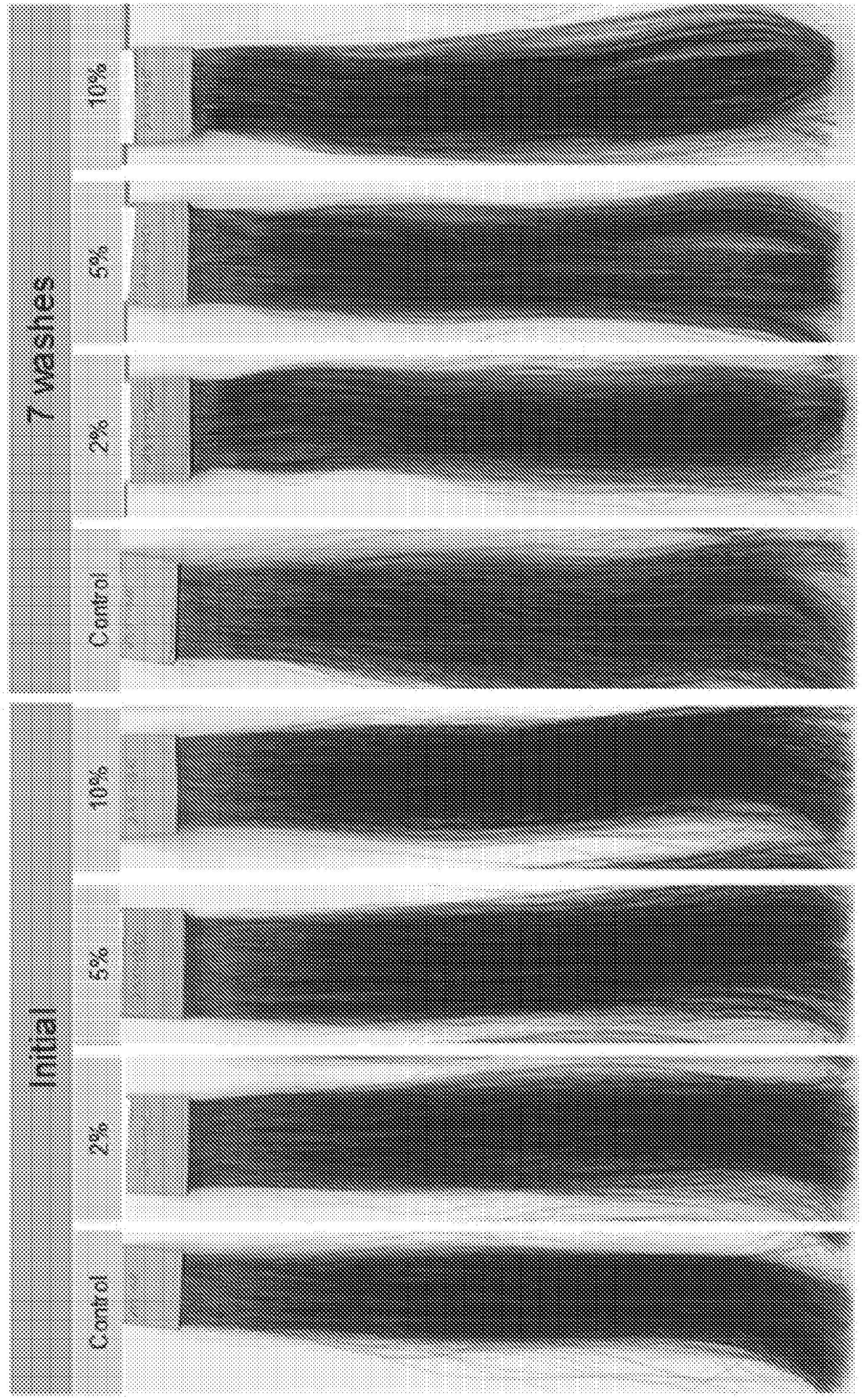
FIG. 17 depicts an image showing the color retention performance after initial (1st) and 7 washes for hair tresses pre-treated with NALC at 3 different concentrations (2 wt %, 5 wt %, and 10 wt %) as compared to the control without any pre-treatment.

Delivery of thiol molecules like N-acetyl-L-cysteine (NALC) at low pH (~pH 2.0) led to exploring using a NALC solution as a pre-treatment before coloring. 1× bleached medium brown straight hair tress (~1.5 g) was treated for 15 min with a small amount (~0.4 g) of NALC aqueous solution at a 2 wt %, 5 wt %, or 10 wt % concentration and pH 2.0. After the pre-treatment, the hair tresses were colored with a mixture of Wella (Colortango) permanent masque (4VR-Mahogany) hair color product comprising hair colorants (comprising primary intermediates and couplers including 2-methyl-5-hydroxy-ethylaminophenol, 1-hydroxyethyl 4,5-diamino pyrazole sulfate, and toluene-2,5-diamine sulfate) and Wella professional's (Welloxon Perfect™) developer ($H_2O_2$, 20 Vol-6% by weight). The final color mixture was mixed for 5 min, massaged thoroughly (~1 min) onto the pre-treated 1× bleached hair tress (1.5 g) and kept on for 30 min for color development. As shown in FIG. 16, hair tresses treated with N-acetyl-L-Cys showed minimal color interference at all concentrations. A washing study (FIG. 17) also showed that color-treated hair tresses pre-treated with NALC exhibited improved color retention.

Beside the key ingredient N-acetyl L-cysteine (NALC), various amino acids were also explored as coadditives, including glycine, arginine, proline, glutamic acid, and pyrrolidone carboxylic acid. Systems with either glycine or proline resulted in lower total color loss (better color retention) compared to the NALC pre-treatment alone. Additional sensory benefits were observed when proline or glutamic acid was used as a coadditive with NALC.

N-Acetyl L-Cysteine (NALC) Pre-Treatment with Commercial Drop-In Products

Figure 34:
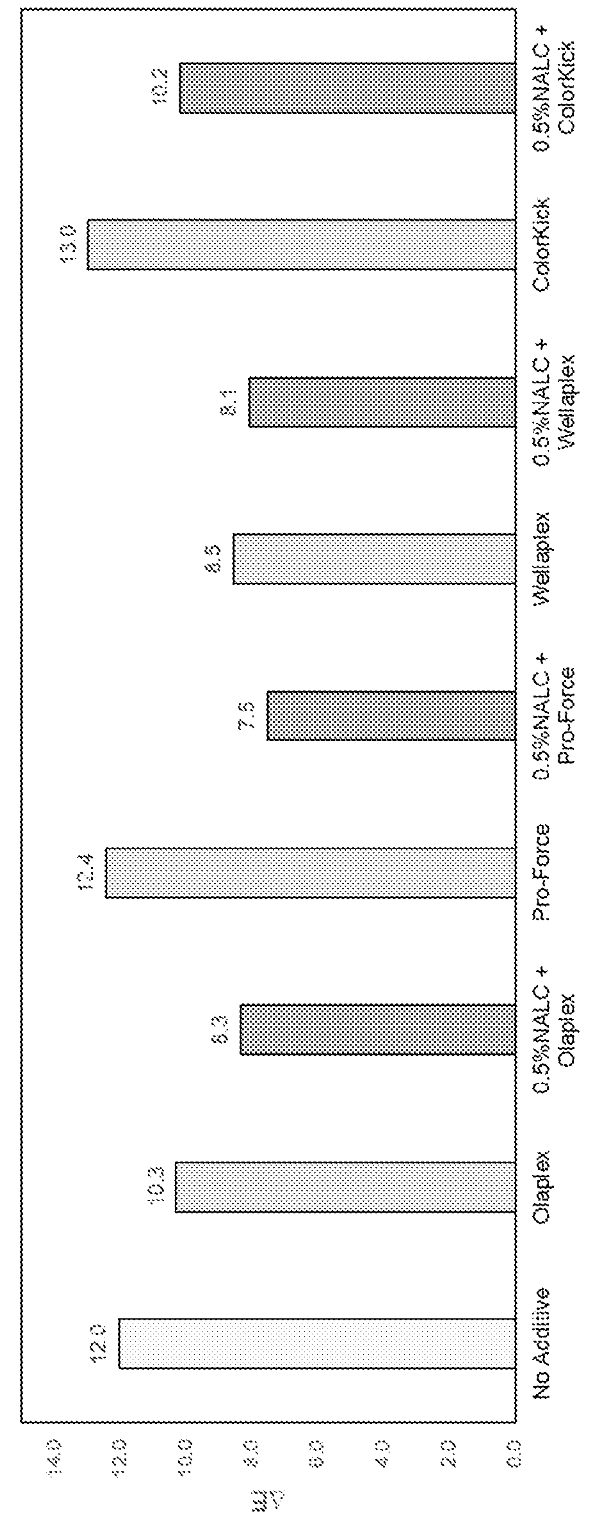
FIG. 34 depicts total color loss after soaking of tresses in water for 30 minutes to mimic 3-7 washing and drying cycles. Tresses were treated with commercial coloring mixtures (Olaplex, Wellaplex, Pro-Force, and ColorKick) with and without N-acetyl L-cysteine pre-treatment step.

N-acetyl L-cysteine pre-treatment before coloring service was also explored in conjunction with commercial color drop-in products to enhance performance. For this purpose, four products were explored: Olaplex No. 1 (Bond Multiplier) and No. 2 (Bond Perfector) by Olaplex, Colorkick by Virtue, Pro-Force Bonder 101 & Scaler 102 by Framesi, and Wellaplex No 1 and No 2 by Wella. FIG. 34 shows total color loss after soaking tresses in water treated with commercial coloring drop-in mixtures with or without a NALC pre-treatment step. For all commercial treatments, NALC pre-treatment lowered total color loss, indicating improved color retention.

Example 3—Additive as a Post-Treatment

Gluconolactone and Citric Acid Mixture

Figure 18:
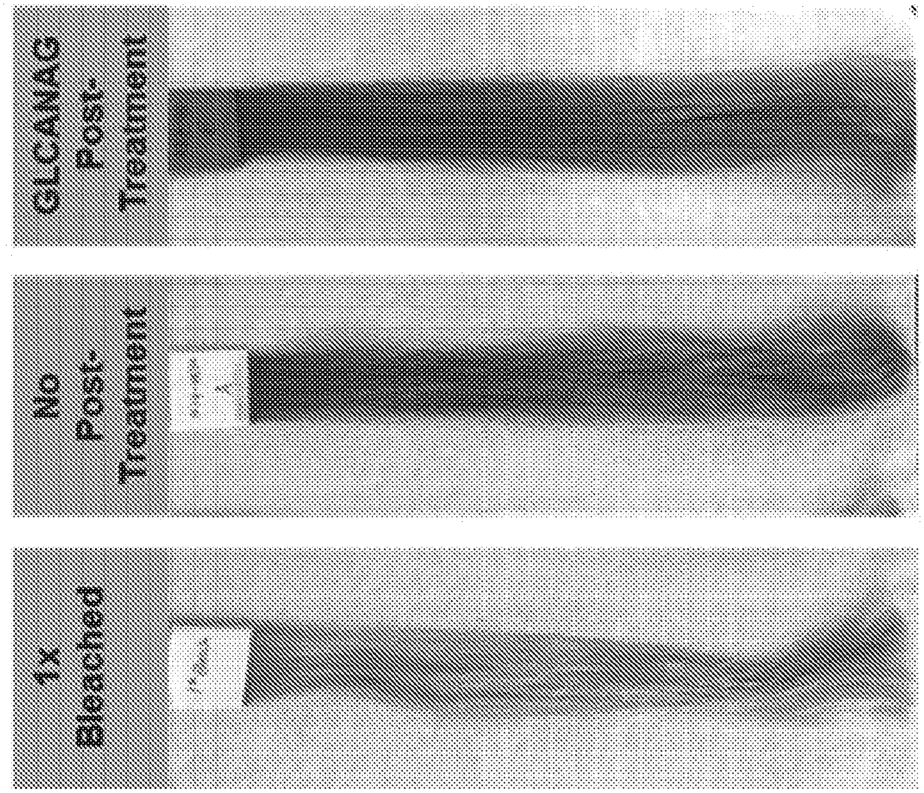
FIG. 18 depicts an image showing the color development on 1× bleached hair tresses post-treated with a 2 wt % GLCA-NAG aqueous mixture after color treatment compared to the control with no post-treatment.

Besides being used as an additive during coloring, GLCA-NAG was also explored as a post-treatment after coloring. L'OREAL® Paris Intense red copper (PR07/warmer) color product color product comprising a color gel (comprising primary intermediates and couplers, including 2-methyl-5-hydroxy-ethylaminophenol, p-aminophenol, p-phenylenediamine, and 6-hydroxyindole) and a developer ($H_2O_2$, 20 Vol-6% by weight) was used. Color treatment was carried out by mixing the color gel (1 g) and developer (1 g) for 5 min. The mixture was massaged thoroughly (~1 min) onto a 1× bleached hair tress (1.5 g) and kept on for 25 min for color development. After the colored tress was thoroughly rinsed with DI water, it was further treated with a 2 wt % GLCA-NAG aqueous solution (pH 2.0) and kept for 15 min followed by blow-out. As shown in FIG. 18, no noticeable color change was observed after the post-treatment with GLCA-NAG.

Figure 19:
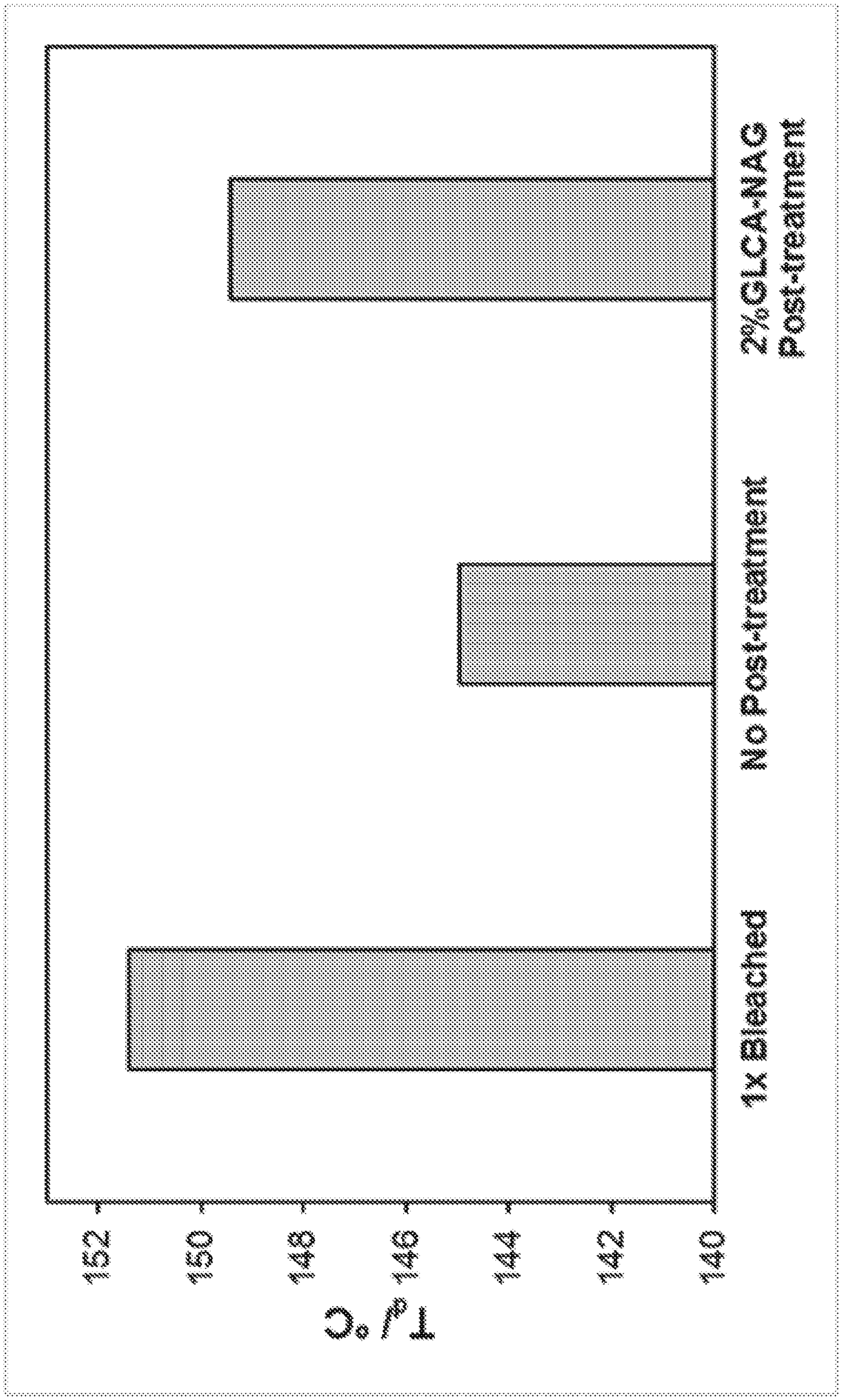
FIG. 19 depicts denaturation temperatures collected on home color-treated hair tresses with 2 wt % GLCA-NAG as post-treatment compared to control with no post-treatment.

Differential scanning calorimetry was performed on both tresses to determine the effect of GLCA-NAG as a post treatment on hair thermal properties. FIG. 19 shows denaturation temperatures collected on color treated hair tresses with or without a GLCA-NAG post-treatment. The color treatment with no additive resulted in ~6.5° C. decrease in Td. However, a 5° C. recovery in Td was achieved after the GLCA-NAG post-treatment, suggesting significant strengthening benefits by the GLCA-NAG system.

Figure 20:
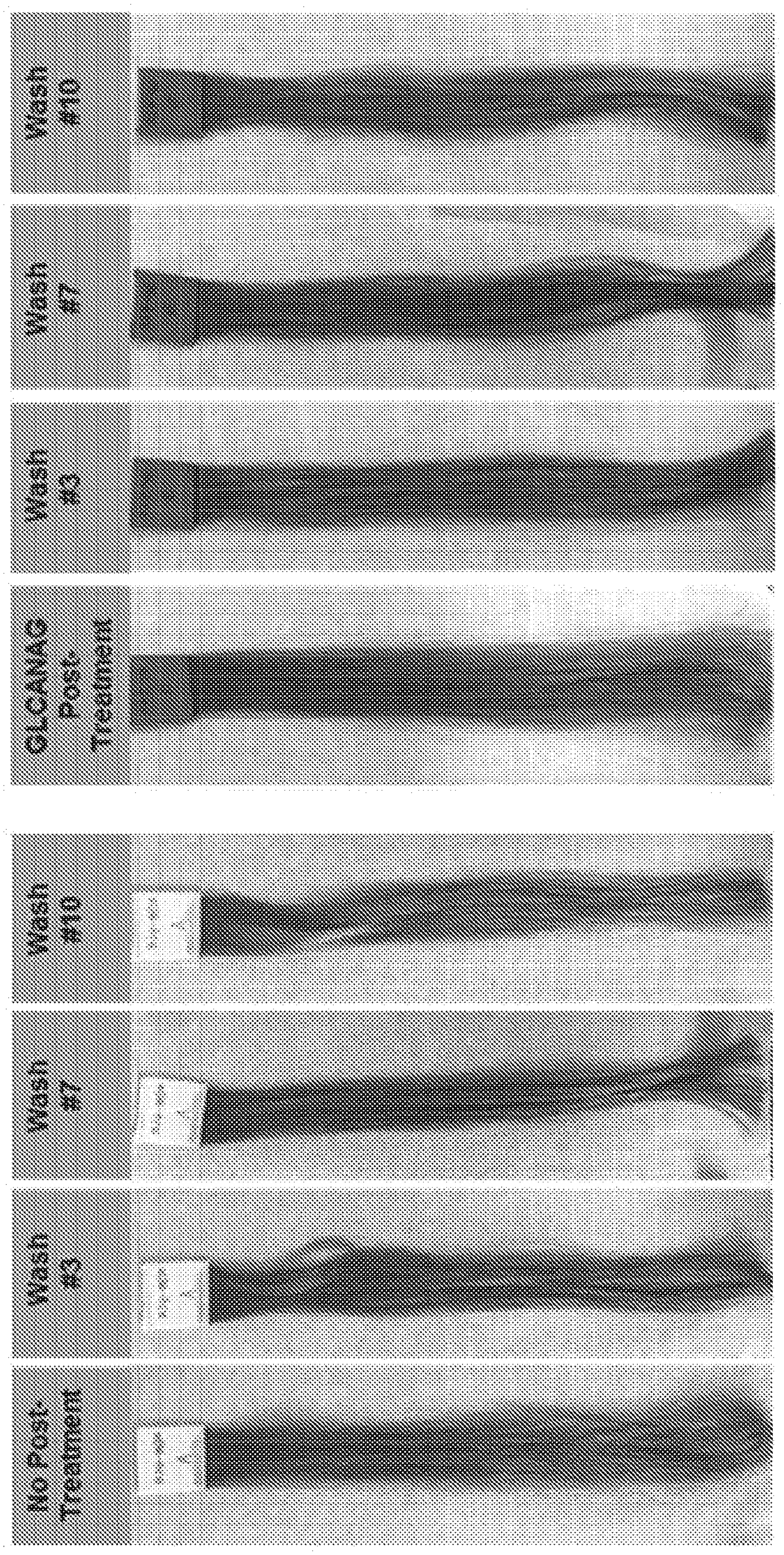
FIG. 20 depicts an image showing the color retention performance over 10 washes of color-treated hair samples with or without 2 wt % GLCA-NAG post-treatment.

The color retention was further studied by subjecting both tresses to several cycles of washing and drying, and color changes after 3, 7 and 10 washes were evaluated. FIG. 20 shows that the control tress without any post-treatment became lighter in color after 10th wash. However, no noticeable color change was observed after 10th wash for the tress with the GLCA-NAG post-treatment. The results suggest improved color retention by the GLCA-NAG post-treatment.

Polyphenols

Figure 21:
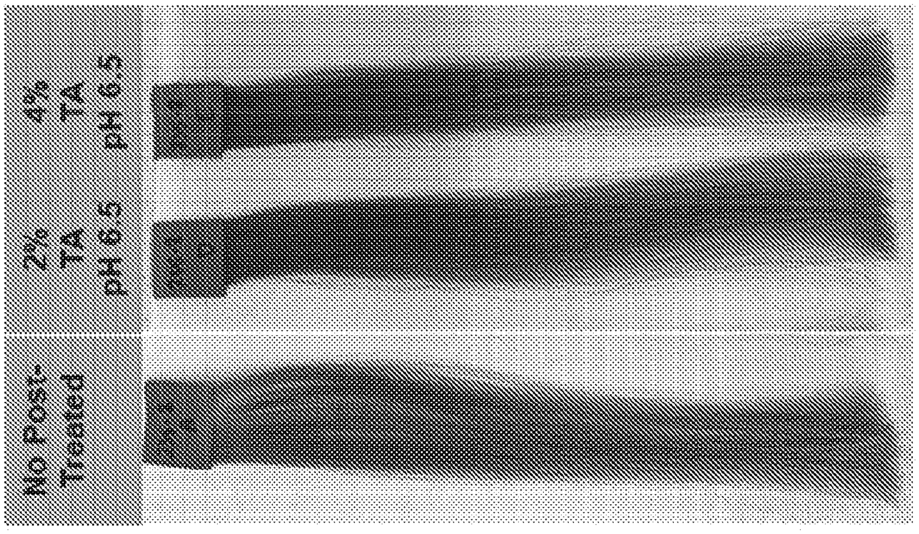
FIG. 21 depicts an image of color-treated hair tresses post-treated with tannic acid (TA) at 2 concentrations (2 wt %, 4 wt %) compared to the color treated hair tress with no post-treatment.

The potential of using polyphenols as a post-treatment was also explored to increase Td and to minimize the damage via further crosslinking. In this study, 1× bleached medium brown straight hair was treated with L'OREAL® Paris Intense red copper (PR07/warmer) color product color product comprising a color gel (comprising primary intermediates and couplers, including 2-methyl-5-hydroxy-cthylaminophenol, p-aminophenol, p-phenylenediamine, and 6-hydroxyindole) and a developer ($H_2O_2$, 20 Vol-6% by weight). Color treatment was carried out by mixing the color gel (1 g) and the developer (1 g) for 5 min. The mixture was massaged thoroughly (~1 min) on to the 1× bleached hair tress (1.5 g) and kept on for 25 min for color development. After the color treatment, the hair tress was massaged with a tannic acid (TA) post-treatment solution (~1 min) and kept on to react for 15 min, followed by blowing out. Two different concentrations (2 wt % and 4 wt %) of TA post-treatment solutions were tested. FIG. 21 shows that no noticeable color interference was observed for either TA concentrations. Differential scanning calorimetry analysis shows that hair denaturation temperatures for the tresses post-treated with TA solutions at both concentrations slightly increased (~1° C., data not shown), suggesting some strengthening benefits by the TA systems.

Comparisons with Commercial Treatments

Figure 35:
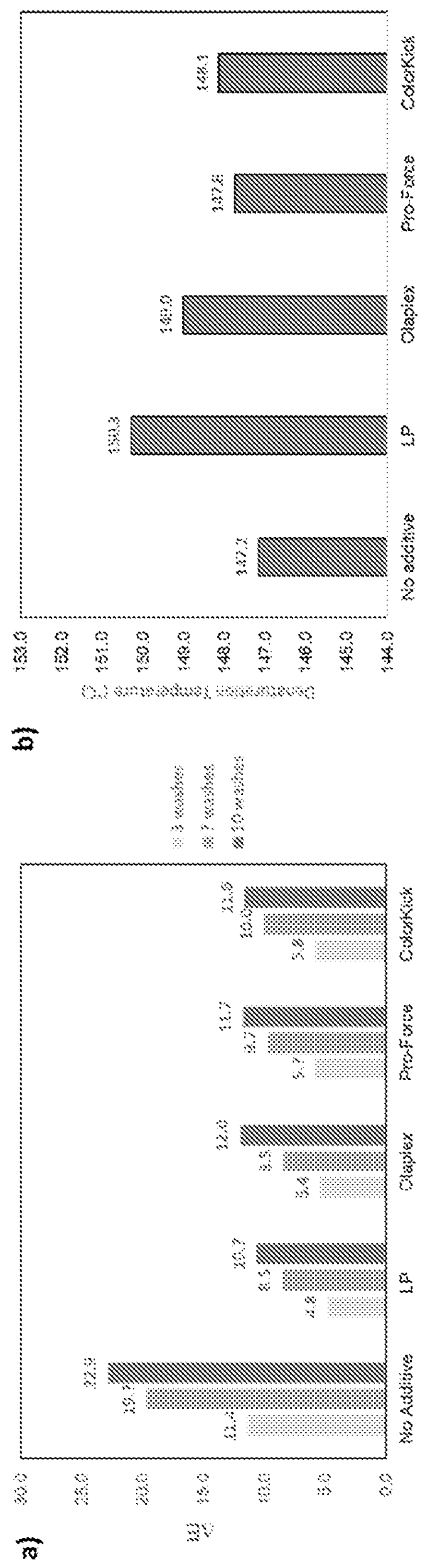
FIG. 35(*a*) depicts total color loss after 3, 7, and 10 washes of tresses treated either with LP developed system or commercial products.

A system encompassing a NALC based pre-treatment step along with a unique mixture of lead additives to be added during coloring process, and a post-treatment step based on GLCA-NAG ingredients was compared with commercially available products. Specifically, three most popular commercial systems were explored: Olaplex No. 1 (Bond Multiplier) and No. 2 (Bond Perfector) by Olaplex, Colorkick by Virtue, and Pro-Force Bonder 101 & Sealer 102 by Framesi. For the inventive system for this study, pre-treatment was performed with 0.5 wt % NALC while additive blend involved a mixture of 0.5 wt % ALA and 1 wt % glycine, and a post-treatment step included gluconolactone, citric acid, and N-acetyl glycine (GLCA-NAG) at 0.5 wt % concentration each. As can be seen from FIG. 35*a*, total color loss after 3, 7, and 10 washes for the inventive system was considerably lower compared to the commercial products, indicating superior performance of the inventive system in providing color retention benefits. In addition, FIG. 35*b* also shows that the use of the inventive system resulted in the highest boost in Td (+3° C.) compared to the commercial treatments indicating that along with long-lasting color benefits, the inventive system also delivers superior healthy benefits to hair. In a separate experiment, two other commercial systems were compared to the inventive system, i.plex 1 (Premium Bond) and i.plex 2 (Keratech I. Power) by Lakme and Color Hold by Alterna. Both systems showed inferior performance to LP system.

Example 4—Characterization of Color-Treated Hair Samples

Methods for Color Hair were Disclosed Herein.

Differential Scanning Calorimetry

Differential Scanning calorimetry (DSC) analysis was performed on both wet and dry hair. For wet method DSC, about 5-10 mg of hair was weighed into stainless steel pressure resistant sample pan and 50 μL of water was added. The pan was then sealed and samples were equilibrated overnight before DSC analysis. Samples were then heated from 30 to 250° C. at 5° C./min heating rate. For dry method DSC, about 5-10 mg of hair was weighed into aluminium sample pan and sealed with a lid. The lid was later pierced to allow moisture to escape during analysis. The samples were also heated from 30 to 250° C. at 5° C./min heating rate. The denaturation temperatures were recorded for the various hair samples.

Colorimetry

To determine the extent of color fastness and vibrancy, a number of tresses were prepared as described above in Examples 1-3. After the tresses were dried, a visual inspection comparing the tresses with control tresses was performed to evaluate vibrancy and color fastness of the dyes. Additionally, methods of the present invention were analyzed for color fastness on hair tresses using a Konica Minolta Chroma Meter CR-400 with the SpectraMagic™ NX Lite CM-S100w 1.91.0002 software package and were found to retain color after multiple shampoo cycles.

Sensory Testing

Blinded sensory testing was used to evaluate visual and tactile properties of tresses and mannequins after color treatment with additives. Overall, color treatment with additives provided hair with a manageable, smooth, soft, and conditioned feeling for tactile properties. Visual evaluation showed minimization of frizz, good fiber alignment, better shine, and better color retention.

Shine Band Testing

The shine characteristics of color-treated hair tresses with additives are compared with color-treated hair tresses without additives. A blinded sensory evaluator determines the sample that exhibits the best shine.

Mechanical Testing

Color-treated hair tresses with additives are compared with color-treated hair tresses without additives for the mechanical properties of single hair fibers when tested via INSTRON® 3342 mechanical testing.

Mechanical characterization of hair samples is carried out on the INSTRON® 3342 (Instron, Norwood MA) equipped with 100N load-cell (Instron #2519-103). Hair samples are mounted onto the instrument via modified Instron 2710-101 grips, which prevent the sample from slipping from the grips during testing. For example, single-fiber hair samples can be evaluated using an INSTRON®.

The extension pull test is preprogrammed into Bluehill Lite Software used to operate the instrument. The extension pull test is used to determine the stiffness, stretchiness, and strength of a hair by measuring the Young's Modulus, elongation at break, and ultimate tensile strength. The Young's Modulus is utilized as a measure of material stiffness, while the elongation at break is used as a measure of material flexibility. The sample is mounted onto the instrument such that the hair sample is fixed within the instrument grips. The instrument grip distance is adjusted such that the sample was at neutral extension as indicated by the instrument force being close to zero (+0.01 N). Subsequently, extension until sample failure is performed at 20 mm/min. The stress strain data recorded by instrument during the extension is exported to Excel where the reported mechanical properties are calculated.

An Excel template is used to automatically extract a number of parameters from the instrument generated data. The Young's modulus (YM) is calculated as the straight line slope of the stress-strain curve between 0.1% and 0.4%. The R squared value of the linear fit is above 0.98 or else the data point is discarded. The elongation at break is determined as the strain at which the sample, for example, a hair fiber, breaks. Ultimate stress is calculated as the maximum stress recorded during the experiment. Ultimate tensile strength is the capacity of a material to withstand loads tending to elongate. Ultimate tensile strength is the maximum stress that a material or sample can withstand while being pulled before breaking.

Water Uptake Testing

A hair sample is first dried in a desiccator for 16 hours. The sample is weighed and is placed into a humidity chamber at 90% RH for 15 minutes. The sample is then removed and weighed again.

Water Contact Angle

Water contact angles (CA) are measured using a goniometer equipped with an automated dispenser (Model 500, Rame-Hart). Advancing and receding angles are measured with the sessile drop method by depositing a droplet of 1 μL on the surface, then increasing the volume to 4 μL, finally decreasing it. Advancing angles are considered as the maximum angles observed during the droplet growth. Receding contact angles are measured in correspondence of the drop profile just before the contact surface reduction. Each CA value is averaged from measurements of four drops with an estimated maximum error of 4°. The CA is measured using distilled water.

Scanning Electron Microscopy (SEM)

To study morphological changes of the damaged hair surface with and without additives, scanning electron microscopy (SEM) analysis is employed. Hair is evaluated after bleaching, after dyeing, and after treatment with additives of virgin and bleached hair, as appropriate for each treatment method. Hair cuticles are expected to appear dramatically lifted after bleaching and dyeing as compared to virgin hair. Cuticle morphology is observed after various treatments. Hair cuticle appearance, especially lift of the cuticles and smoothness of the cuticle surface, are to be evaluated and compared to virgin hair and to dyed hair without additives.

Lowry Assay for Protein Loss

To study changes of the hair samples after color treatment with and without additives, a protein quantification assay is employed. After various chemical treatments such as bleaching, coloring, and additive treatments are applied, hair cuticles become damaged which result in higher protein loss. To quantify this loss with and without additives, a Modified Lowry Protein Assay was employed. Hair fibers are first cut into ¼ inch pieces and about 250 mg of hair is submerged into 4 mL of water in the scintiallation vial. Vials are then placed on the automatic vortex machine for 4 hours. The supernatant is then collected and diluted with 0.2N NaOH solution at 1:1 ratio for each hair sample and left to sit for 30 minutes for solubilization. About 200 μL of solubilized protein solution is then added into a 2 mL Eppendorf tube and mixed with 1 mL of Modified Lowry Reagent at 20-seconds intervals. Each sample is run in triplicate. After about 10 minutes, 100 μL of Folin-Ciocalteu Reagent is added into each sample and vortexed. The solutions are then left to develop for another 30 minutes. After 30 minutes, solutions are transferred into cuvettes and their absorbance at about 750 nm is measured using UV-Vis spectrophotometer. It is expected that after bleaching and after color treatment proteins are more easily leached out of the hair fibers as indicated by an increase in protein loss for virgin hair compared to bleached hair. In addition, chemical treatments with commercial products, such as hair dye, led to a further increase in protein loss. It is expected that protein loss will be reduced with additives.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A method for coloring hair, comprising:

i) providing a hair sample;

ii) applying a composition comprising an additive in a concentration of about 0.25% by weight to about 15% by weight of the total weight of the composition to the hair sample for a period of time, thereby producing a treated hair sample, wherein the additive is N-acetyl-L-cysteine; and iii) applying to the treated hair sample a mixture, comprising one or more hair dyes, thereby producing a color-treated hair sample.

2. A method for coloring hair, comprising:

i) providing a hair sample;

ii) applying to the hair sample for a period of time a mixture, comprising one or more hair dyes, thereby producing a color-treated hair sample; and iii) applying a composition comprising an additive in a concentration of about 0.25% by weight to about 15% by weight of the total weight of the composition to the color-treated hair sample, wherein the additive is a combination of citric acid and gluconolactone.

3. The method of claim 1, wherein the concentration of the additive is about 0.5% by weight to about 5% by weight of the total weight of the composition.

4. The method of claim 2, wherein the concentration of the additive is about 0.5% by weight to about 5% by weight of the total weight of the composition.

5. The method of claim 1, wherein the one or more hair dyes comprise one or more oxidative dyes.

6. The method of claim 2, wherein the one or more hair dyes comprise one or more oxidative dyes.

* * * * *